(12) United States Patent
Borowicz et al.

(10) Patent No.: US 9,585,942 B2
(45) Date of Patent: Mar. 7, 2017

(54) INSULIN ANALOGUE OR ITS PHARMACEUTICALLY ACCEPTABLE SALT, PHARMACEUTICAL COMPOSITION WITH PROLONGED THERAPEUTIC EFFECT, USE OF THE INSULIN ANALOGUE, DOSAGE METHOD AND METHOD OF TREATMENT OF DIABETES

(71) Applicant: INSTYTUT BIOTECHNOLOGII I ANTYBIOTYKÓW, Warsaw (PL)

(72) Inventors: Piotr Borowicz, Warsaw (PL); Andrzej Plucienniczak, Warsaw (PL); Jerzy Mikołajczyk, Warsaw (PL); Jarosław Antosik, Skierniewice (PL); Jacek Pstrzoch, Rajszwe (PL); Justyna Bernat, Magdalenka (PL); Diana Mikiewicz-Syguła, Warsaw (PL); Monika Bogiel, Pruszkow (PL); Dorota Stadnik, Warsaw (PL); Grażyna Plucienniczak, Warsaw (PL); Bożena Tejchman-Małecka, Warsaw (PL); Tadeusz Głąbski, Warsaw (PL); Iwona Sokołowska, Warsaw (PL); Dariusz Kurzynoga, Warsaw (PL); Anna Wojtowicz-Krawiec, Warsaw (PL); Marcin Zieliński, Warsaw (PL); Małgorzata Kęsik-Brodacka, Warsaw (PL); Natalia Łukasiewicz, Warsaw (PL); Violetta Cecuda-Adamczewska, Warsaw (PL); Monika Pawłowska, Warsaw (PL); Tomasz Pawlukowiec, Deszczno (PL); Jacek Stępniewski, Nowa Iwiczna (PL)

(73) Assignee: Instytut Biotechnologii i Antybiotykow, Warsaw (PL)

(*) Notice: Subject to any disclaimer, the term of this patent is extended or adjusted under 35 U.S.C. 154(b) by 0 days.

(21) Appl. No.: 14/403,513

(22) PCT Filed: May 22, 2013

(86) PCT No.: PCT/PL2013/000066
§ 371 (c)(1),
(2) Date: Nov. 24, 2014

(87) PCT Pub. No.: WO2013/176560
PCT Pub. Date: Nov. 28, 2013

(65) Prior Publication Data
US 2015/0164998 A1     Jun. 18, 2015

(30) Foreign Application Priority Data
May 23, 2012    (PL) ........................................ 399287

(51) Int. Cl.
A61K 38/28    (2006.01)
C07K 5/00    (2006.01)
C07K 7/00    (2006.01)
C07K 16/00    (2006.01)
C07K 17/00    (2006.01)
C07K 14/62    (2006.01)
A61K 38/00    (2006.01)
(Continued)

(52) U.S. Cl.
CPC .............. *A61K 38/28* (2013.01); *C07K 14/62* (2013.01); *A61K 38/00* (2013.01)

(58) Field of Classification Search
CPC ................................ C07K 14/62; A61K 38/28
See application file for complete search history.

(56) References Cited

U.S. PATENT DOCUMENTS

2011/0136736 A1* 6/2011 Borowicz .............. C07K 14/62
                                                    514/5.9

FOREIGN PATENT DOCUMENTS

PL    WO 2010002283 A2 *    1/2010 ............. C07K 14/62

OTHER PUBLICATIONS

Garnock-Jones and Plosker "Insulin Glulisine a Review of its Use in the Management of Diabetes Mellitus" Drugs 69:1035-1057. Published 2009.*
PCT International Publication No. WO 2010/002283 A2 (Inst Biotechnologii I Antybiot [PL]; Piotr Borowics [PL]; Pluciennicza); published Jan. 7, 2010.
International Search Report issued by the International Searching Authority (ISA/O.E.P.M.) on Sep. 25, 2013 in connection with International Application No. PCT/PL2013/000066.

* cited by examiner

*Primary Examiner* — Christina Bradley
*Assistant Examiner* — Zachary J Miknis
(74) *Attorney, Agent, or Firm* — Gary J. Gershik; Cooper & Dunham LLP

(57) ABSTRACT

The invention relates to an insulin analogue or its pharmaceutically acceptable salt, pharmaceutical composition with prolonged therapeutic effect, application of the insulin analogue, dosage method and method of treatment of diabetes. In more detail, the solution pertains to compounds being stable insulin analogues which are pharmaceutically active and characterized by a prolonged, flat, truly peakless course of glucose concentration vs. time during repeated administration and which do not show strong 24 hours fluctuations of glucose concentration, or the so-called "sawteeth effect", during this time. Results of studies of compounds included in the scope of this application indicate an improvement in the effects of diabetes treatment by avoiding the hitherto occurring adverse influence of changes in glucose concentration throughout the entire day on a patient's organism, e.g. night hypoglycaemias, because truly peakless, long-acting insulin should reproduce correct endogenous insulin secretion in the therapy, as is provided by a healthy pancreas at a proper and constant 24 hours level.

16 Claims, 13 Drawing Sheets

INSULIN ANALOGUE OR ITS PHARMACEUTICALLY ACCEPTABLE SALT, PHARMACEUTICAL COMPOSITION WITH PROLONGED THERAPEUTIC EFFECT, USE OF THE INSULIN ANALOGUE, DOSAGE METHOD AND METHOD OF TREATMENT OF DIABETES

The invention relates to an insulin analogue or its pharmaceutically acceptable salt, pharmaceutical composition with prolonged therapeutic effect, use of the insulin analogue, dosage method and method of treatment of diabetes. In more detail, the invention pertains to compounds being stable insulin analogues which are pharmaceutically active and characterised by a prolonged, flat, truly peakless course of glucose concentration vs. time during repeated administration and which do not show strong 24 hours fluctuations of glucose concentration, or the so-called "sawteeth effect", during this time. Results of studies of compounds included in the scope of this application indicate an improvement in the effects of diabetes treatment by avoiding the hitherto occurring adverse influence of changes in glucose concentration throughout the entire day on a patient's organism, e.g. night hypoglycaemias, because truly peakless, long-acting insulin should reproduce correct endogenous insulin secretion in the therapy, as is provided by a healthy pancreas at a proper and constant 24 hours level.

Insulin and its various analogues are commonly used in the treatment of diabetes. Some of these are manufactured on a large commercial scale. Many different modified insulin derivatives and pharmaceutical preparations with various action profiles containing these compounds are known; however, there is an on-going search for medication enabling one to maintain a constant, i.e. basic level, of glucose in the human organism over a long period of time, i.e. during the night and between meals.

In the treatment of diabetes, various analogues of human insulin are used, exhibiting a prolonged action effect. Modifications of the primary structure of insulin lead to a change in the physicochemical and biological properties of the analogues and, in consequence, to a change in their pharmacokinetic and pharmacodynamic parameters.

Insulin analogues with prolonged activity are called peakless or almost peakless compounds because of their pharmacokinetic and pharmacodynamic parameters. An important and sought feature of such insulin analogues is therefore to maintain a basic level of glucose in the organism without fluctuations, particularly without distinct maxima and minima of their effect. Analogues with such characteristics imitate the natural insulin secretion best, preventing and reducing incidents of harmful hypoglycaemia, particularly night hypoglycaemia (Heller S, Kozlovski P, Kurtzhals P. Insulin's 85$^{th}$ anniversary—An enduring medical miracle. *Diabetes Research and Clinical Practice*. 2007; 78(2): 149-158).

Recombinant human insulin analogues with prolonged effect that are known and used in medicine are built by either acylation of the ε-amine group of lysine in the B29 position using an aliphatic acid with a dozen or so carbon atoms, causing an affinity to albumin, or by introduction of additional basic amino acids to the C-terminus of the B chain of human insulin, resulting in an increase in the isoelectric point to a value higher than 6. In the latter case, it is possible, in consequence, to produce a pharmaceutical form of the medication, being a solution for injection in a slightly acidic medium, from which the active substance precipitates after subcutaneous administration and in contact with body fluids with a pH of approx. 7.4. From such a microdeposit, an active insulin derivative liberates, with a constant, comparatively low rate, resulting in its prolonged activity. The compound described in patent application No. WO 2006/096079 is one example of such a derivative. However, apart from a favourable change in pharmacokinetic and pharmacodynamic properties, resulting from the introduction of additional basic amino acids, a deterioration of the chemical stability of these analogues in solutions with an acidic pH is observed, resulting from, most of all, asparagine deamidation in position A21, occurring in the acidic medium. This problem is solved by exchange of A21Asn to another amino acid, such as aspartic acid, glycine, alanine, threonine and others. A derivative of recombinant human insulin, with A-chain asparagine (A21Asn) replaced with glycine (A21Gly) and two arginine residues attached to the C-terminus of the chain B, is one of such analogues. This is the so-called insulin glargine, manufactured under the name Lantus® (U.S. Pat. No. 5,656,722). Other stable derivatives with carboxylic group of the A21Asn residue protected by adding one amino acid in A22 position are described in WO 2010/002283 A2.

In spite of existing solutions, there is a constant search for an insulin analogue which will not exhibit undesirable effects such as a distinct maximum of activity in spite of the formation of a microdeposit after subcutaneous administration, because only a stable and flat activity profile protects from rapid fluctuations in the sugar level in blood and—being very important—ensures achieving values of diabetes control parameters favourable for a patient (e.g. HbA$_1$c, stable levels of which decrease the risk of diabetic macro- and microangiopathic complications) and protect from severe hypoglycaemia episodes, particularly during the night. In the case of the existing solutions, however, apart from a favourable change in pharmacokinetic and pharmacodynamic properties, resulting from the introduction of additional amino acids, a deterioration of the chemical stability of these analogues in solutions with an acidic pH is observed.

However, known long-acting insulin analogues with a structure similar to that of the compounds included in this application, constituting progress in diabetes treatment, exhibit several undesirable features, e.g. the insulin analogue widely used in therapy—insulin glargine—in spite of a microdeposit formation after subcutaneous administration, exhibits a distinct activity maximum (e.g. Heise T, Nosek L, Renn B B, Endahl L, Heinemann L, Kapitza C, Draegeret E. Lower within-subject variability of insulin detemir in comparison to NPH insulin and insulin glargine in people with type 1 diabetes. *Diabetes*. 2004; 53(6):1614-1620; Klein O, Lynge J, Endahl L, Damholt B, Nosek L, Heise T. Albumin-bound basal insulin analogues (insulin detemir and NN344): comparable time-action profiles but less variability than insulin glargine in type 2 diabetes. *Diabetes Obes. Metab.* 2007; 9(3): 290-299). At the same time, in a long-term therapy (12 days), the so-called "sawteeth effect" is observed for this analogue, consisting in large differences between maximal and minimal glucose levels during the day and night, indicating a large variability of action of this compound (www.novonordisk.com/images/investors/investor_pr esentations/2009/PiperJaffray.pdf).

The second of the long-acting analogues known and used in medicine—insulin detemir—with a different structure than insulin glargine, and other mechanism of the prolonged action, is not a truly peakless compound either (Klein O, Lynge C, Endahl L, Damholt B, Nosek L, Heise T. Albumin-bound basal insulin analogues (insulin detemir and NN344):

comparable time-action profiles but less variability than insulin glargine in type 2 diabetes. *Diabetes Obes Metab.* 2007; 9(3): 290-299; Chaykin L B. Insulin Detemir and Its Unique Mechanism of Action. *The Internet Journal of Endocrinology.* 2007; 4(1), ISSN: 1540-2606, www.ispub-.com/journal/the-internet-journal-of-endocrinologyvolume-4-number-1/insulin-detemir-and-its-unique-mechanism-of-action.html). This analogue is also characterised by a shorter time of activity (Porcellati F, Rossetti P, Busciantella N R, Marzotti S, Lucidi P, Luzio S, Owens D R, Bolli G B, Fanelli C G. Comparison of Pharmacokinetics and Dynamics of the Long-Acting Insulin Analogues Glargine and Detemir at Steady State in Type 1 Diabetes: A doubleblind, randomised, crossover study. *Diabetes Care.* 2007; 30(10): 2447-2452).

The aim of the invention was to obtain compounds being stable insulin analogues which are pharmaceutically active and characterised by a prolonged, flat, truly peakless course of glucose concentration vs. time during repeated administration (4 weeks) and which do not show strong 24 hours fluctuations of glucose concentration, or the so-called "sawteeth effect", during this time. None of the hitherto known and described long-acting insulin analogues show such a combination of activity parameters—desirable and favourable for the patient. At the same time, new insulin analogues, included in this application, exhibit additional, possibly favourable pharmaceutical properties, e.g. a stability suitable for formation of stable pharmaceutical forms of the drug. Studies of both new insulin analogues, and their pharmaceutical forms, carried out using standard methods according to valid pharmacopoeic requirements, indicate their very favourable pharmacokinetic and pharmacodynamic parameters, observed during long-term therapy, and also prove that their chemical stability is as good as that of human insulin and its analogues known and used in the therapy, and it is positively better than that of many known insulin derivatives, e.g. the ones described in application No. WO 2010/002283 A2.

The aim defined above was unexpectedly achieved in this invention. In this case, the dependence between activity and structure, causing a prolonged activity and flat 24 hours activity profile after repeated administration, and the stability proper for the drug, exceeds the expectations by a synergistic action, being neither a sum nor an average of the biological activity of these proteins. The discussed requirements are met by insulin analogues according to the invention.

It was unexpectedly ascertained that a prolonged, flat and truly peakless course of glucose concentration vs. time during repeated administration, and a glycaemia profile exhibiting no large 24 hours fluctuations during this time, were shown by derivatives of human insulin, forming a microdeposit after subcutaneous administration in the form of solution with a slightly acidic pH, as a result of decreased solubility in a neutral physiological medium, characterised by the fact that their isoelectric point was increased in comparison to human insulin by replacing asparagine in position 3 of the chain B with a basic amino acid such as lysine (B3Lys) or arginine (B3Arg). An additional change in the isoelectric point was achieved by adding arginine to the C-terminus of the chain B (B31Arg). Stability of these compounds in a slightly acidic medium necessary for production of pharmaceutical preparations of these derivatives in the form of a solution was achieved by adding another neutral amino acid (at position A22).

It was unexpectedly found that compounds of such a type led to a practically flat 24 hours course of the curve of the glucose concentration in blood vs. time in the days following the achievement of an equilibrium, enabling the obtainment of a constant basic glucose level in prolonged therapy, simulating the natural secretion of the hormone accurately. The glycaemic profile remains generally unchanged in a dosage range set for 12 hours in the studies, which is observed in the case of the analogues being the subject of the application.

So, the aim of the invention is to provide new insulin analogues, characterised by a desirable biological activity, i.e. prolonged action at a constant level, without formation of a maximum of biological activity, equivalent to the natural secretion of a basic insulin level in a healthy organism, ensuring a constant glucose level in blood during long-term therapy (while administering once per day or more rarely), at the same time exhibiting chemical stability proper for pharmaceutical forms in acidic injection solutions with pH from 3.5 to 5.0.

According to the invention, the insulins listed below are examples of derivatives with a general formula 1:
A22Gly-B3Lys-B31Arg—human insulin (insulin GK3R)
A22Ala-B3Lys-B31Arg—human insulin (insulin AK3R)
A22Ser-B3Lys-B31Arg—human insulin (insulin SK3R)
A22Thr-B3Lys-B31Arg—human insulin (insulin TK3R)
A22Gly-B3Arg-B31Arg—human insulin (insulin GR3R)
A22Ala-B3Arg-B31Arg—human insulin (insulin AR3R)
A22Ser-B3Arg-B31Arg—human insulin (insuliSR3R)
A22Thr-B3Arg-B31Arg—human insulin (insulin TR3R)

In the description of the invention, in the light of the terminology used, recombinant proinsulin means a polypeptide chain, in which chains A and B of human insulin are connected by link C, preferably being a Lys-Arg or Arg-Arg dipeptide, or even by the single Arg residue only. As recombinant preproinsulin, a combination of proinsulin with an additional leader polypeptide is acknowledged, e.g. with ubiquitine or SOD, or their fragments or modified fragments.

For simplification of names of recombinant human insulin analogues and their proinsulins (and preproinsulins), being the subject of the invention, symbols composed of a name were assumed to them: (pre)pro)insulin and an alphanumeric code consisting of several characters, denoting amino acid residues, which are additional or altered instead of those present in the parent recombinant human (pre)pro)insulin. In the discussed case, these letters are consistent with the one-letter designation of amino acid residues acknowledged in world literature.

One aspect of the invention is also a pharmaceutical composition characterised in that it contains an effective quantity of an insulin analogue or its pharmaceutically acceptable salt. The salt of the recombinant human insulin analogue, according to the invention, may be, for instance, an alkaline metal salt or an ammonium salt.

In general, auxiliary agents in compositions, according to the invention, are conventionally used auxiliary agents, the same as the ones used in pharmaceutical protein formulations, including those of insulins and their analogues.

An isotonic substance, according to the invention, may be every pharmaceutically acceptable substance allowing for the obtaining of an isoosmotic solution in relation to the plasma of human blood. Typical isotonic agents used in pharmaceutics include sodium chloride, mannitol, glycine and glycerol. Using glycerol is preferable.

Useful preservative agents for use in a pharmaceutical composition, according to the invention, are compounds selected from a group including m-cresol, phenol or their mixtures and substances counteracting aggregation of insulin analogues—polysorbates or alkyl saccharides.

The new analogues, as with recombinant human insulin, are preferably stabilised with an admixture of zinc ions introduced to the solution, most preferably, in the form of, among others, zinc chloride, acetate or oxide.

The subject of the invention is an insulin analogue or its pharmaceutically acceptable salt, comprising two polypeptides forming chain A and chain B, characterised in that it is defined by general formula 1

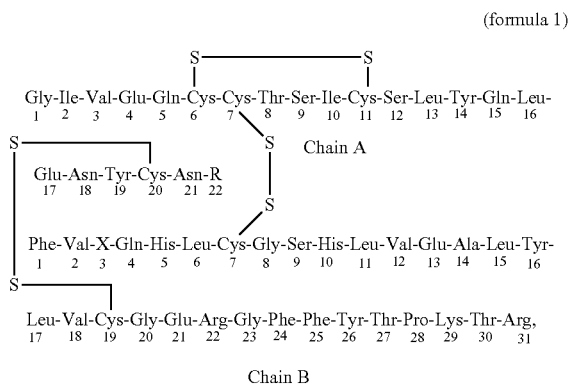

(formula 1)

where X is a basic amino acid and is lysine or arginine, and R is a neutral amino acid selected from among glycine, alanine, serine or threonine, and
wherein amino acid sequence of chain A being selected from among SEQ ID No. 1 to 4, and amino acid sequence of chain B being selected from among SEQ ID No. 5 or SEQ ID No. 6,
and that the insulin analogue has an isoelectric point with values of from 6 to 8.

Preferably, the analogue is an analogue of recombinant human insulin.

Preferably, the amino acid sequences are selected in such a way that when X is Lys, then R is Gly or Ala or Ser or Thr, while when X is Arg, then R is Gly or Ala or Ser or Thr.

Preferably, when X is Lys, then R is Ser or Ala.

Preferably, the amino acid sequences of chain A and chain B are selected from among the sequences SEQ ID No. 1 with SEQ ID No. 5, SEQ ID No. 2 with SEQ ID No. 5, SEQ ID No. 3 with SEQ ID No. 5, SEQ ID No. 4 with SEQ ID No. 5, SEQ ID No. 1 with SEQ ID No. 6, SEQ ID No. 2 with SEQ ID No. 6, SEQ ID No. 3 with SEQ ID No. 6 or SEQ ID No. 4 with SEQ ID No. 6.

Another subject of the invention is a pharmaceutical composition with a prolonged therapeutic effect, characterised in that it comprises an insulin analogue or its pharmaceutically acceptable salt defined above in a quantity of 1.3 mg/ml to 20 mg/ml, while the glycaemic profile of the composition remains unchanged in the dosage range determined in the studies for at least 12 hours, and that in the days following the achievement of an equilibrium, a flat 24 hours course of the glucose concentration in blood vs. time is maintained.

Preferably, the insulin analogue or its pharmaceutically acceptable salt is contained in a quantity of 1.4 mg/ml to 10 mg/ml.

Preferably, it exhibits a prolonged action at a constant level without formation of a maximum of biological activity, the level being pharmacologically equivalent to the natural secretion of the basic level of insulin in a healthy organism, at the same time exhibiting stability in acidic injection solutions with pH values from 3.5 to 5.0, which is proper for pharmaceutical forms of drugs.

Preferably, it additionally comprises from 0 to 60 µg/ml of zinc, most preferably from 10 to 60 µg/ml.

Preferably, it additionally comprises an isotonic substance, a preservative and, optionally, substances counteracting aggregation, which are used in protein formulations.

Another subject of the invention is an insulin analogue or its pharmaceutically acceptable salt defined above for the treatment of diabetes in mammals.

Another subject of the invention is an application of the insulin analogue or its pharmaceutically acceptable salt defined above for the production of a drug with a prolonged therapeutic effect for the treatment of diabetes.

Preferably, the effective amount of the drug per dose is contained in the range from 0.3 to 180 µg/kg of body weight, with the drug being administered once per day or more rarely.

Another subject of the invention is a dosage method of the pharmaceutical composition with a prolonged therapeutic effect, as defined above, characterised in that the composition is administered once per day or more rarely, with the dose amounting to 0.3 to 180 µg/kg of body weight.

Another subject of the invention is a method for treatment of mammals suffering from diabetes, characterised in that the effective amount of the pharmaceutical composition, as defined in claims 5 to 9, in the range of 0.3 to 180 µg/kg of body weight is administered to the mammal requiring such treatment.

Preferably the mammal is human.

For better illustration of the invention, the solution is depicted in Figures, where:

Figure 1:
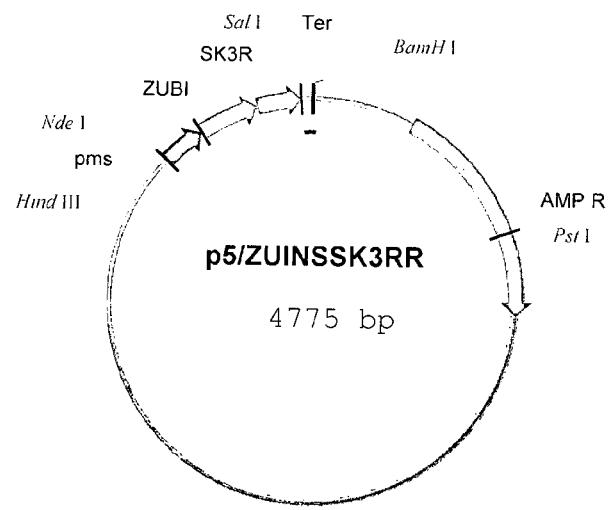
FIG. 1 shows the structure of the p5/ZUINSSer(22A)Lys(3B)Arg(31B)Arg(32B) plasmid containing a gene coding the recombinant proinsulin SK3RR.

For better explanation of the invention, the description is supplemented with a detailed discussion of its embodiments.

EXAMPLES

According to the invention, the insulins listed below are examples of derivatives with a general formula 1:
A22Gly-B3Lys-B31Arg—human insulin (Insulin GK3R)
A22Ala-B3Lys-B31Arg—human insulin (insulin AK3R)
A22Ser-B3Lys-B31Arg—human insulin (insulin SK3R)
A22Thr-B3Lys-B31Arg—human insulin (Insulin TK3R)
A22Gly-B3Arg-B31Arg—human insulin (insulin GR3R)
A22Ala-B3Arg-B31Arg—human insulin (insulin AR3R)
A22Ser-B3Arg-B31Arg—human insulin (insulin SR3R)
A22Thr-B3Arg-B31Arg—human insulin (insulin TR3R)

Insulin analogues, being the subject of the invention, were obtained using standard methods of genetic engineering. For this purpose, modifications of the gene of recombinant human proinsulin were constructed using genetic techniques, such as a site-directed mutagenesis reaction. A point mutagenesis reaction was carried out using the Stratagene kit (cat. No. 200518-5), and plasmid DNA plGALZUINS—p5/ZUINS or plGTETZUINS—p6/ZUINS was used as a template. Any other DNA containing a proper sequence coding the recombinant human proinsulin or preproinsulin may also be used as a template.

The reaction mixture was used to transform competent cells of a suitable *Escherichia coli* strain, such as DH5α, DH5 or HB101, while—according to the idea of the invention—it is possible to use the cells of other *E. coli* strains or cells of other microorganisms, or other known cell lines suitable for the expression of recombinant proteins. A plasmid containing a defined modification of the gene of recombinant human proinsulin was isolated and sequenced in order to check the correctness of the nucleotide sequence. According to one variant of the invention, the plasmid with the modified gene of recombinant human proinsulin was used for transformation of competent cells of *E. coli* DH5α, and a bacterial culture was made on a LB nutrient medium with the addition of a selection antibiotic (0.01 mg/ml) in a volume of 500 ml, at 37° C., 200 rpm, for 18 hours. The bacterial material was transferred to a strain bank, and samples with a 1:1 ratio of the bacterial culture to 40% glycerol were deposited at −70° C.

The variants of recombinant preproinsulin obtained by expression in *E. coli* strains were isolated after splitting the cells in the form of inclusion bodies, which were then subjected to standard processes of purification of fusion proteins. The hybrid protein with the insulin analogue (preproinsulin) or proinsulin, obtained after renaturation, was subjected to a controlled action of trypsin, analogically as in the case of several previously known and described methods (e.g. Kemmler W, Peterson J D, Steiner D F. I. Conversion in vitro with trypsin and carboxypeptidase B. *J. Biol. Chem.* 1971; 246: 6786-6791, and patents U.S. Pat. No. 6,686,177 and U.S. Pat. No. 6,100,376). The obtained insulin analogues were subjected to purification using known methods, mainly low pressure chromatography, ultrafiltration and/or HPLC. In order to obtain a crystalline form, the substances were precipitated from an adequately purified solution of the insulin analogue, preferably with the addition of a metal ion, most preferably zinc.

The basic physicochemical property of the recombinant human insulin analogues, according to the invention, differentiating them from human insulin, is their value of the isoelectric point, amounting to 6 to 8. This means good solubility of the compounds in solutions with a pH from acidic to slightly acidic. This property enabled the preparation of a pharmaceutical composition—solutions of new insulin derivatives at acidic pH.

In the case of the pharmaceutical composition, according to the invention, the pH value of the solution amounts to approx. 3.5 to approx. 5.0, preferably 4.0 to 4.5. The structures of molecules of recombinant human insulin and their analogues shown above, containing the same core protein group, differ from one another. The lability of the undefined end fragment of chain B of insulin SK3R, being less labile in comparison with A22Gly-B31Arg—human insulin, or the so-called insulin GR (WO 2010/002283 A2), also influences the properties of the compound, according to the invention, including the increased chemical stability and biological activity of this analogue.

The following exemplary constitution of compositions containing recombinant derivatives of human insulin, according to the invention, was developed: 10-500 U/ml of a recombinant human insulin analogue or its pharmaceutically acceptable salt, 16 mg/ml of glycerol, 3 mg/ml of m-cresol, 10-60 µg/ml of zinc and water for injection up to 1 ml. The amount of the active substance used in a composition, according to the invention, is about 1-1600, preferably 10-1200, more preferably 10-500 U/ml. In the case of each human insulin analogue, being the subject of the invention, by 1 unit (1 U), 1 in-house unit is understood, containing the same number of moles of the analogue, as 1 international unit of human insulin, corresponding to 6 nmol (or $6 \times 10^{-9}$ mol).

Another aspect of the invention is also a method of treatment of patients with diabetes, according to which an effective amount of a pharmaceutical composition containing an insulin analogue or its salt, according to the invention, is administered to the patient requiring such treatment.

Example 1

Construction of
p5/ZUINSSer(22A)Lys(3B)Arg(31B)Arg(32B)
Plasmid and Obtaining a Strain Transformed with it In order to obtain the gene of recombinant proinsulin SK3RR, a p5/ZUINSSer(22A)Arg(31B)Arg(32B) plasmid was used, which codes the recombinant proinsulin SRR and is described in patent application No. 2010/002283 A2, Example 3. In this plasmid, the DNA fragment coding a precursor of recombinant insulin is attached to a modified gene of synthetic ubiquitin. A peptide constituting a part of the ubiquitin is a carrier requisite of high yield of fusion protein synthesis in *E. coli*. The region coding the modified fusion protein was placed under the control of a pms promotor (WO 05066344 A2). The plasmid includes an ampicillin resistance gene, and it is a derivative of the plGAL1 vector (Gene Bank AY424310). In the ubiquitin gene, arginine codons were replaced with alanine codons, and an additional arginine codon was attached to the C-terminus of the ubiquitin gene.

The recombinant proinsulin SK3RR gene differs from the initial proinsulin SRR gene by the fact that the AAC codon (Asn) is replaced with the AAA codon for lysine (Lys) in position 3 of chain B. In order to modify the coding sequence of the recombinant SRR proinsulin gene in the above way, the following primers for a point mutagenesis reaction were designed:

```
KSRL
5' GGTGGTCGTTTTGTCAAACAGCAC 3'
                 Lys

KSRP
5' ACCACACAGGTGCTGTTTGACAAA 3'
                    Lys
```

Utilising plasmid DNA p5/ZUINSSer(22A)Arg(31B)Arg (32B) as a template, the point mutagenesis reaction was carried out using a kit from Stratagene (cat. No. 200518-5). By known methods, the reaction mixture was used to transform competent cells of *Escherichia coli* DH5α. The plasmid was isolated and sequenced in order to verify the presence of AAA nucleotides coding lysine and the correctness of the plasmid sequence. The obtained p5/ZUINSSer (22A)Lys(3B)Arg(31B)Arg(32B) plasmid with the recombinant proinsulin SK3RR gene was used to transform competent cells of *E. coli* DH5α, and a bacterial culture was made on an LB nutrient medium with the addition of ampicillin (0.01 mg/ml) in a volume of 500 ml, at 37° C., 200 rpm, for 18 hours. The bacterial material for the strain bank was prepared, and samples with a 1:1 ratio of the bacterial culture to 40% glycerol were deposited at −70° C.

The obtained *Escherichia coli* strain is an initial biological material in the process of insulin SK3R production by biosynthesis, according to Example 13.

Genetic Construction of p5/ZUINSSer(22A)Lys(3B)Arg (31B)Arg(32B) Plasmid

The p5/ZUINSSer(22A)Lys(3B)Arg(31B)Arg(32B) plasmid comprising 4775 base pairs is composed of the following regulator sequences and genes:
  from 374 bp to 1234 bp, the ampicillin resistance gene AMP R is located,
  from 4158 bp to 4323 bp, the region coding pms promoter is located,
  from 4327 bp to 4554 bp, the sequence coding the modified gene of synthetic ubiquitin ZUBI is included,
  from 4558 bp to 4722 bp, the sequence coding the gene of the recombinant proinsulin SK3RR is located,
  from 4729 bp to 4775 bp, the region coding the transcription terminator Ter is located. The structure of the p5/ZUINSSer(22A)Lys(3B)Arg(31B)Arg(32B) plasmid, containing the gene coding the recombinant proinsulin SK3RR, is shown schematically in FIG. 1, and its nucleotide and amino acid sequences as SEQ. No. 23.

Example 2

Construction of
p5/ZUINSGly(22A)Lys(3B)Arg(31B)Arg(32B)
Plasmid and Obtaining a Strain Transformed with it In order to obtain a gene of recombinant proinsulin GK3RR, p5/ZUINSSer(22A)Lys(3B)Arg(31B)Arg(32B) plasmid was used, coding the recombinant proinsulin SK3RR, and obtained according to Example 1. The gene of the recombinant proinsulin GK3RR differs from the initial gene of proinsulin SK3RR by the fact that the TCT codon (Ser) has been replaced with a GGT codon for glycine (Gly) in position 22 of chain A.

In order to modify the gene of the coding sequence of recombinant proinsulin SK3RR in the above way, the following primers for a point mutagenesis reaction were designed:

```
GLYP
5' TACTGCAATGGTTAAGTCGACTCTAGC 3'
         GlySTOP

GLYL
5' GAGTCGACTTAACCATTGCAGTAGTT 3'
              Gly
```

The point mutagenesis reaction was carried out using the Stratagene kit (cat. No. 200518-5). Isolation and verification of correctness of the plasmid nucleotide sequence, and obtaining *E. coli* DH5α bacteria with the p5/ZUINSGly(22A)Lys(3B)Arg(31B)Arg(32B) plasmid, were carried out as in Example 1.

The obtained *Escherichia coli* strain is an initial biological material in the process of insulin GK3R production by biosynthesis, according to Example 11.

Example 3

Construction of
p5/ZUINSAla(22A)Lys(3B)Arg(31B)Arg(32B)
Plasmid and Obtaining a Strain Transformed with it In order to obtain a gene of recombinant proinsulin AK3RR, p5/ZUINSSer(22A)Lys(3B)Arg(31B)Arg(32B) plasmid was used, coding the recombinant proinsulin SK3RR, obtained according to Example 1. The gene of the recombinant proinsulin AK3RR differs from the initial gene of proinsulin SK3RR by the fact that the TCT codon (Ser) has been replaced with a GCT codon for alanine (Ala) in position 22 of chain A.

In order to modify the gene of the coding sequence of recombinant proinsulin SK3RR in the above way, the following primers for a point mutagenesis reaction were designed:

```
ALAP
5' TACTGCAATGCTTAAGTCGACTCTAGC 3'
         AlaSTOP

ALAL
5' GAGTCGACTTAAGCATTGCAGTAGTT 3'
              Ala
```

The point mutagenesis reaction was carried out using the Stratagene kit (cat. No. 200518-5). Isolation and verification of correctness of the plasmid nucleotide sequence, and obtaining *E. coli* DH5α bacteria with the p5/ZUINSAla(22A)Lys(3B)Arg(31B)Arg(32B) plasmid, were carried out as in Example 1.

The obtained *Escherichia coli* strain is an initial biological material in the process of insulin AK3R production by biosynthesis, according to Example 12.

Example 4

Construction of
p5/ZUINSThr(22A)Lys(3B)Arg(31B)Arg(32B)
Plasmid and Obtaining a Strain Transformed with it In order to obtain a gene of recombinant proinsulin TK3RR, p5/ZUINSSer(22A)Lys(3B)Arg(31B)Arg(32B) plasmid was used, coding the recombinant proinsulin SK3RR, obtained according to Example 1. The gene of the recombinant proinsulin TK3RR differs from the initial gene of proinsulin SK3RR by the fact that the TCT codon (Ser) has been replaced with an ACC codon for threonine (Thr) in position 22 of chain A.

In order to modify the gene of the coding sequence of recombinant proinsulin SK3RR in the above way, the following primers for a point mutagenesis reaction were designed:

```
THRP
5' TACTGCAATACCTAAGTCGACTCTAGC 3'
         ThrSTOP

THRL
5' GAGTCGACTTAGGTATTGCAGTAGTT 3'
              Thr
```

The point mutagenesis reaction was carried out using the Stratagene kit (cat. No. 200518-5). Isolation and verification of correctness of the plasmid nucleotide sequence, and obtaining *E. coli* DH5α bacteria with the p5/ZUINSThr(22A)Lys(3B)Arg(31B)Arg(32B) plasmid, were carried out as in Example 1.

Example 5

Construction of
p5/ZUINSGly(22A)Arg(3B)Arg(31B)Arg(32B)
Plasmid and Obtaining a Strain Transformed with it In order to obtain the gene of recombinant proinsulin GR3RR, p5/ZUINSGly(22A)Arg(31B)Arg(32B) plasmid was used, which codes the recombinant proinsulin GRR and is described in patent application No. WO 2010/002283 A2, Example 2. The gene of the recombinant proinsulin GR3RR differs from the initial gene of proinsulin GRR by the fact that the AAC codon (Asn) has been replaced with a CGT codon for arginine (Arg) in position 3 of chain B.

In order to modify the gene coding the sequence of recombinant proinsulin GRR in the above way, the following primers for a point mutagenesis reaction were designed:

```
ARGP
5' TTTGTCCGTCAGCACCTGTGTGGTTCT 3'
         Arg

ARGL
5' CAGGTGCTGACGGACAAAACGACCACC 3'
              Arg
```

The point mutagenesis reaction was carried out using the Stratagene kit (cat. No. 200518-5). Isolation and verification of correctness of the plasmid nucleotide sequence, and obtaining *E. coli* DH5α bacteria with the p5/ZUINSGly(22A)Arg(3B)Arg(31B)Arg(32B) plasmid, were carried out as in Example 1.

Example 6

Construction of
p5/ZUINSAla(22A)Arg(3B)Arg(31B)Arg(32B)
Plasmid and Obtaining a Strain Transformed with it In order to obtain a gene of recombinant proinsulin AR3RR, p5/ZUINSGly(22A)Arg(3B)Arg(31B)Arg(32B) plasmid was used, coding the recombinant proinsulin GR3RR, obtained according to Example 5. The gene of the recombinant proinsulin AR3RR differs from the initial gene of proinsulin GR3RR by the fact that the GGT codon (Gly) has been replaced with a GCT codon for alanine (Ala) in position 22 of chain A.

In order to modify the gene of the coding sequence of recombinant proinsulin GR3RR in the above way, the following primers for a point mutagenesis reaction were designed:

```
ALAP
5' TACTGCAATGCTTAAGTCGACTCTAGC 3'
          AlaSTOP

ALAL
5' AGAGTCGACTTAAGCATTGCAGTAGTT 3'
              Ala
```

The point mutagenesis reaction was carried out using the Stratagene kit (cat. No. 200518-5). Isolation and verification of correctness of the plasmid nucleotide sequence, and obtaining *E. coli* DH5α bacteria with the p5/ZUINSAla (22A)Arg(3B)Arg(31B)Arg(32B) plasmid, were carried out as in Example 1.

Example 7

Construction of
p5/ZUINSSer(22A)Arg(3B)Arg(31B)Arg(32B)
Plasmid and Obtaining a Strain Transformed with it In order to obtain a gene of recombinant proinsulin SR3RR, p5/ZUINSGly(22A)Arg(3B)Arg(31B)Arg(32B) plasmid was used, coding the recombinant proinsulin GR3RR, obtained according to Example 5. The gene of the recombinant proinsulin SR3RR differs from the initial gene of proinsulin GR3RR by the fact that the GGT codon (Gly) has been replaced with a TCT codon for serine (Ser) in position 22 of chain A.

In order to modify the gene of the coding sequence of recombinant proinsulin GR3RR in the above way, the following primers for a point mutagenesis reaction were designed:

```
SERP
5' TACTGCAATTCTTAAGTCGACTCTAGC 3'
          SerSTOP

SERL
5' AGAGTCGACTTAAGAATTGCAGTAGTT 3'
              Ser
```

The point mutagenesis reaction was carried out using the Stratagene kit (cat. No. 200518-5). Isolation and verification of correctness of the plasmid nucleotide sequence, and obtaining *E. coli* DH5α bacteria with the p5/ZUINSSer (22A)Arg(3B)Arg(31B)Arg(32B) plasmid, were carried out as in Example 1.

The obtained *Escherichia coli* strain is an initial biological material in the process of insulin SR3R production by biosynthesis, according to Example 14.

Example 8

Construction of
p5/ZUINSThr(22A)Arg(3B)Arg(31B)Arg(32B)
Plasmid and Obtaining a Strain Transformed with it In order to obtain a gene of recombinant proinsulin TR3RR, p5/ZUINSGly(22A)Arg(3B)Arg(31B)Arg(32B) plasmid was used, coding the recombinant proinsulin GR3RR, obtained according to Example 5. The gene of the recombinant proinsulin TR3RR differs from the initial gene of proinsulin GR3RR by the fact that the GGT codon (Gly) has been replaced with an ACT codon for threonine (Thr) in position 22 of chain A.

In order to modify the gene of the coding sequence of recombinant proinsulin GR3RR in the above way, the following primers for a point mutagenesis reaction were designed:

```
THRG
5' TACTGCAATACTTAAGTCGACTCTAGC 3'
          ThrSTOP

THRD
5' AGAGTCGACTTAAGTATTGCAGTAGTT 3'
              Thr
```

The point mutagenesis reaction was carried out using the Stratagene kit (cat. No. 200518-5). Isolation and verification of correctness of the plasmid nucleotide sequence, and obtaining *E. coli* DH5α bacteria with the p5/ZUINSThr (22A)Arg(3B)Arg(31B)Arg(32B) plasmid, were carried out as in Example 1.

Example 9

Construction of
p6/ZUINSSer(22A)Lys(3B)Arg(31B)Arg(32B)
Plasmid and Obtaining a Strain Transformed with it In order to obtain a gene of recombinant proinsulin SK3RR, p6/ZUINSSer(22A)Arg(31B)Arg(32B) plasmid was used, which codes the recombinant proinsulin SRR and is described in patent application No. WO 2010/002283 A2, Example 6. The gene of recombinant proinsulin is—similarly to the p5 vector (Example 1)—attached to a modified gene of synthetic ubiquitin and contains a gene of tetracycline resistance. The region coding the modified fusion protein is placed under the control of a pms promoter (patent application No. WO 05066344 A2).

The recombinant proinsulin SK3RR gene differs from the initial proinsulin SRR gene by the fact that the AAC codon (Asn) is replaced with an AAA codon for lysine (Lys) in position 3 of chain B. In order to modify the gene of the coding sequence of recombinant proinsulin SRR in the above way, the following primers for a point mutagenesis reaction were designed:

```
KSRL
5' GGTGGTCGTTTTGTCAAACAGCAC 3'
                    Lys

KSRP
5' ACCACACAGGTGCTGTTTGACAAA 3'
                    Lys
```

Utilising plasmid DNA p6/ZUINSSer(22A)Arg(31B)Arg (32B) as a template, the point mutagenesis reaction was carried out using a kit from Stratagene (cat. No. 200518-5). By known methods, the reaction mixture was used to transform competent cells of *Escherichia coli* DH5α. The plasmid was isolated and sequenced in order to verify the presence of AAA nucleotides coding lysine and the correctness of the plasmid sequence. The obtained p6/ZUINSSer (22A)Lys(3B)Arg(31B)Arg(32B) plasmid with the recombinant proinsulin SK3RR gene was used to transform competent cells of *E. coli* DH5α, and a bacterial culture was made on an LB nutrient medium with the addition of tetracycline (0.01 mg/ml) in a volume of 500 ml, at 37° C., 200 rpm, for 18 hours. The bacterial material for the strain bank was prepared, and samples with a 1:1 ratio of the bacterial culture to 40% glycerol were deposited at −70° C.

Genetic Construction of p6/ZUINSSer(22A)Lys(3B)Arg(31B)Arg(32B) Plasmid

The p6/ZUINSSer(22A)Lys(3B)Arg(31B)Arg(32B) plasmid comprising 4911 base pairs is composed of the following regulator sequences and genes:
- from 146 bp to 1336 bp, the tetracycline resistance gene TET R is located,
- from 4304 bp to 4469 bp, the region coding pms promoter is located,
- from 4473 bp to 4703 bp, the sequence coding the modified gene of synthetic ubiquitin ZUBI is included,
- from 4704 bp to 4868 bp, the sequence coding the gene of proinsulin SK3RR is located,
- from 4875 bp to 4911 bp, the region coding the transcription terminator Ter is located.

Figure 2:
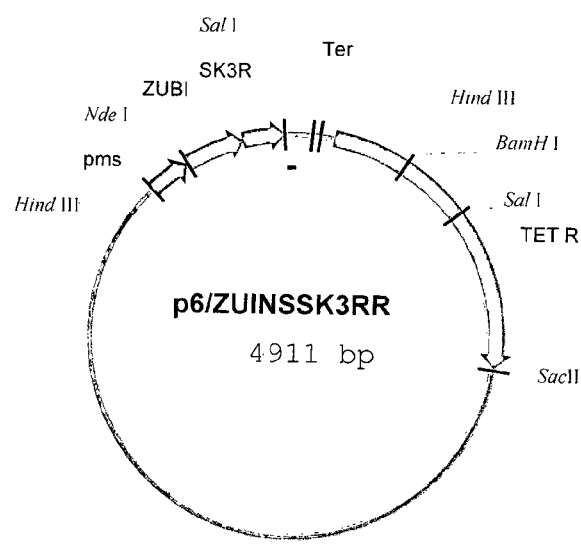
FIG. 2 shows the structure of the p6/ZUINSSer(22A)Lys(3B)Arg(31B)Arg(32B) plasmid containing a gene coding the recombinant proinsulin SK3RR.

The structure of the p6/ZUINSSer(22A)Lys(3B)Arg(31B)Arg(32B) plasmid, containing the gene coding the recombinant proinsulin SK3RR, is shown schematically in FIG. 2, and its nucleotide and amino acid sequences as SEQ. No. 24.

Example 10

Construction of p6/ZUINSSer(22A)Lys(3B)Arg(31B) Plasmid and Obtaining a Strain Transformed with it In order to obtain the gene of recombinant proinsulin SK3R with only one arginine residue at the end of chain B, a p6/ZUINSSer(22A)Lys(3B)Arg(31B)Arg(32B) plasmid was used, coding the recombinant proinsulin SK3RR.

The recombinant proinsulin SK3R gene differs from the initial proinsulin SK3RR gene by deletion of the CGC codon (Arg) in position 32 of chain B. In order to modify the gene of the coding sequence of recombinant proinsulin SK3RR in the above way, the following primers for a point mutagenesis reaction were designed:

```
SARGL
5' ACTCCTAAAACACGTGGCATCGTT 3'

SARGP
5' AACGATGCCACGTGTTTTAGGAGT 3'
```

Utilising plasmid DNA p6/ZUINSSer(22A)Lys(3B)Arg(31B)Arg(32B) as a template, the point mutagenesis reaction was carried out using a kit from Stratagene (cat. No. 200518-5).

By known methods, the reaction mixture was used to transform competent cells of *Escherichia coli* DH5α. The plasmid was isolated and sequenced in order to verify the deletion of CGC nucleotides coding arginine and correctness of the plasmid sequence. The obtaining of *E. coli* DH5α bacteria with the p6/ZUINSSer(22A)Lys(3B)Arg(31B) plasmid was carried out as in Example 1.

Example 11

Production of Insulin GK3R

Insulin GK3R was produced in a biosynthesis process carried out in a classical way (inoculum, inoculation culture, production culture) using an *Escherichia coli* strain which contained a DNA fragment coding the recombinant proinsulin GK3RR, constructed according to Example 2. The production culture was carried out in a 150 dm³ fermenter for 20 hours at 37° C., while controlling pH, temperature, revolutions of the stirrer, optical density, glucose concentration and aeration. Under fermentation conditions, preproinsulin GK3RR was produced intracellularly in the form of inclusion bodies. After the end of the fermentation, the broth was cooled and concentrated, and the remaining biological material was washed out of the mineral substances included in the nutrient medium. It was then subjected to digestion with a lysozyme in a buffer with Triton. Then, a process of cell disintegration was carried out, and the generated suspension of inclusion bodies was centrifuged, washed and again centrifuged, eventually obtaining a homogenised precipitation of inclusion bodies containing preproinsulin GK3RR.

The obtained homogenate was dissolved (10-15 mg/cm³) in a sodium bicarbonate solution with the addition of EDTA and was subjected to renaturation and to reversible citraconylation in a reaction with citraconic anhydride for protection of lysine amine groups. The dissolved protein was subjected to digestion with trypsin in order to cut off the leader protein and dissect insulin chains. As a result of the trypsin action, insulin GK3R was obtained. The obtained protein in the solution was subjected to purification by low pressure liquid chromatography on a DEAE Sepharose FF gel, and then decitraconylation and precipitation of raw protein with the addition of zinc chloride were carried out. The raw insulin GK3R was subjected to purification by low pressure liquid chromatography on a Q Sepharose FF gel and next by high pressure liquid chromatography on a Kromasil RP C8 100A 13 µm gel. From the main fraction, purified insulin GK3R was separated as a successive result of: precipitation with the addition of zinc chloride, gel filtration on a Sephadex G-25 bed and final crystallisation using zinc acetate.

From one portion of inclusion bodies, about 5.4 g of crystalline insulin GK3R was obtained with the HPLC purity of 99%.

The structure of the product was confirmed by the following results:
- molecular mass determined by mass spectroscopy amounts to 6035 and is consistent with the theoretical value (6035.0);
- peptide map: consistent;
- amino acid sequence and composition: consistent with the theoretical values.

Example 12

Production of Insulin AK3R

Following an analogical procedure, as in Example 11, using an *Escherichia coli* strain containing a DNA fragment coding the insulin AK3R precursor, the fragment being constructed according to Example 3, 5.2 g of insulin AK3R with the HPLC purity of 98% was obtained from an analogous portion of inclusion bodies.

The structure of the product was confirmed by the following results:
- molecular mass determined by mass spectroscopy amounts to 6049 and is consistent with the theoretical value (6049.0);
- peptide map: consistent;
- amino acid sequence and composition: consistent with the theoretical values.

The isoelectric point, determined by capillary electrophoresis, amounts to 7.0.

Example 13

Production of Insulin SK3R

Following an analogical procedure, as in Example 11, using either an *Escherichia coli* strain containing a DNA fragment coding proinsulin SK3RR, the fragment being constructed according to Example 1 or Example 9, or an *Escherichia coli* strain containing a DNA fragment coding proinsulin SK3R, the fragment being constructed according to Example 10, 5.0-6.2 g of insulin SK3R with the HPLC purity of 99% were obtained from an analogous portion of inclusion bodies.

In each case, the structure of the product was confirmed by the following results:
molecular mass determined by mass spectroscopy amounts to 6065 and is consistent with the theoretical value (6065.0);
peptide map: consistent.

The isoelectric point, determined by capillary electrophoresis, amounts to 7.0.

Example 14

Production of Insulin SR3R

Insulin SR3R was produced in a biosynthesis process using an *Escherichia coli* strain which contained a DNA fragment coding proinsulin SR3RR, constructed according to Example 7. The biosynthesis process was carried out in a 150 dm$^3$ fermenter, and the obtained biological material was processed using a procedure analogous to that described in Example 11. The obtained homogenate of inclusion bodies was subjected to controlled trypsinolysis in order to cut off the leader protein and dissect insulin chains.

All these operations, as well as purification in the next steps, were carried out using a procedure similar to that described in Example 11.

3.5 g of insulin SR3R with the HPLC purity of 97% was obtained from an analogous portion of inclusion bodies.

The structure of the product was confirmed by the following results:
molecular mass determined by mass spectroscopy amounts to 6094 (while the theoretical value amounts to 6093.0);
peptide map: consistent.

Example 15

Production of Pharmaceutical Product—Insulin SK3R Solution (100 U/ml)

100 ml of the pharmaceutical product—insulin SK3R solution (100 U/ml) was made with the following composition, per 1.0 ml of the finished product:

| | |
|---|---|
| insulin SK3R (Example 13) | 3.64 mg/ml (100 U/ml); |
| m-cresol | 2.7 mg/ml; |
| anhydrous glycerol | 16.0 mg/ml; |
| zinc | 30.0 µg/ml; |
| water for injection | up to 1.0 ml. |
| pH | 4.0 |

The obtained mixture was filtered under sterile conditions through a 0.22 µm filter and dispensed into 3 ml cartridges.

It was found that the pharmaceutical product—insulin SK3R solution (100 U/ml) is stable in a test of accelerated stability (Example 19).

Example 16

Production of Pharmaceutical Product—Insulin SK3R Solution (100 U/ml)

100 ml of the pharmaceutical product—insulin SK3R solution (100 U/ml) was made with the following composition, per 1.0 ml of the finished product:

| | |
|---|---|
| insulin SK3R (Example 13) | 3.64 mg/ml (100 U/ml); |
| m-cresol | 2.7 mg/ml; |
| anhydrous glycerol | 16.0 mg/ml; |
| zinc | 11.0 µg/ml; |
| water for injection | up to 1.0 ml. |
| pH | 4.0 |

The obtained mixture was filtered under sterile conditions through a 0.22 µm filter and dispensed into 3 ml cartridges.

Example 17

Production of Pharmaceutical Product—Insulin SK3R Solution (100 U/ml)

100 ml of the pharmaceutical product—insulin SK3R solution (100 U/ml) was made with the following composition, per 1.0 ml of the finished product:

| | |
|---|---|
| insulin SK3R (Example 13) | 3.64 mg/ml (100 U/ml); |
| m-cresol | 2.7 mg/ml; |
| anhydrous glycerol | 16.0 mg/ml; |
| zinc | 11.0 µg/ml; |
| polisorbate 20 | 20.0 mg/ml; |
| water for injection | up to 1.0 ml. |
| pH | 4.0 |

The obtained mixture was filtered under sterile conditions through a 0.22 µm filter and dispensed into 3 ml cartridges.

Example 18

Production of Pharmaceutical Product—Insulin AK3R Solution (100 U/ml)

100 ml of the pharmaceutical product—insulin AK3R solution (100 U/ml) was made with the following composition, per 1.0 ml of the finished product:

| | |
|---|---|
| insulin AK3R (Example 12) | 3.63 mg/ml (100 U/ml); |
| m-cresol | 2.7 mg/ml; |
| anhydrous glycerol | 16.0 mg/ml; |
| zinc | 30.0 µg/ml; |
| water for injection | up to 1.0 ml. |
| pH | 4.0 |

The procedure was identical to that in Example 15, but insulin AK3R (in an amount of 363 mg, 10000 U) was used instead of insulin SK3R.

It was found that the pharmaceutical product—insulin AK3R solution (100 U/ml) is stable in a test of accelerated stability (Example 19).

Example 19

Study of the Long-Term Stability of Pharmaceutical Products: Insulin SK3R Solution (100 U/ml) and Insulin AK3R Solution (100 U/ml)

Insulin SK3R solution (100 U/ml) and insulin AK3R solution (100 U/ml) pharmaceutical products, made according to Examples 15 and 18, respectively, were subjected to a long-term stability test.

Figure 15:
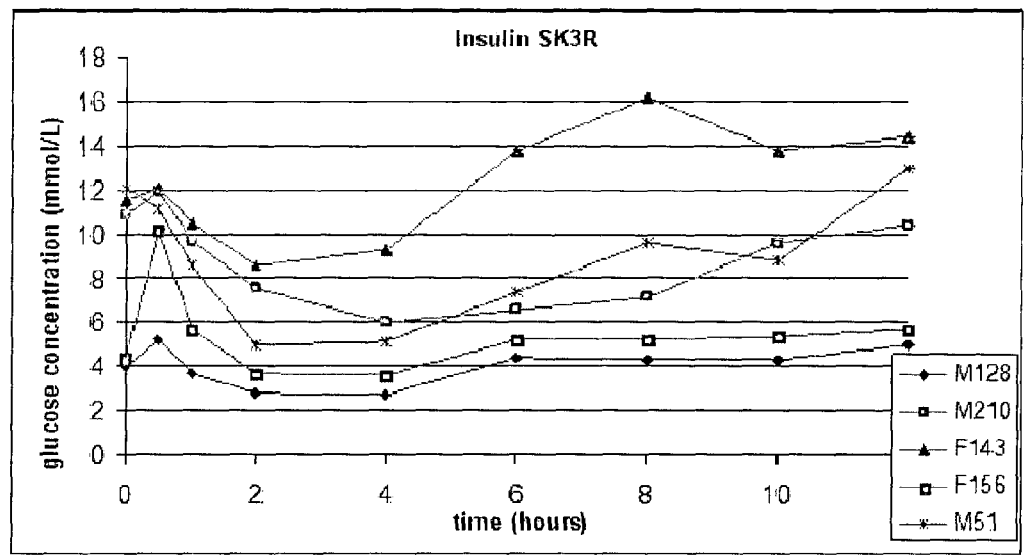
FIG. 15 shows the results of chemical stability (measured as a change in contents of related proteins) for pharmaceutical products insulin AK3R and insulin SK3R in comparison to human insulin and selected known long-acting analogues: lizarg insulin (WO 2006/096079 A2) and insulin GR (WO 2010/002283 A2)
Figure 15:
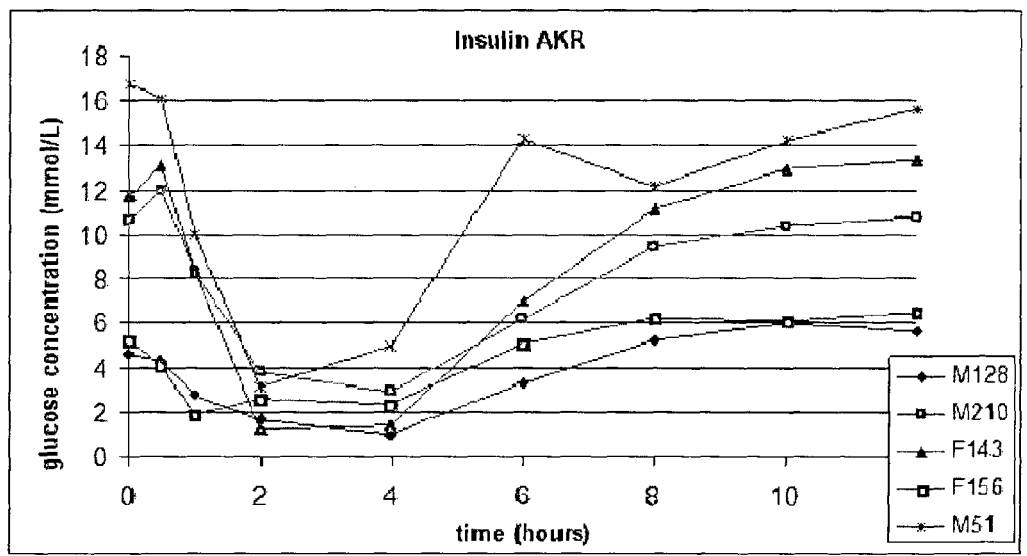

During the study of long-term stability, the contents of related proteins, the active substance and covalent polymers were analysed. Any change in these parameters is a measure of the chemical stability of a protein. In FIG. 15, a change in the contents of related proteins is shown for insulin AK3R and insulin SK3R pharmaceutical products in comparison to human insulin and other selected long-acting analogues, being subjects of applications Nos. WO 2006/096079 A2 and WO 2010/002283 A2.

Example 20

Investigation of the Activity of Insulin SK3R on Animals with Experimental Diabetes Results of the studies on an experimental diabetes model in WAG rats (induction with streptozotocin in a dose of 38 mg/kg bw.) undeniably confirmed the hypoglycaemic action of insulin SK3R. This action has distinct features of prolonged action. Studies included a group of 109 WAG strain rats in total.

After single administration of the SK3R analogue, the glucose concentration in the blood of rats decreases gradually to an almost normoglycaemic values (about 100 mg/dl), irrespective of the dose (doses tested: 2.5, 5 and 7.5 U/kg bw.). The average time of the maximum effect indicates a prolonged absorption from the site of administration. The maximum hypoglycaemic action occurs from 1 to 6 hours after administering the analogue. The course of the curve in this time exhibits a plateau characteristic for peakless insulin preparations. The glucose concentration then increases gradually, reaching the initial values after 24 hours.

Long-acting insulin glargine (Lantus preparation) was a reference preparation in the studies. The ascertained statistically relevant (Newman-Keuls, $\alpha=0.05$) differences in the courses of glycaemia profiles after single administration of insulin SK3R and insulin glargine prove slightly different pharmacodynamic profiles of both insulins—the profile of the SK3R analogue has a more flat and gentle course. After repeated administration (2 times per day in a dose of 5 U/kg bw. for 28 days), insulin SK3R causes a constant decrease in the glucose concentration in blood. This action is stable, being considerably different from the action of the reference preparation—insulin glargine. This is also proven by the average value of the coefficient of variation CV % of successive concentrations in profiles between the $14^{th}$ and $28^{th}$ day of the study (i.e. after achieving a stable effect), amounting to 11.3% for the SK3R analogue and 21.1% for insulin glargine. The action of insulin SK3R is also considerably stronger (statistically confirmed: Newman-Keuls, $\alpha=0.05$), which may suggest a higher level of activity of this insulin in comparison with insulin glargine.

A 12-hour glycaemic profile determined after 2 and 4 weeks of repeated administration proved that the hypoglycaemic curve in all time points (0.5-12 hours) has a similar course, irrespective of the study day. These observations confirm the thesis on the even and unusually stable hypoglycaemising effect of insulin SK3R, which ensures the maintaining of its constant level in an organism during prolonged therapy. It is a feature that differentiates it distinctly from insulin glargine, in comparison to which the studies have been carried out (ascertained statistical relevance in the majority of studied points, $\alpha=0.05$).

Differences in profiles of action similar to those described above may be noticed while comparing the result of insulin SK3R studies with preliminary results of insulin GEKR studies (an exponent of the group of compounds included in patent application No. WO 2010/002283 A2, which do not have a Lys basic amino acid in position B3). Basing on these comparisons, one may ascertain that inserting the Lys amino acid in position B3 completely cancels the strong and very rapid effect component (characterising the entire group of these compounds), distinctly extends the duration of pharmacological effect and makes it unusual even during prolonged therapy.

Based on the results shown, one may ascertain that the SK3R analogue has the properties of peakless, long-acting insulins and may have therapeutic use as a basis insulin administered once per day. At the same time, insulin SK3R differs from the commercially available equivalents by a significantly better, stable and even hypoglycaemic profile. Such an even level of insulin concentration during the day, simulating endogenous constant secretion from the pancreas, is particularly desirable in the treatment of diabetes. It is probable that the higher biological activity of the SK3R analogue may enable the decrease of insulin doses used to obtain the expected effect, not only decreasing the risk of a dose-dependent undesirable effect, but also being economically favourable.

The results showing the glucose concentration in the blood of rats after single administration of insulin SK3R in doses: 2.5 U/kg bw., 5 U/kg bw. and 7.5 U/kg bw., in the model of moderately severe streptozotocin diabetes, in comparison with insulin glargine (together with statistical evaluation), are shown in Table 1.

Figure 3:
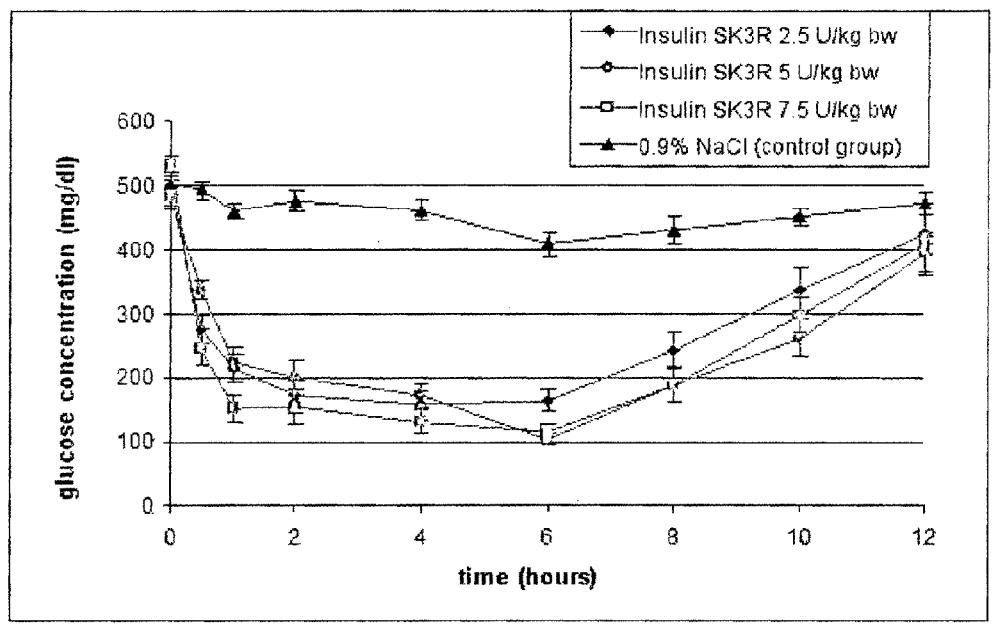
FIG. 3 shows a comprehensive graph illustrating a profile of the glucose concentration in the blood of rats, characteristic for peakless preparations, after single administration of insulin SK3R in doses: 2.5 U/kg bw., 5 U/kg bw. and 7.5 U/kg bw., in a model of moderately severe streptozocin diabetes. Average values±SEM.

A comprehensive graph illustrating a profile of glucose concentration in the blood of rats characteristic for peakless preparations after single administration of insulin SK3R in doses: 2.5 U/kg bw., 5 U/kg bw. and 7.5 U/kg bw., in the model of moderately severe streptozocin diabetes, is shown in FIG. 3.

Figure 4:
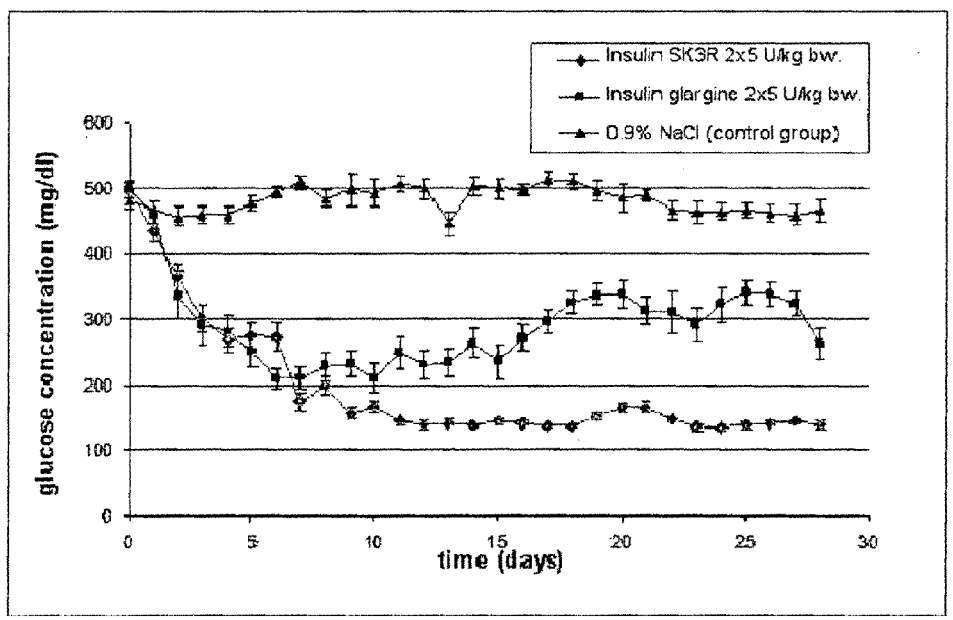
FIG. 4 shows a graph of the glucose concentration in the blood of rats after repeated (28 days) administration of insulin SK3R in a dose of 2×5 U/kg bw./day, in a model of moderately severe streptozocin diabetes, in comparison with insulin glargine and a control group. Average values±SEM.

The results illustrating glucose concentration in the blood of rats after repeated (28 days) administration of insulin SK3R in a dose of 2×5 U/kg bw./day, in the model of moderately severe streptozocin diabetes, in comparison with insulin glargine (together with statistical evaluation), are shown in Table 2 and in FIG. 4.

Figure 5:
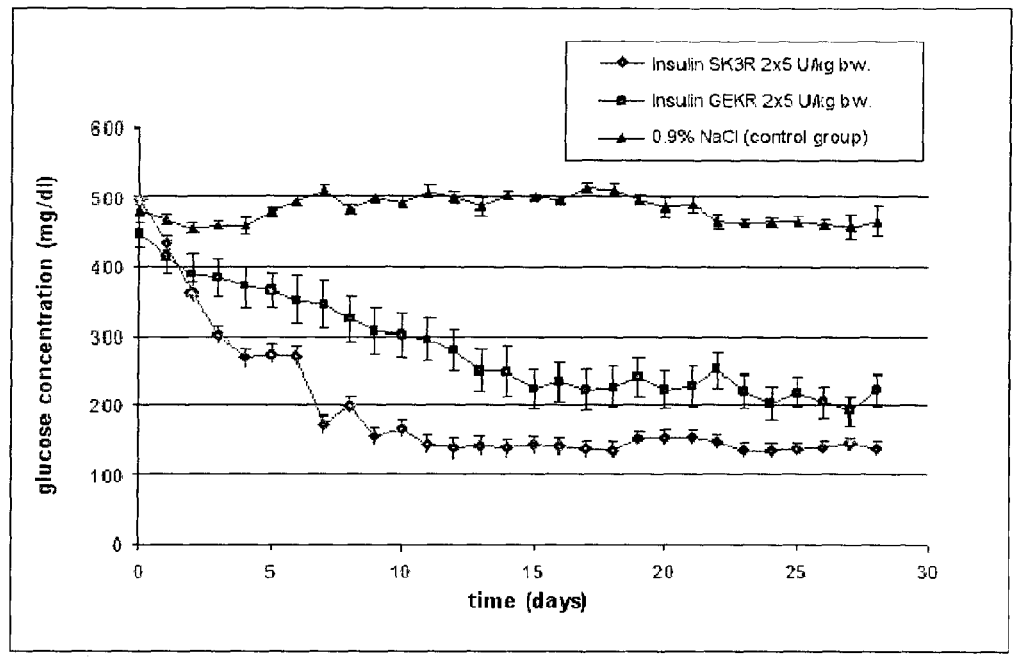
FIG. 5 shows a graph of the glucose concentration in the blood of rats after repeated (28 days) administration of insulin SK3R in a dose of 2×5 U/kg bw./day, in a model of moderately severe streptozocin diabetes, in comparison with insulin GEKR and a control group (preliminary results). Average values±SEM.

The results illustrating glucose concentration in the blood of rats after repeated (28 days) administration of insulin SK3R in a dose of 2×5 U/kg bw./day, in the model of moderately severe streptozocin diabetes, in comparison with insulin GEKR, are shown in Table 3 and in FIG. 5.

Figure 6:
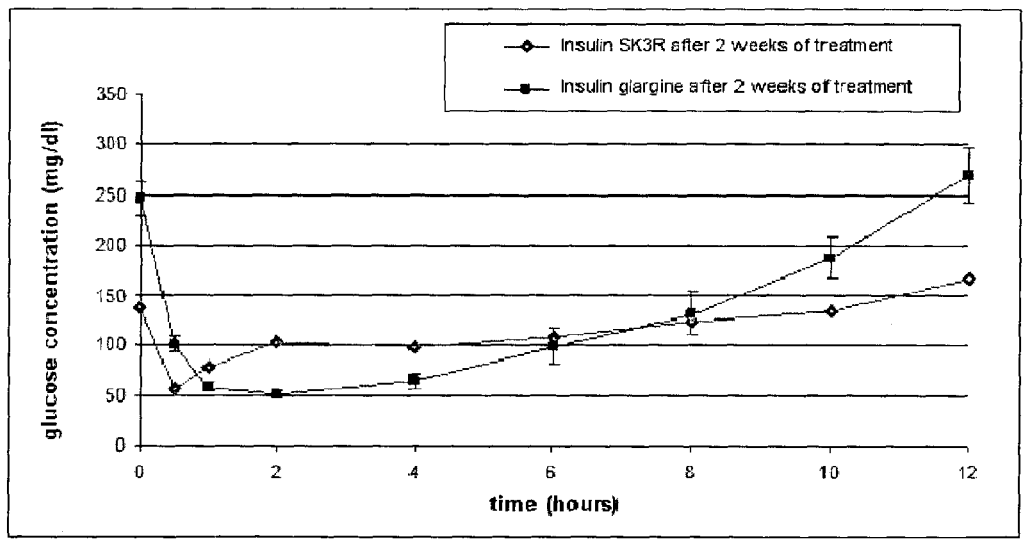
FIG. 6 shows a graph of 12-hour profiles of glucose concentration after 2 weeks of administration of insulin SK3R in a dose of 2×5 U/kg bw./day, in a model of moderately severe streptozocin diabetes, in comparison with insulin glargine. Average values±SEM.
Figure 7:
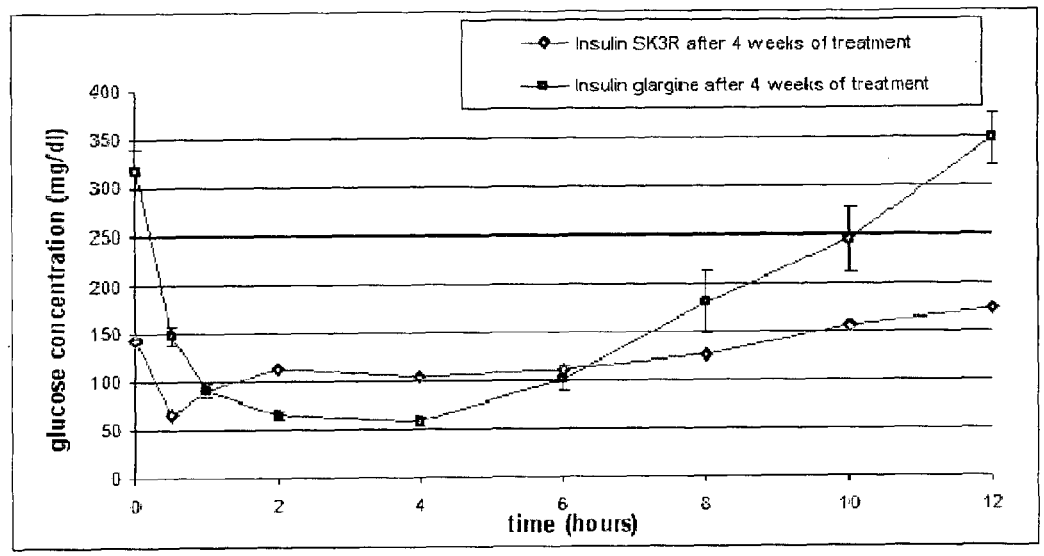
FIG. 7 shows a graph of 12-hour profiles of glucose concentration after 4 weeks of administration of insulin SK3R in a dose of 2×5 U/kg bw./day, in a model of moderately severe streptozocin diabetes, in comparison with insulin glargine. Average values±SEM.

The results illustrating 12-hour profiles of glucose concentration after 2 and 4 weeks of administration of insulin SK3R in a dose of 2×5 U/kg bw./day, in the model of moderately severe streptozocin diabetes, in comparison with insulin glargine (together with statistical evaluation), are shown in Table 4 and in FIGS. 6-7.

The results illustrating 12-hour profiles of glucose concentration after 1, 2 and 4 weeks of administration of insulin SK3R in a dose of 2×5 U/kg bw./day, in the model of moderately severe streptozocin diabetes, in comparison with insulin GEKR, are shown in Table 5.

Figure 8:
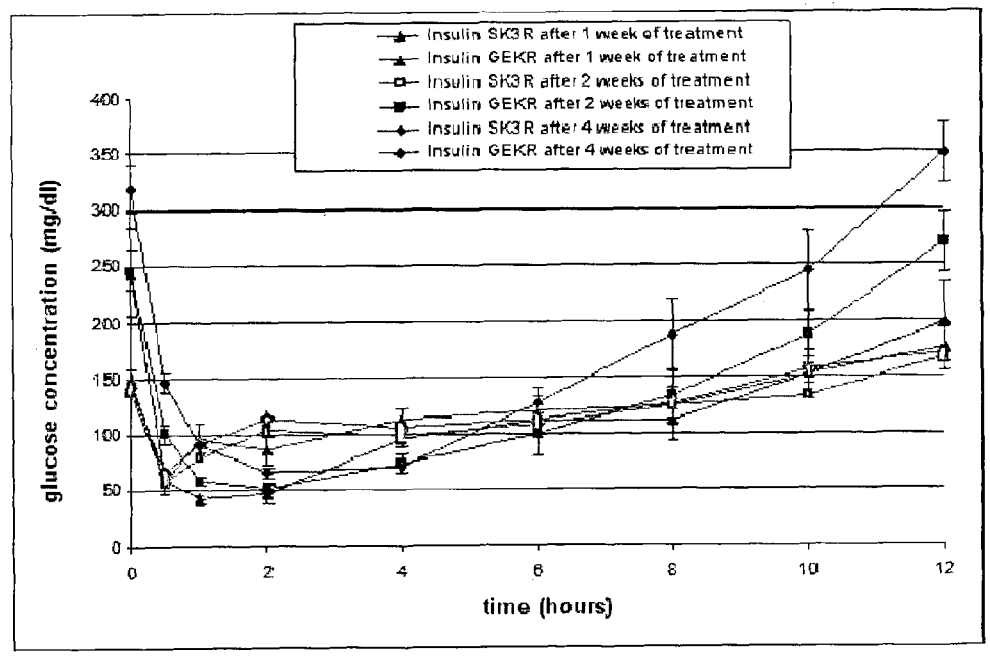
FIG. 8 shows a comprehensive graph of 12-hour profiles of glucose concentration after 1, 2 and 4 weeks of administration of insulin SK3R in a dose of 2×5 U/kg bw./day, in a model of moderately severe streptozocin diabetes, in comparison with insulin GEKR in a dose of 2×5 U/kg bw./day (preliminary results). Average values±SEM.

A comprehensive graph of 12-hour profiles of glucose concentration after 1, 2 and 4 weeks of administration of insulin SK3R in a dose of 2×5 U/kg bw./day, in a model of moderately severe streptozocin diabetes, in comparison with insulin GEKR, is shown in FIG. 8 (preliminary results).

TABLE 1

Glucose concentration in the blood of rats after single administration of insulin SK3R in doses: 2.5 U/kg bw., 5 U/kg bw. and 7.5 U/kg bw., in the model of moderately severe streptozotocin diabetes, in comparison with insulin glargine (together with statistical evaluation).

| | | | | | | glucose concentration in the blood of rats, average value (mg/dl) ± SEM | | | | |
|---|---|---|---|---|---|---|---|---|---|---|
| diabetes model | studied preparation | s.c. dose | number of rats in the group | normo-gly-caemia | chronic hypergly-caemia | time of blood sampling after single administration of the preparation hours | | | | |
| | | | | | 0 | 0.5 | 1 | 2 | 4 | |
| moderately severe (streptozotocin - 38 mg/kg bw., i.m.) | insulin SK3R | 2.5 U/kg bw. | 12 | 86.8 ± 1.0 | 489.6 ± 19.7 | 276.5 ± 21.5^ | 214.8 ± 21.9^ | 171.3 ± 25.9*^ | 156.4 ± 21.6^ | |
| | insulin glargine | | 7 | 84.6 ± 2.3 | 496.3 ± 33.3 | 299.9 ± 38.2 | 220.3 ± 23.5 | 71.6 ± 9.1 | 122.7 ± 31.8 | |
| | insulin SK3R | 5 U/kg bw. | 15 | 80.0 ± 1.4 | 480.3 ± 16.0 | 335.9 ± 15.5*^ | 224.7 ± 23.5^ | 200.7 ± 28.0*^ | 171.7 ± 17.9*^ | |
| | insulin glargine | | 7 | 78.3 ± 0.8 | 487.4 ± 17.8 | 412.9 ± 17.8 | 249.6 ± 35.8 | 98.1 ± 6.8 | 69.7 ± 5.6 | |
| | insulin SK3R | 7.5 U/kg bw. | 10 | 85.7 ± 1.5 | 531.1 ± 15.4 | 246.6 ± 27.7^ | 150.8 ± 20.5^ | 154.5 ± 28.6*^ | 131.5 ± 19.4^ | |
| | insulin glargine | | 7 | 81.3 ± 2.0 | 519.0 ± 26.0 | 303.0 ± 20.7 | 173.0 ± 10.6 | 69.3 ± 4.3 | 110.3 ± 5.0 | |
| | control | 30 μl/ 300 g bw. | 10 | 81.7 ± 1.8 | 502.9 ± 18.0 | 493.6 ± 13.4 | 460.6 ± 12.2 | 475.6 ± 15.7 | 461.6 ± 17.4 | |

| diabetes model | studied preparation | s.c. dose | number of rats in the group | glucose concentration in the blood of rats, average value (mg/dl) ± SEM time of blood sampling after single administration of the preparation hours | | | | |
|---|---|---|---|---|---|---|---|---|
| | | | | 6 | 8 | 10 | 12 | 24 |
| moderately severe (streptozotocin - 38 mg/kg bw., i.m.) | insulin SK3R | 2.5 U/kg bw. | 12 | 165.0 ± 16.5^ | 241.3 ± 28.6*^ | 337.3 ± 34.7*^ | 422.9 ± 32.1* | 462.6 ± 17.6 |
| | insulin glargine | | 7 | 234.6 ± 49.1 | 387.7 ± 45.9 | 464.6 ± 54.2 | 537.0 ± 156 | 506.3 ± 26.5 |
| | insulin SK3R | 5 U/kg bw. | 15 | 104.4 ± 7.9^ | 186.5 ± 26.9*^ | 261.3 ± 28.6^ | 393.9 ± 26.8^ | 476.2 ± 21.2 |
| | insulin glargine | | 7 | 93.6 ± 13.4 | 86.0 ± 10.2 | 207.9 ± 27.0 | 352.3 ± 29.8 | 438.4 ± 17.6 |
| | insulin SK3R | 7.5 U/kg bw. | 10 | 116.5 ± 11.2^ | 188.1 ± 27.6^ | 296.5 ± 37.7*^ | 408.5 ± 47.5 | 427.3 ± 37.3 |
| | insulin glargine | | 7 | 128.1 ± 9.2 | 167.7 ± 8.4 | 191.0 ± 7.3 | 458.0 ± 23.4 | 482.0 ± 27.4 |
| | control | 30 μl/ 300 g bw. | 10 | 407.7 ± 19.2 | 430.1 ± 22.4 | 450.3 ± 12.7 | 472.2 ± 17.1 | 513.7 ± 17.0 |

Significance level (Newman-Keuls test):
*p < 0.05 insulin SK3R vs. insulin glargine
^p < 0.05 insulin SK3R vs. control

TABLE 2

Glucose concentration in the blood of rats after repeated (28 days) administration of insulin SK3R in a dose of 2 × 5 U/kg bw./day, in the model of moderately severe streptozocin diabetes, in comparison with insulin glargine (together with statistical evaluation).

| | | | | glucose concentration in the blood of rats, average value (mg/dl) ± SEM | | | | | | |
|---|---|---|---|---|---|---|---|---|---|---|
| studied preparation | number of rats in the group | normo-gly-caemia | chronic hypergly-caemia | successive days of the study | | | | | | |
| | | | | 1 | 2 | 3 | 4 | 5 | 6 | 7 |
| insulin SK3R 2 × 5 U/kg bw./day | 21 | 79.9 ± 0.9 | 496.3 ± 11.5 | 433.9 ± 14.0 | 363.6 ± 21.1^ | 301.8 ± 20.5^ | 2684 ± 19.1^ | 273.4 ± 20.0^ | 272.0 ± 21.9*^ | 173.4 ± 13.7^ |
| insulin glargine 2 × 5 U/kg bw./day | 12 | 82.7 ± 1.4 | 497.8 ± 13.0 | 458.8 ± 20.4 | 336.2 ± 35.6 | 292.4 ± 30.2 | 281.5 ± 23.0 | 250.3 ± 24.2 | 209.3 ± 14.9 | 210.7 ± 17.9 |

TABLE 2-continued

Glucose concentration in the blood of rats after repeated (28 days) administration of insulin SK3R in a dose of 2 × 5 U/kg bw./day, in the model of moderately severe streptozocin diabetes, in comparison with insulin glargine (together with statistical evaluation).

| | | | | | | | | | |
|---|---|---|---|---|---|---|---|---|---|
| control 30 μl/300 g bw./day | 8 | 81.5 ± 1.8 | 480.9 ± 13.6 | 468.4 ± 10.4 | 455.6 ± 13.8 | 459.3 ± 12.5 | 458.9 ± 11.5 | 477.5 ± 10.8 | 493.4 ± 8.6 | 507.8 ± 12.3 |

| studied preparation | number of rats in the group | glucose concentration in the blood of rats, average value (mg/dl) ± SEM successive days of the study | | | | | | |
|---|---|---|---|---|---|---|---|---|
| | | 8 | 9 | 10 | 11 | 12 | 13 | 14 |
| insulin SK3R 2 × 5 U/kg bw./day | 21 | 198.9 ± 13.7^ | 155.5 ± 8.4*^ | 166.2 ± 9.0*^ | 143.6 ± 4.4*^ | 138.2 ± 5.4*^ | 141.3 ± 5.3*^ | 137.9 ± 2.7*^ |
| insulin glargine 2 × 5 U/kg bw./day | 12 | 226.8 ± 22.5 | 232.8 ± 20.9 | 209.4 ± 22.6 | 248.0 ± 25.2 | 230.0 ± 22.6 | 233.7 ± 21.9 | 262.7 ± 22.7 |
| control 30 μl/300 g bw./day | 8 | 482.6 ± 12.3 | 497.5 ± 25.3 | 491.8 ± 20.0 | 506.4 ± 13.2 | 499.4 ± 15.7 | 446.3 ± 18.0 | 502.6 ± 15.4 |

| studied preparation | number of rats in the group | normo- gly- caemia | chronic hypergly- caemia | successive days of the study | | | | | | |
|---|---|---|---|---|---|---|---|---|---|---|
| | | | | 15 | 16 | 17 | 18 | 19 | 20 | 21 |
| insulin SK3R 2 × 5 U/kg bw./day | 21 | 79.9 ± 0.9 | 496.3 ± 11.5 | 143.9 ± 4.7*^ | 140.8 ± 3.2*^ | 136.3 ± 2.0*^ | 135.4 ± 2.1*^ | 151.2 ± 6.1*^ | 163.7 ± 6.7*^ | 164.2 ± 7.8*^ |
| insulin glargine 2 × 5 U/kg bw./day | 12 | 82.7 ± 1.4 | 497.8 ± 13.0 | 235.7 ± 26.4 | 271.1 ± 19.8 | 296.6 ± 17.3 | 325.4 ± 17.5 | 336.9 ± 16.4 | 338.3 ± 21.1 | 312.0 ± 21.5 |
| control 30 μl/300 g bw./day | 8 | 81.5 ± 1.8 | 480.9 ± 13.6 | 499.5 ± 16.2 | 496.3 ± 8.7 | 513.3 ± 12.3 | 510.3 ± 12.1 | 496.0 ± 15.2 | 485.4 ± 22.0 | 488.8 ± 8.1 |

| studied preparation | number of rats in the group | successive days of the study | | | | | | |
|---|---|---|---|---|---|---|---|---|
| | | 22 | 23 | 24 | 25 | 26 | 27 | 28 |
| insulin SK3R 2 × 5 U/kg bw./day | 21 | 146.6 ± 3.3*^ | 135.2 ± 4.8*^ | 134.3 ± 4.8*^ | 137.3 ± 6.0*^ | 139.9 ± 4.7*^ | 144.2 ± 3.0*^ | 137.6 ± 6.3*^ |
| insulin glargine 2 × 5 U/kg bw./day | 12 | 310.5 ± 32.6 | 291.0 ± 25.2 | 322.8 ± 26.6 | 340.3 ± 18.3 | 338.3 ± 18.4 | 324.0 ± 19.4 | 262.6 ± 23.7 |
| control 30 μl/300 g bw./day | 8 | 465.8 ± 13.5 | 463.8 ± 17.8 | 464.8 ± 12.6 | 466.0 ± 10.1 | 461.1 ± 12.5 | 458.0 ± 16.2 | 465.1 ± 16.9 |

Significance level:
*$p < 0.05$ insulin SK3R 2 × 5 U/kg bw./day vs. insulin glargine 2 × 5 U/kg bw./day
^$p < 0.05$ insulin SK3R 2 × 5 U/kg bw /day vs. control

TABLE 3

Glucose concentration in the blood of rats after repeated (28 days) administration of insulin SK3R in a dose of 2 × 5 U/kg bw./day, in the model of moderately severe streptozocin diabetes, in comparison with insulin GEKR (preliminary results).

| studied preparation | number of rats in the group | chronic hypergly- caemia | glucose concentration in the blood of rats, average value (mg/dl) ± SEM successive days of the study | | | | | | |
|---|---|---|---|---|---|---|---|---|---|
| | | | 1 | 2 | 3 | 4 | 5 | 6 | 7 |
| insulin SK3R 2 × 5 U | 21 | 496.3 ± 11.5 | 433.9 ± 14.0 | 363.6 ± 21.1 | 301.8 ± 20.5 | 268.4 ± 19.1 | 273.4 ± 20.0 | 272.0 ± 21.9 | 173.4 ± 13.7 |

TABLE 3-continued

Glucose concentration in the blood of rats after repeated (28 days) administration of insulin SK3R in a dose of 2 × 5 U/kg bw./day, in the model of moderately severe streptozocin diabetes, in comparison with insulin GEKR (preliminary results).

| | | | | | | | | | |
|---|---|---|---|---|---|---|---|---|---|
| insulin GEKR 2 × 5 U | 8 | 445.3 ± 17.2 | 414.5 ± 23.4 | 388.9 ± 29.6 | 384.4 ± 26.7 | 370.5 ± 28.7 | 364.6 ± 26.1 | 352.6 ± 34.1 | 345.4 ± 34.1 |
| control 0.9% NaCl | 8 | 480.9 ± 13.6 | 468.4 ± 10.4 | 455.6 ± 13.8 | 459.3 ± 12.5 | 458.9 ± 11.5 | 477.5 ± 10.8 | 493.4 ± 8.6 | 507.8 ± 12.3 |

| studied preparation | number of rats in the group | glucose concentration in the blood of rats, average value (mg/dl) ± SEM successive days of the study | | | | | | |
|---|---|---|---|---|---|---|---|---|
| | | 8 | 9 | 10 | 11 | 12 | 13 | 14 |
| insulin SK3R 2 × 5 U | 21 | 198.9 ± 13.7 | 155.5 ± 8.4 | 166.2 ± 9.0 | 143.6 ± 4.4 | 138.2 ± 5.4 | 141.3 ± 5.3 | 137.9 ± 2.7 |
| insulin GEKR 2 × 5 U | 8 | 324.7 ± 33.6 | 308.4 ± 34.2 | 300.7 ± 32.3 | 295.2 ± 31.1 | 279.2 ± 29.3 | 250.9 ± 30.9 | 248.2 ± 37.7 |
| control 0.9% NaCl | 8 | 482.6 ± 12.3 | 497.5 ± 25.3 | 491.8 ± 20.0 | 506.4 ± 13.2 | 499.4 ± 15.7 | 446.3 ± 18.0 | 502.6 ± 15.4 |

| studied preparation | number of rats in the group | chronic hypergly- caemia | successive days of the study | | | | | | |
|---|---|---|---|---|---|---|---|---|---|
| | | | 15 | 16 | 17 | 18 | 19 | 20 | 21 |
| insulin SK3R 2 × 5 U | 21 | 496.3 ± 11.5 | 143.9 ± 4.7*^ | 140.8 ± 3.2*^ | 136.3 ± 2.0*^ | 135.4 ± 2.1*^ | 151.2 ± 6.1*^ | 163.7 ± 6.7*^ | 164.2 ± 7.8*^ |
| insulin GEKR 2 × 5 U | 8 | 445.3 ± 17.2 | 234.8 ± 28.8 | 221.9 ± 28.8 | 226.6 ± 29.5 | 240.4 ± 28.9 | 221.1 ± 29.1 | 228.3 ± 27.8 | 251.1 ± 28.7 |
| control 0.9% NaCl | 8 | 480.9 ± 13.6 | 499.5 ± 16.2 | 496.3 ± 8.7 | 513.3 ± 12.3 | 510.3 ± 12.1 | 496.0 ± 15.2 | 485.4 ± 22.0 | 488.8 ± 8.1 |

| studied preparation | number of rats in the group | successive days of the study | | | | | | |
|---|---|---|---|---|---|---|---|
| | | 22 | 23 | 24 | 25 | 26 | 27 | 28 |
| insulin SK3R 2 × 5 U | 21 | 146.6 ± 3.3*^ | 135.2 ± 4.8*^ | 134.3 ± 4.8*^ | 137.3 ± 6.0*^ | 139.9 ± 4.7*^ | 144.2 ± 3.0*^ | 137.6 ± 6.3*^ |
| insulin GEKR 2 × 5 U | 8 | 220.7 ± 26.4 | 203.8 ± 25.8 | 218.8 ± 22.9 | 205.7 ± 22.2 | 192.3 ± 21.6 | 221.3 ± 21.0 | 223.6 ± 22.3 |
| control 0.9% NaCl | 8 | 465.8 ± 13.5 | 463.8 ± 17.8 | 464.8 ± 12.6 | 466.0 ± 10.1 | 461.1 ± 12.5 | 458.0 ± 16.2 | 465.1 ± 16.9 |

TABLE 4

Course of 12-hour profiles of glucose concentration after 2 and 4 weeks of repeated administration of insulin SK3R in a dose of 2 × 5 U/kg bw./day, in the model of moderately severe streptozocin diabetes, in comparison with insulin glargine (together with statistical evaluation).

| studied preparation | profile determination time | in the day of the study before administration of the preparation | glucose concentration in the blood of rats, average value (mg/dl) ± SEM time of blood sampling after administration of the preparation hours | | | | | | | |
|---|---|---|---|---|---|---|---|---|---|---|
| | | | 0.5 | 1 | 2 | 4 | 6 | 8 | 10 | 12 |
| insulin SK3R 2 × 5 U/kg bw./day | after 2$^{nd}$ week | 137.8 ± 3.0* | 56.8 ± 1.9* | 79.0 ± 3.8* | 103.8 ± 5.3* | 98.8 ± 5.1* | 108.7 ± 5.4 | 124.1 ± 4.4 | 133.5 ± 4.1* | 166.9 ± 3.5* |
| insulin glargine 2 × 5 U/kg bw./day | | 246.2 ± 17.1 | 101.0 ± 8.1 | 58.2 ± 4.4 | 51.1 ± 3.8 | 64.2 ± 7.5 | 99.3 ± 18.0 | 131.3 ± 21.2 | 187.5 ± 21.2 | 269.8 ± 27.3 |
| insulin SK3R 2 × 5 U/kg bw./day | after 4$^{th}$ week | 142.6 ± 2.8* | 65.8 ± 2.9* | 90.9 ± 3.8 | 113.8 ± 7.1* | 105.6 ± 6.8* | 112.7 ± 5.5 | 126.6 ± 5.3 | 156.7 ± 3.9* | 171.6 ± 4.3* |
| insulin glargine 2 × 5 U/kg bw./day | | 319.1 ± 20.5 | 146.8 ± 9.1 | 90.7 ± 6.7 | 65.4 ± 4.7 | 58.0 ± 3.9 | 101.7 ± 13.7 | 179.3 ± 31.9 | 244.6 ± 35.0 | 348.4 ± 26.0 |

Significance level:
*p < 0.05 insulin SK3R vs. insulin glargine

TABLE 5

Course of 12-hour profiles of glucose concentration after 1, 2, and 4 weeks of repeated administration of insulin SK3R in a dose of 2 × 5 U/kg bw./day, in the model of moderately severe streptozocin diabetes, in comparison with insulin GEKR (preliminary results).

| studied preparation | profile determination time | | in the day of the study before administration of the preparation | glucose concentration in the blood of rats, average value (mg/dl) ± SEM time of blood sampling after administration of the preparation hours | | | | | | | |
|---|---|---|---|---|---|---|---|---|---|---|---|
| | | | | 0.5 | 1 | 2 | 4 | 6 | 8 | 10 | 12 |
| insulin SK3R 2 × 5 U/kg bw./day | after 1$^{st}$ week | SEM | 492.8 36.7 | 149.3 8.4 | 57.3 10.5 | 95.8 13.8 | 86.3 12.4 | 112.8 10.7 | 120.8 12.5 | 125.0 16.0 | 152.3 8.8 |
| insulin GEKR 2 × 5 U/kg bw./day | | SEM | 474.0 28.0 | 244.3 39.2 | 58.3 1.8 | 42.7 2.4 | 47.3 8.2 | 95.7 8.1 | 111.0 14.9 | 112.0 18.4 | 151.7 21.7 |
| insulin SK3R 2 × 5 U/kg bw./day | after 2$^{nd}$ week | SEM | 479.3 10.7 | 137.8 3.0 | 56.8 1.9 | 79.0 3.8 | 103.8 5.3 | 98.8 5.1 | 108.7 5.4 | 124.1 4.4 | 133.5 4.1 |
| insulin GEKR 2 × 5 U/kg bw./day | | SEM | 480.8 13.2 | 246.2 17.1 | 101.0 8.1 | 58.2 4.4 | 51.1 3.8 | 73.9 7.5 | 99.3 18.0 | 133.9 21.2 | 187.5 21.2 |
| insulin SK3R 2 × 5 U/kg bw./day | after 4$^{th}$ week | SEM | 479.3 10.7 | 142.6 2.8 | 65.8 2.9 | 90.9 3.8 | 113.8 7.1 | 105.6 6.8 | 112.7 5.5 | 126.6 5.3 | 156.7 3.9 |
| insulin GEKR 2 × 5 U/kg bw./day | | SEM | 480.8 13.2 | 319.1 20.5 | 146.8 9.1 | 90.7 6.7 | 65.4 4.7 | 69.6 3.9 | 127.0 13.7 | 188.3 31.9 | 244.6 35.0 |

Example 21

Investigation of the Activity of Insulin AK3R on Animals with Experimental Diabetes The hypoglycaemic action of insulin AK3R was confirmed in studies on rats with moderately severe streptozotocin diabetes. The AK3R analogue was administered to WAG strain rats with diabetes induced experimentally by single or repeated administration of streptozotocin (once per day for 4 weeks). Insulin glargine (Lantus preparation) was the reference preparation; additionally, a placebo control was used (physiological salt solution without insulin). The tests were carried out on 110 rats in total.

In the group receiving a single dose of the studied analogue, a slow and gradual decrease in the glucose level in the blood of the investigated rats was observed, proving the slowed-down absorption of insulin AK3R from its administration point. Essentially, a similar profile of glycaemia changes to the one for insulin glargine was ascertained.

The hypoglycaemic action of insulin AK3R was most frequently observed for 1 to 8 hours, then the glucose concentration was increasing to its initial value. A significant decrease in glucose concentration after administration of insulin AK3R in a dose of 5 U/kg bw. lasted for up to even 12 hours.

The course of the glycaemia curve was flat, with no distinct maximum of activity. The reference preparation exhibited a distinct maximum hypoglycaemic action in the 4$^{th}$ hour after administration, irrespective of the dose. The duration of the effect for insulin glargine was shorter when compared to the AK3R analogue—it most frequently lasted for 2 to 6 hours after administration.

In comparison with both insulin glargine and compounds included in application No. WO 2010/002283 A2, insulin AK3R maintains a hypoglycaemic action distinctly longer, and its profile of action has a remarkably peakless character, particularly by not showing the strong and rapid pharmacological effect characteristic for the groups of compounds included in application No. WO 2010/002283 A2.

Repeated administration of insulin AK3R in a dose of 5 U/kg bw. caused a constant decrease in the glucose level as early as in the first day of treatment, and in the 4$^{th}$ week, the level reached values approx. 60% lower than the initial ones. This action is stable and similar to that of the reference preparation—insulin glargine; however, a tendency to more stable maintenance of glycaemia at a statistically lower level is noticed, particularly from the 14$^{th}$ day of therapy (Newman-Keuls, $\alpha$=0.05). After discontinuing the administration of both studied insulin types, the glucose concentration in the blood of rats increases gradually to the initial values.

The course of 24 hours profiles of glucose concentration in the blood of rats, determined after 2 and 4 weeks of administration of insulin AK3R and insulin glargine, confirms the uniform hypoglycaemic action of the studied insulin, as well as a statistically significant dissimilarity when compared to the reference preparation (Newman-Keuls, $\alpha$=0.05).

In studies of all doses, no changes in appearance and behaviour of the animals were observed. There were also no differences in the topical tolerance of both preparations (changes in the locations of subcutaneous injections). Macroscopic and microscopic analyses of the tissues of sampled organs exhibit no pathological changes for all groups of examined animals.

Basing on the results of the above studies, one may ascertain that the AK3R analogue has the properties of peakless long-acting insulins and may have therapeutic use as a base insulin administered once per day. At the same time, as with insulin SK3R, insulin AK3R exhibit an original (better than those for commercially available long-acting analogues), stable and even 24 hours hypoglycaemic profile during prolonged therapy, differing also from the analogues included in application No. WO 2010/002283 A2.

The results showing the glucose concentration in the blood of rats after single administration of insulin AK3R in doses: 2.5 U/kg bw., 5 U/kg bw. and 7.5 U/kg bw., in the model of moderately severe streptozotocin diabetes, in comparison with insulin glargine (together with statistical evaluation), are shown in Table 6.

Figure 9:
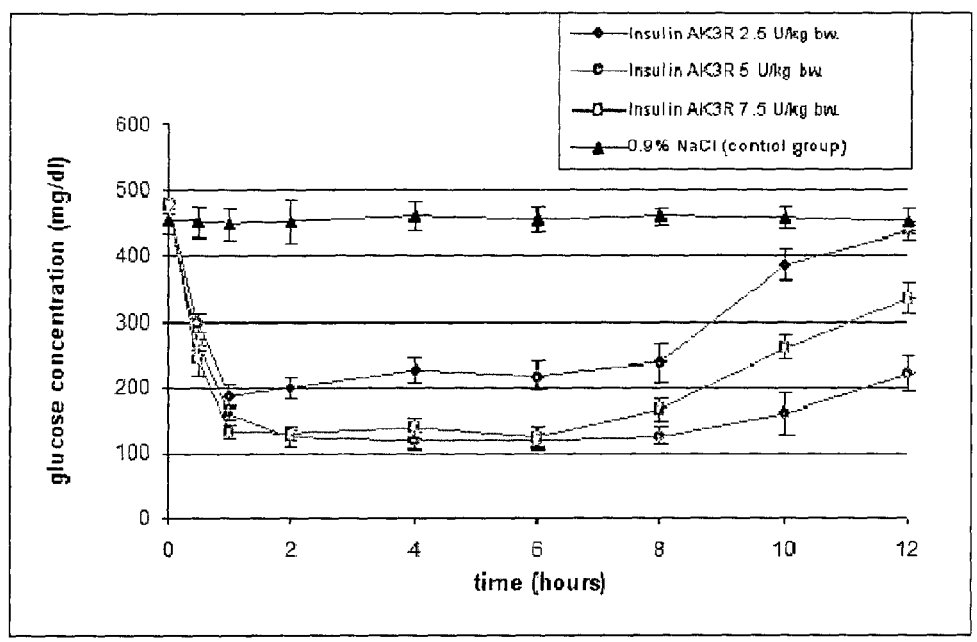
FIG. 9 shows a comprehensive graph illustrating a profile of the glucose concentration in the blood of rats characteristic for peakless preparations after single administration of insulin AK3R in doses: 2.5 U/kg bw., 5 U/kg bw. and 7.5 U/kg bw., in a model of moderately severe streptozocin diabetes. Average values±SEM.

A comprehensive graph illustrating a profile of the glucose concentration in the blood of rats characteristic for peakless preparations after single administration of insulin AK3R in doses: 2.5 U/kg bw., 5 U/kg bw. and 7.5 U/kg bw., in the model of moderately severe streptozocin diabetes, is shown in FIG. 9.

Figure 10:
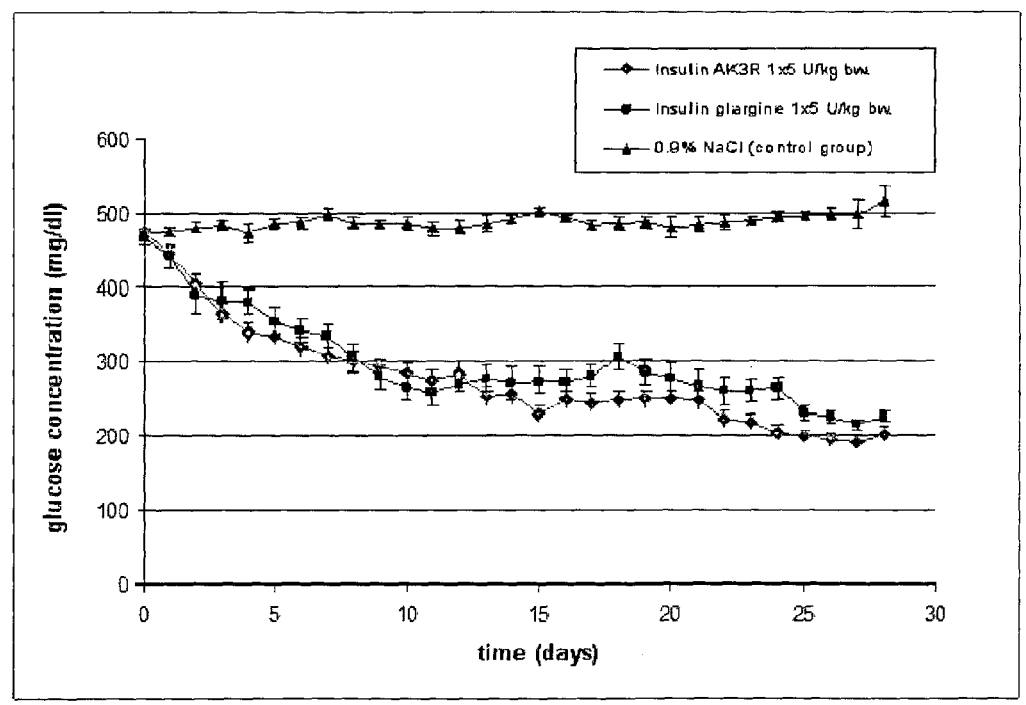
FIG. 10 shows a graph of the glucose concentration in the blood of rats after repeated (28 days) administration of insulin AK3R in a dose of 2×5 U/kg bw./day, in a model of moderately severe streptozocin diabetes, in comparison with insulin glargine and a control group. Average values±SEM.

The results illustrating glucose concentration in the blood of rats after repeated (28 days) administration of insulin AK3R in a dose of 1×5 U/kg bw./day, in the model of moderately severe streptozocin diabetes, in comparison with insulin glargine (together with statistical evaluation), are shown in Table 7 and in FIG. 10.

The results illustrating 12-hour profiles of glucose concentration after 2 and 4 weeks of administration of insulin AK3R in a dose of 1×5 U/kg bw./day, in the model of moderately severe streptozocin diabetes, in comparison with insulin glargine (together with statistical evaluation), are shown in Table 8.

Figure 11:
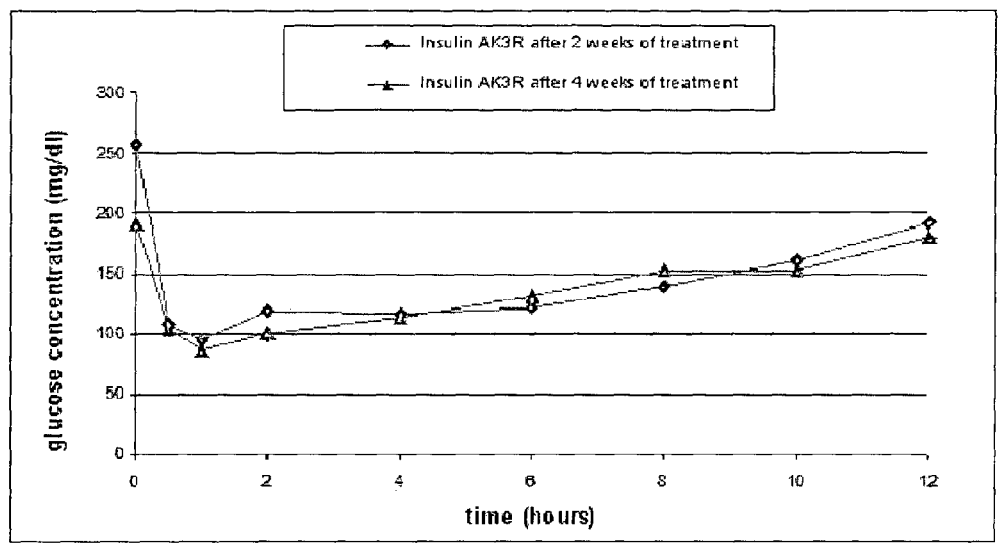
FIG. 11 shows a comprehensive graph of 12-hour profiles of glucose concentration after 2 and 4 weeks of administration of insulin AK3R in a dose of 1×5 U/kg bw./day, in a model of moderately severe streptozocin diabetes. Average values±SEM.

A comprehensive graph of 12-hour profiles of glucose concentration after 2 and 4 weeks of administration of insulin AK3R in a dose of 1×5 U/kg bw./day, in a model of moderately severe streptozocin diabetes, is shown in FIG. 11.

Figure 12:
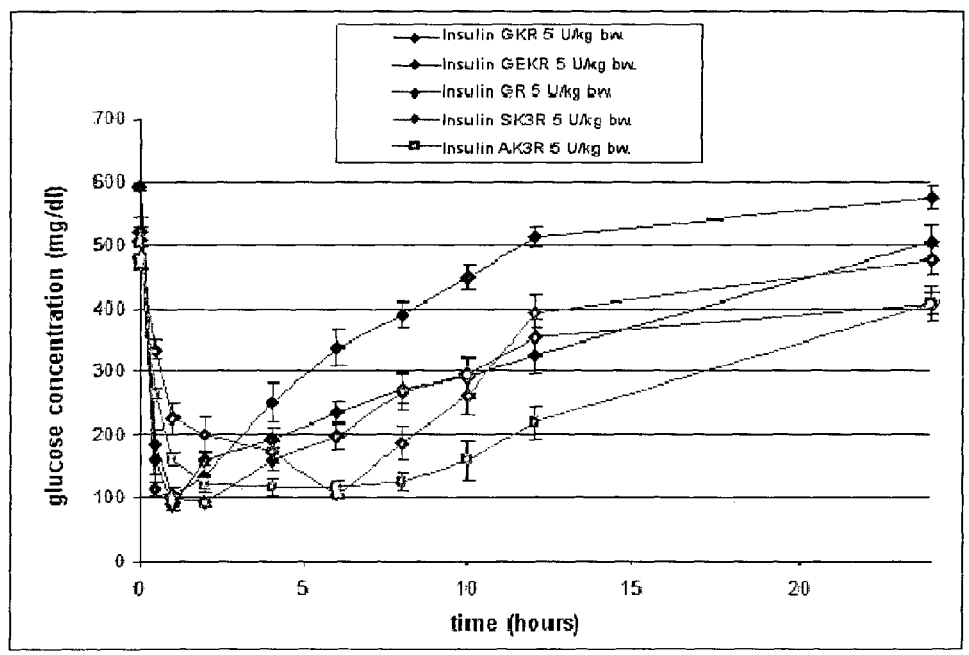
FIG. 12 shows a comparison of 24 hours profiles of glucose concentration after single administration of insulin GKR, insulin GEKR, insulin AKR, insulin GR and insulin SK3R and insulin AK3R in a dose of 1×5 U/kg bw., in a model of moderately severe streptozocin diabetes. Average values±SEM.

A comparison of the 24 hours profiles of glucose concentration after single administration of insulin GKR, insulin GEKR, insulin AKR, insulin GR and insulin SK3R and insulin AK3R in a dose of 1×5 U/kg bw. or 10 U/kg bw., in a model of moderately severe streptozocin diabetes, is shown in FIG. 12.

TABLE 6

Glucose concentration in the blood of rats after single administration of insulin AK3R in doses: 2.5 U/kg bw., 5 U/kg bw. and 7.5 U/kg bw., in the model of moderately severe streptozotocin diabetes, in comparison with insulin glargine (together with statistical evaluation).

| | | | | chronic | glucose concentration in the blood of rats, average value (mg/dl) ± SEM | | | | | | | | | | |
|---|---|---|---|---|---|---|---|---|---|---|---|---|---|---|---|
| studied prepara- tion | s.c. dose | number of rats in the group | normo- gly- caemia | hypergly- caemia | time of blood sampling after single administration of the preparation hours | | | | | | | | | | |
| | | | | 0 | 0.5 | 1 | 2 | 4 | 6 | 8 | 10 | 12 | 24 | 36 |
| insulin AK3R | 2.5 U/kg bw. | 12 | 78.9 ± 1.5 | 479.4 ± 6.8 | 298.0 ± 13.6*^ | 187.8 ± 17.3^ | 198.6 ± 16.0*^ | 226.7 ± 18.5*^ | 218.6 ± 21.1*^ | 237.5 ± 28.6^ | 386.8 ± 23.5^ | 436.2 ± 11.5 | 403.0 ± 13.7* | 444.1 ± 19.2 |
| Lantus | | 9 | 83.0 ± 1.2 | 465.3 ± 13.9 | 353.2 ± 16.0 | 198.0 ± 18.8 | 101.0 ± 10.6 | 88.2 ± 6.6 | 119.9 ± 9.2 | 191.7 ± 13.3 | 361.3 ± 15.3 | 446.8 ± 14.4 | 446.9 ± 14.2 | 460.7 ± 13.7 |
| insulin AK3R | 5 U/kg bw. | 12 | 81.8 ± 1.8 | 473.5 ± 8.0 | 264.8 ± 8.7*^ | 160.3 ± 9.3^ | 122.9 ± 13.4^ | 117.8 ± 13.4^ | 116.7 ± 12.9^ | 124.3 ± 13.9^ | 159.0 ± 31.4^ | 219.1 ± 27.3^ | 406.9 ± 16.2 | 448.0 ± 7.7^ |
| Lantus | | 9 | 84.1 ± 1.9 | 468.1 ± 14.4 | 321.8 ± 18.7 | 162.6 ± 18.2 | 107.4 ± 15.3 | 83.2 ± 6.5 | 108.6 ± 8.3 | 128.3 ± 6.9 | 166.6 ± 18.0 | 233.9 ± 36.3 | 435.3 ± 21.5 | 465.1 ± 14.5 |
| insulin AK3R | 7.5 U/kg bw. | 12 | 78.3 ± 2.2 | 479.8 ± 5.8 | 239.8 ± 21.9*^ | 131.3 ± 11.5*^ | 128.9 ± 10.0^ | 138.2 ± 17.1*^ | 12.35 ± 14.3^ | 165.3 ± 17.4^ | 259.9 ± 20.0*^ | 334.9 ± 23.4^ | 393.1 ± 28.1 | 418.8 ± 20.8 |
| Lantus | | 9 | 83.3 ± 1.8 | 477.3 ± 11.8 | 366.8 ± 31.4 | 247.1 ± 31.5 | 143.0 ± 13.7 | 83.2 ± 11.3 | 127.4 ± 15.7 | 162.7 ± 17.4 | 185.0 ± 14.2 | 346.0 ± 22.5 | 397.6 ± 21.3 | 447.3 ± 13.8 |
| control | 30 μl/300 g bw. | 6 | 84.2 ± 1.4 | 455.5 ± 25.4 | 452.5 ± 24.7 | 449.3 ± 24.7 | 453.3 ± 33.6 | 459.8 ± 23.8 | 455.3 ± 21.9 | 461.0 ± 13.6 | 458.3 ± 18.1 | 453.5 ± 21.3 | 460.2 ± 21.4 | 458.3 ± 22.5 |

Significance level:
*p < 0.05 insulin AK3R vs. insulin glargine
^p < 0.05 insulin AK3R vs. control

TABLE 7

Glucose concentration in the blood of rats after repeated (28 days) administration of insulin AK3R in a dose of 2 × 5 U/kg bw./day, in the model of moderately severe streptozocin diabetes, in comparison with insulin glargine (together with statistical evaluation).

| studied prepara- tion | number of rats in the group | normo- gly- caemia | chronic hypergly- caemia | glucose concentration in the blood of rats, average value (mg/dl) ± SEM | | | | | | |
|---|---|---|---|---|---|---|---|---|---|---|
| | | | | successive days of the study | | | | | | |
| | | | | 1 | 2 | 3 | 4 | 5 | 6 | 7 |
| insulin AK3R 5 U/kg bw./day | 24 | 81.0 ± 1.4 | 474.0 ± 5.3 | 444.4 ± 5.5 | 404.6 ± 14.3^ | 364.8 ± 12.3^ | 338.2 ± 14.3^ | 335.3 ± 13.9^ | 319.5 ± 13.4^ | 308.3 ± 12.4^ |
| Lantus 5 U/kg bw./day | 9 | 81.1 ± 1.8 | 466.2 ± 10.5 | 442.1 ± 15.4 | 391.0 ± 25.8 | 382.3 ± 24.6 | 380.2 ± 15.2 | 355.1 ± 17.8 | 342.2 ± 16.2 | 334.8 ± 15.1 |
| control 30 μl/300 g bw./day | 8 | 84.6 ± 2.7 | 472.3 ± 7.2 | 474.6 ± 6.9 | 480.1 ± 6.7 | 484.0 ± 5.3 | 473.6 ± 12.5 | 486.1 ± 5.8 | 486.8 ± 7.2 | 498.8 ± 8.2 |

| studied prepara- tion | number of rats in the group | glucose concentration in the blood of rats, average value (mg/dl) ± SEM | | | | | | |
|---|---|---|---|---|---|---|---|---|
| | | successive days of the study | | | | | | |
| | | 8 | 9 | 10 | 11 | 12 | 13 | 14 |
| insulin AK3R 5 U/kg bw./day | 24 | 301.9 ± 11.9^ | 291.9 ± 12.3^ | 285.0 ± 12.6^ | 275.2 ± 13.9^ | 284.3 ± 16.0^ | 253.2 ± 14.20^ | 257.2 ± 14.7^ |
| Lantus 5 U/kg bw./day | 9 | 306.1 ± 19.2 | 279.0 ± 16.5 | 264.4 ± 16.6 | 258.3 ± 19.3 | 268.3 ± 9.3 | 278.6 ± 16.9 | 270.8 ± 22.7 |

TABLE 7-continued

Glucose concentration in the blood of rats after repeated (28 days) administration of insulin AK3R in a dose of 2 × 5 U/kg bw./day, in the model of moderately severe streptozocin diabetes, in comparison with insulin glargine (together with statistical evaluation).

| | | | | | | | | | |
|---|---|---|---|---|---|---|---|---|---|
| control 30 μl/300 g bw./day | | 8 | 486.5 ± 6.7 | 485.1 ± 4.9 | 486.5 ± 8.5 | 478.6 ± 9.9 | 480.1 ± 9.0 | 485.3 ± 12.3 | 491.9 ± 6.3 |

| | | | | glucose concentration in the blood of rats, average value (mg/dl) ± SEM | | | | | |
|---|---|---|---|---|---|---|---|---|---|
| studied preparation | number of rats in the group | normo-gly-caemia | chronic hypergly-caemia | successive days of the study | | | | | |
| | | | | 15 | 16 | 17 | 18 | 19 | 20 | 21 |
| insulin AK3R 5 U/kg bw./day | 24 | 81.0 ± 1.4 | 474.0 ± 5.3 | 228.3 ± 12.7*^ | 248.0 ± 13.5^ | 244.0 ± 11.7^ | 248.3 ± 11.5*^ | 249.5 ± 11.2^ | 250.3 ± 11.2^ | 247.4 ± 11.3^ |
| Lantus 5 U/kg bw./day | 9 | 81.1 ± 1.8 | 466.2 ± 10.5 | 274.4 ± 18.9 | 273.9 ± 14.4 | 280.9 ± 14.1 | 305.4 ± 17.9 | 286.9 ± 17.1 | 278.2 ± 19.1 | 267.0 ± 20.5 |
| control 30 μl/300 g bw./day | 8 | 84.6 ± 2.7 | 472.3 ± 7.2 | 502.6 ± 4.0 | 493.0 ± 5.1 | 483.8 ± 6.9 | 485.3 ± 10.9 | 486.9 ± 7.7 | 479.8 ± 13.2 | 483.4 ± 10.2 |

| studied preparation | number of rats in the group | glucose concentration in the blood of rats, average value (mg/dl) ± SEM successive days of the study | | | | | | |
|---|---|---|---|---|---|---|---|---|
| | | 22 | 23 | 24 | 25 | 26 | 27 | 28 |
| insulin AK3R 5 U/kg bw./day | 24 | 222.2 ± 10.7^ | 217.6 ± 10.4*^ | 203.9 ± 11.3*^ | 198.5 ± 8.6*^ | 194.4 ± 9.6^ | 191.4 ± 9.9^ | 202.0 ± 10.1^ |
| Lantus 5 U/kg bw./day | 9 | 260.7 ± 18.6 | 260.7 ± 15.7 | 264.0 ± 15.7 | 231.8 ± 9.7 | 224.4 ± 8.9 | 215.3 ± 6.6 | 225.2 ± 7.4 |
| control 30 μl/300 g bw./day | 8 | 487.9 ± 10.0 | 490.4 ± 3.6 | 494.3 ± 7.3 | 496.1 ± 7.1 | 497.5 ± 8.8 | 497.4 ± 18.3 | 515.8 ± 20.1 |

Significance level:
*$p < 0.05$ insulin AK3R 5 U/kg bw./day vs. insulin glargine 5 U/kg bw./day
^$p < 0.05$ insulin AK3R 5 U/kg bw./day vs. control

TABLE 8

Course of 12-hour profiles of glucose concentration after 2 and 4 weeks of repeated administration of insulin AK3R in a dose of 1 × 5 U/kg bw./day, in the model of moderately severe streptozocin diabetes, in comparison with insulin glargine (together with statistical evaluation).

| | | | glucose concentration in the blood of rats, average value (mg/dl) ± SEM | | | | | | | |
|---|---|---|---|---|---|---|---|---|---|---|
| studied preparation | profile determination time | in the day of the study before administration of the preparation | time of blood sampling after administration of the preparation hours | | | | | | | |
| | | | 0.5 | 1 | 2 | 4 | 6 | 8 | 10 | 12 |
| insulin AK3R 5 U/kg bw./day | after 2$^{nd}$ week | 257.2 ± 14.7 | 108.4 ± 8.5 | 94.0 ± 7.3 | 119.0 ± 6.9* | 116.2 ± 3.8* | 121.2 ± 6.1 | 139.3 ± 6.3 | 160.5 ± 6.2* | 191.3 ± 8.5* |
| Lantus 5 U/kg bw./day | | 270.8 ± 22.7 | 120.1 ± 11.0 | 73.6 ± 4.6 | 69.3 ± 3.7 | 77.7 ± 7.9 | 129.7 ± 13.6 | 162.2 ± 12.2 | 200.0 ± 18.2 | 234.6 ± 20.3 |
| insulin AK3R 5 U/kg bw./day | after 4$^{th}$ week | 191.4 ± 9.9 | 103.8 ± 5.6 | 87.1 ± 4.4* | 99.5 ± 4.9* | 113.3 ± 4.9* | 131.2 ± 5.6* | 152.4 ± 5.7* | 152.7 ± 5.9 | 179.2 ± 6.5* |
| Lantus 5 U/kg bw./day | | 215.3 ± 6.6 | 107.0 ± 7.4 | 71.2 ± 3.6 | 63.4 ± 1.7 | 58.9 ± 1.9 | 65.6 ± 2.7 | 121.0 ± 15.7 | 150.4 ± 16.6 | 208.6 ± 4.9 |

Significance level:
*$p < 0.05$ insulin AK3R vs. insulin glargine

Example 22

Study of Insulin SK3R Activity on Primates

Comparative studies of insulin SK3R activity were carried out on monkeys of the genus Rhesus with chronic hypoglycaemia, constituting an experimental model of type 2 diabetes with primates. The results of the studies undeniably confirm the pharmaceutical activity of insulin SK3R and its properties observed earlier, including the characteristic shape of the glycaemia profile after application of the studied compound.

The hypoglycaemic activity of insulin SK3R was evaluated based on changes in values of glucose concentrations in time, in comparison with insulin AKR, being an exponent of compounds included in patent application No. WO 2010/002283 A2. 6 monkeys—3 males and 3 females—were subjected to the tests. The tested and reference compounds were administered once (in the morning) in a dose of 1 U/kg bw. A subcutaneous (sc.) way of administration was chosen, as such a way is planned in the clinical application. Before hypoglycaemia occurred, the animals were protected with a 20% solution of glucose, administered just before injection of the studied compounds.

Glucose concentrations were analysed in 9 time points, up to 24 hours after administration of the insulins. The profiles were compared individually in each animal, because of the small group and high variability of the initial glucose levels in the animals.

From the course of the glycaemia curves, one may conclude a dissimilarity of the profiles of action of both compared analogues. Insulin SK3R, when compared to insulin AKR, is characterised by a distinctly slower start of action (prolonged absorption), later maximum effect (4 hours vs. 1-2 hours) and a more flat glycaemia profile up to 10 hours after administration of the preparation (smaller fluctuations of concentration in the profiles).

On the grounds of the presented results of the studies, it may be ascertained that the SK3R analogue has a stable prolonged activity profile, even after single administration, characteristic for so-called peakless long-acting insulins, and a prolonged action. These properties confirm the possibility of therapeutic application of the SK3R analogue as a base insulin administered once per day.

The result showing the glucose concentration in the blood of 5 Rhesus monkeys participating in the test (one of the monkeys was excluded from the test because of hypoglycaemia symptoms) after single administration of insulin SK3R in a dose of 1 U/kg bw., in comparison to insulin AKR, are shown in Table 9.

Figure 13:
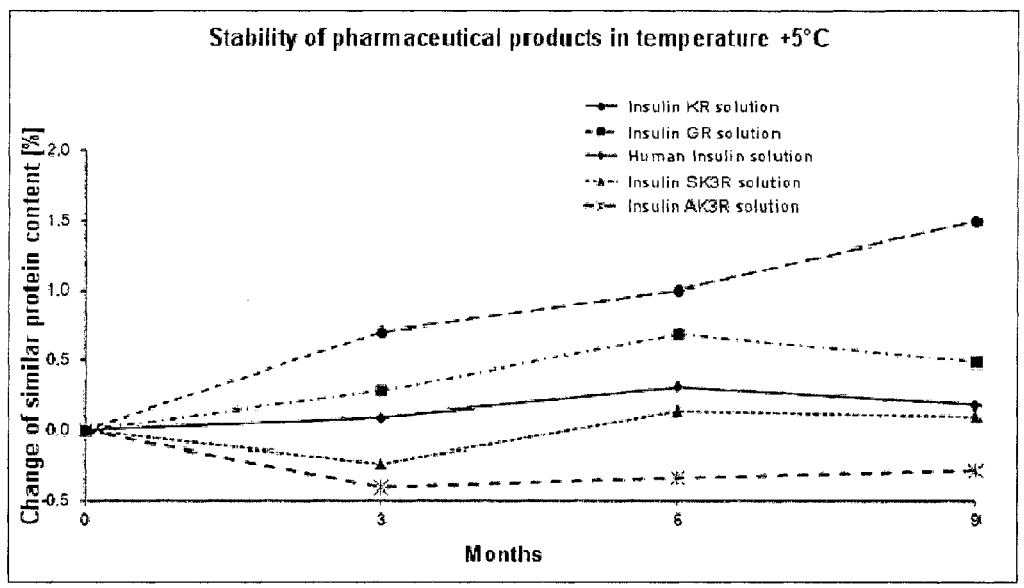
FIG. 13 shows individual graphs illustrating the differences in shapes of 12-hour profiles of the glucose concentration in the blood of monkeys with diabetes after single administration of insulin SK3R and insulin AKR in a dose of 1 U/kg bw., where: M128, M210, F143, F156, M51—numbers and codes of animals in the study.

Comprehensive graphs showing the differences in profiles of the hypoglycaemising action of insulin SK3R and insulin AKR with Rhesus monkeys after single administration in a dose of 1 U/kg bw. are shown in FIG. 13.

Example 23

Study of Insulin SK3R Activity on Dogs

Hypoglycaemic activity of insulin SK3R in comparison to insulin AKR (exponent of the group of compounds included in patent application No. WO 2010/002283 A2) was carried out on healthy Beagle dogs confirmed the observations from studies on other mammals, which prove the novel way of the pharmacological action of the SK3R analogue.

The study was carried out on 16 dogs (8 females and 8 males). The dogs were divided into groups depending on the administered dose: 8 animals received the studied insulins in a dose of 0.5 U/kg bw., and 8 others—in a dose of 1 U/kg bw. Both compounds were administered once subcutaneously. Before hypoglycaemia occurred, the animals were protected with a 20% solution of glucose, administered just before injection of the insulins. The glycaemic profile was determined up to 24 hours after administration of the preparations, and the glucose concentration was determined in 8 time points.

In the analysis, the glucose levels in groups receiving insulin SK3R and insulin AKR in both doses were compared. The statistical significance of differences in glucose concentrations in the individual time points was checked by a t-test for unpaired variables ($\alpha=0.05$).

Both after administration of 0.5 U/kg bw. and 1 U/kg bw., significant statistical differences were observed between the glucose levels in blood after administration of insulin AKR and insulin SK3R in measurement points from 0.5 to 6-8 hours. The average glycaemia profiles after administration of insulin SK3R have an evidently peakless, very even course, which is in contrast with the profiles for insulin AKR, where a rapid and strong initial action is observed. No significant fluctuations have been observed in the course of glycaemia after administration of insulin SK3R, including postprandial fluctuations, which proves the fact that the compounds ensure a stable glucose level up to $24^{th}$ hour after its administration.

The results showing average glucose concentrations in blood of healthy Beagle dogs after single administration of insulin SK3R in doses: 0.5 U/kg bw. and 1 U/kg bw., in comparison with insulin AKR (together with statistical evaluation), are shown in Table 10.

Figure 14:
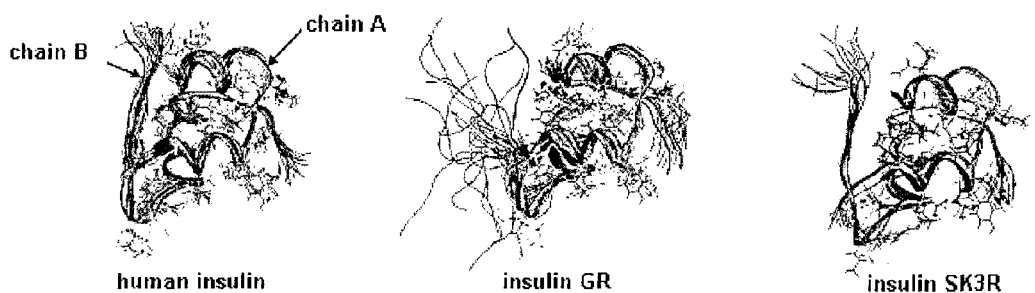
FIG. 14 shows graphs illustrating the differences in shapes of 24-hour profiles of the glucose concentration in the blood of Beagle dogs after single administration of insulin SK3R and insulin AKR in doses of 0.5 U/kg bw. and 1 U/kg bw.

Graphs showing the differences in averaged profiles of the hypoglycaemising action of insulin SK3R and insulin AKR with Beagle dogs after single administration in doses of 0.5 U/kg bw. and 1 U/kg bw. are shown in FIG. 14.

TABLE 9

Glucose concentration in the blood of Rhesus monkeys after single administration of insulin SK3R n a dose of 1 U/kg bw., in comparison to insulin AKR.

| Insulin | No. and code of the animal | Glucose concentration in the blood of the individual monkeys (mmol/l) Blood sampling time (hours) | | | | | | | | |
|---|---|---|---|---|---|---|---|---|---|---|---|
| | | 0 | 0.5 | 1 | 2 | 4 | 6 | 8 | 10 | 12 | 24 |
| SK3R 1 U/kg bw. | M128 | 4.0 | 5.2 | 3.7 | 2.8 | 2.7 | 4.4 | 4.3 | 4.3 | 5.0 | 3.8 |
| | M210 | 10.9 | 11.9 | 9.7 | 7.5 | 6.0 | 6.55 | 7.1 | 9.6 | 10.4 | 10.3 |
| | M51 | 12.1 | 11.1 | 8.6 | 5.0 | 5.1 | 7.4 | 9.6 | 8.8 | 13.0 | 11.1 |
| | F143 | 11.5 | 12.1 | 10.5 | 8.6 | 9.3 | 13.8 | 16.2 | 13.8 | 14.4 | 13.8 |
| | F156 | 4.4 | 10.2 | 5.7 | 3.7 | 3.6 | 5.2 | 5.2 | 5.4 | 5.7 | 5.2 |
| AKR 1 U/kg bw. | M128 | 4.6 | 4.4 | 2.8 | 1.7 | 1.0 | 3.3 | 5.2 | 6.0 | 5.6 | 5.1 |
| | M210 | 10.6 | 12.0 | 8.3 | 3.8 | 2.9 | 6.15 | 9.4 | 10.4 | 10.8 | 12.1 |
| | M51 | 16.7 | 16.1 | 10.0 | 3.2 | 5.0 | 14.3 | 12.1 | 14.2 | 15.6 | 16.0 |
| | F143 | 11.7 | 13.1 | 8.3 | 1.3 | 1.4 | 7.0 | 11.1 | 12.9 | 13.3 | 14.4 |
| | F156 | 5.2 | 4.1 | 1.9 | 2.6 | 2.4 | 5.1 | 6.3 | 6.1 | 6.5 | 6.3 |

Glucose concentrations are reported in mmol/l. In order to recalculate glycaemia values to mg/dl units, the following conversion factor is used: 1 mmol/l = 18 mg/dl.

TABLE 10

Average glucose concentrations in the blood of Beagle dogs after single administration of insulin SK3R in doses 0.5 U/kg bw. and 1 U/kg bw. in comparison with insulin AKR. Value of p calculated by one-sided t test for unpaired variables; significance level $\alpha = 0.05$.

| Insulin/Group | | Average glucose concentration in the blood of dogs in the individual groups (mmol/l) Blood sampling time (hours) | | | | | | | | |
|---|---|---|---|---|---|---|---|---|---|---|
| | | 0 | 0.5 | 1 | 2 | 4 | 6 | 8 | 12 | 24 |
| SK3R | Average | 13.825 | 4.225 | 4.250 | 4.750 | 4.800 | 4.775 | 4.900 | 4.675 | 4.863 |
| 0.5 U/kg bw. | SD | 6.652 | 0.908 | 0.621 | 0.233 | 0.239 | 0.311 | 0.421 | 0.453 | 0.297 |
| AKR | Average | 11.075 | 2.213 | 1.900 | 2.138 | 5.013 | 5.113 | 4.975 | 4.950 | 5.138 |
| 0.5 U/kg bw. | SD | 2.639 | 0.426 | 0.262 | 0.478 | 0.785 | 0.348 | 0.306 | 0.298 | 0.226 |
| | Value of p | 0.147721 | 0.0000* | 0.0000* | 0.0000* | 0.2379 | 0.0300* | 0.3448 | 0.0865* | 0.0281* |
| SK3R | Average | 11.250 | 3.200 | 3.725 | 4.725 | 4.575 | 4.463 | 4.750 | 4.738 | 4.900 |
| 0.5 U/kg bw. | SD | 4.530 | 0.845 | 0.547 | 0.282 | 0.205 | 0.354 | 0.393 | 0.532 | 0.262 |
| AKR | Average | 10.613 | 1.971 | 1.825 | 2.488 | 3.550 | 5.400 | 5.400 | 5.025 | 5.150 |
| 0.5 U/kg bw. | SD | 1.836 | 0.335 | 0.392 | 1.217 | 1.627 | 0.605 | 0.535 | 0.526 | 0.359 |
| | Value of p | 0.3588576 | 0.0016* | 0.0000* | 0.0001* | 0.0495* | 0.0010* | 0.0075* | 0.1476 | 0.0668 |

*confirmed statistical significance of the differences
Glucose concentrations are reported in mmol/l. In order to recalculate glycaemia values to mg/dl units, the following conversion factor is used:
1 mmol/l = 18 mg/dl.

Example 24

Study on Rats with Experimental Diabetes Comparing the Prolonged Activity of Insulin SK3R to Insulin GEKR with Gender Division The study was conducted on rats with experimental diabetes. 36 animals were included to the study, totally. Three study groups were established: SK3R group, GEKR group and the control group. In each group 6 males and 6 females were tested. One-way ANOVA and t-test was used for statistical comparisons between groups.

Insulin analogues preparations were administered 2 times a day in a dose of 5 U/kg bw. for 28 days. Glycaemia profiles were determined at the start and after 1, 2, 3 and 4 weeks of repeated administration up to 12 hours after the morning dose. After the steady-state achievement (c.a. 7-14 days) the courses of weekly profiles were similar, irrespective of the testing date.

The study results confirm distinctly the thesis included in the Example 20. The comparison of insulin SK3R to the GEKR analogue with gender distinguishing shows evidently that insulin SK3R gives very stable and even pharmacodynamic effect both in males and females after the steady-state achievement. No significant differences between sexes were observed.

The nature and feature of this effect is completely different than for insulin GEKR. Glycaemic profiles after 7, 14, 21 and 28 days of the SK3R analogue administration undoubtedly show flat and very stable 12-hour glycaemic after insulin SK3R against the insulin GEKR which effect is stable only for 4-6 hours after injection, than returning to the initial values. It means that, after the achievement of equilibrium in the body, insulin SK3R is able to maintain stable glucose level close to normoglycaemia for the whole day, without circadian fluctuations during the prolonged treatment. It exactly mimic normal endogenous secretion. Such effect is not known for the other insulin analogues preparations.

The results illustrating glucose concentration in the blood of rats after 1, 2, 3 and 4 weeks of administration of insulin SK3R in a dose of 2×5 U/kg bw./day, in the model of moderately severe streptozocin diabetes in comparison with insulin GEKR and examples of the selected glycaemic profiles, with gender distinguishing are shown in Table 11 and in FIGS. 17-20.

TABLE 11

Comparison of 12-hour glycaemic profiles in study days: 0, 7, 14, 21 and 28 after repeated administration of insulin SK3R and insulin GEKR in a dose of 2 × 5 U/kg bw./day, in the model of moderately severe streptozocin diabetes, with gender distinguishing (mean ± SD).

| Time after insulin administration [h] | | Insulin GEKR | | Insulin SK3R | |
|---|---|---|---|---|---|
| | | males n = 6 | females n = 6 | males n = 6 | females n = 6 |
| Day 0 | 0* | 26.07 ± 4.68 | 22.42 ± 4.80 | 21.38 ± 3.88 | 22.61 ± 4.84 |
| | 0.5 | 16.42 ± 6.52 | 12.86 ± 5.20 | 12.55 ± 8.88 | 14.29 ± 10.53 |
| | 1 | 12.24 ± 7.70 | 6.96 ± 4.32 | 12.99 ± 9.63 | 14.57 ± 9.31 |
| | 2 | 12.05 ± 6.52 | 6.55 ± 3.69 | 13.93 ± 9.09 | 14.21 ± 9.98 |
| | 4 | 20.23 ± 6.97* | 15.77 ± 8.91 | 12.70 ± 8.08 | 13.38 ± 8.35 |
| | 6 | 21.91 ± 4.03 | 21.33 ± 4.48 | 14.51 ± 7.48 | 13.96 ± 8.32 |
| | 8 | 21.87 ± 6.85 | 21.82 ± 4.59 | 15.87 ± 7.93 | 15.21 ± 8.38 |
| | 10 | 21.75 ± 6.16 | 20.69 ± 4.83 | 18.29 ± 7.79 | 14.39 ± 8.45 |
| | 12 | 20.26 ± 3.83 | 24.13 ± 5.63 | 21.06 ± 6.82 | 15.87 ± 8.10 |
| Day 7 | 0* | 27.17 ± 4.20 | 24.27 ± 3.31 | 24.78 ± 3.40 | 19.90 ± 6.58 |
| | 0.5 | 17.31 ± 6.46 | 9.79 ± 5.59 | 16.28 ± 3.79 | 11.59 ± 6.54 |
| | 1 | 11.40 ± 7.13 | 6.49 ± 3.67* | 17.93 ± 6.27 | 14.14 ± 7.48 |
| | 2 | 10.77 ± 6.22* | 11.75 ± 5.04 | 20.36 ± 5.75 | 16.27 ± 6.92 |
| | 4 | 23.04 ± 5.13* | 20.90 ± 1.88 | 18.69 ± 5.27 | 16.43 ± 6.03 |

TABLE 11-continued

Comparison of 12-hour glycaemic profiles in study days: 0, 7, 14, 21
and 28 after repeated administration of insulin SK3R and insulin GEKR
in a dose of 2 × 5 U/kg bw./day, in the model of moderately severe
streptozocin diabetes, with gender distinguishing (mean ± SD).

| Time after insulin administration [h] | | Insulin GEKR | | Insulin SK3R | |
|---|---|---|---|---|---|
| | | males n = 6 | females n = 6 | males n = 6 | females n = 6 |
| | 6 | 22.91 ± 3.72 | 21.85 ± 3.44 | 18.21 ± 5.74 | 16.71 ± 6.00 |
| | 8 | 25.13 ± 4.25 | 21.78 ± 2.46 | 17.80 ± 6.70 | 18.52 ± 7.46 |
| | 10 | 22.92 ± 5.04 | 22.10 ± 3.19 | 21.26 ± 4.73 | 19.06 ± 7.10 |
| | 12 | 25.10 ± 3.89 | 22.00 ± 1.82 | 25.77 ± 3.85 | 20.03 ± 7.93 |
| Day 14 | 0* | 27.37 ± 3.76 | 25.53 ± 4.93 | 23.57 ± 3.97 | 18.47 ± 8.00 |
| | 0.5 | 17.46 ± 7.15 | 10.10 ± 7.47 | 16.53 ± 6.05 | 11.17 ± 6.84 |
| | 1 | 12.51 ± 7.01 | 8.05 ± 7.30 | 17.99 ± 6.41 | 12.44 ± 7.98 |
| | 2 | 13.20 ± 7.97 | 13.87 ± 9.04 | 21.05 ± 4.96 | 14.40 ± 7.44 |
| | 4 | 22.30 ± 5.83 | 19.39 ± 3.22 | 19.09 ± 4.57 | 15.19 ± 6.67 |
| | 6 | 24.98 ± 4.80* | 19.81 ± 6.10 | 18.54 ± 3.73 | 14.23 ± 7.66 |
| | 8 | 24.50 ± 4.42* | 20.88 ± 4.79 | 18.91 ± 4.59 | 15.34 ± 7.22 |
| | 10 | 25.66 ± 4.16* | 22.10 ± 4.93 | 21.37 ± 4.57 | 16.00 ± 8.36 |
| | 12 | 26.62 ± 3.84* | 23.26 ± 5.27 | 21.04 ± 6.04 | 18.71 ± 8.77 |
| Day 21 | 0* | 27.90 ± 4.96 | 21.48 ± 6.06 | 21.55 ± 4.26 | 15.45 ± 9.56 |
| | 0.5 | 18.88 ± 8.24 | 8.79 ± 8.64 | 14.05 ± 5.64 | 8.46 ± 7.78 |
| | 1 | 14.20 ± 10.72 | 6.78 ± 7.03 | 16.01 ± 7.01 | 10.65 ± 8.13 |
| | 2 | 14.27 ± 9.24 | 11.26 ± 8.67 | 19.93 ± 6.12 | 13.08 ± 9.26 |
| | 4 | 26.00 ± 4.51* | 17.59 ± 7.37 | 18.78 ± 6.44 | 12.77 ± 7.66 |
| | 6 | 26.95 ± 3.57* | 17.05 ± 9.22 | 18.69 ± 6.23 | 12.82 ± 8.14 |
| | 8 | 25.72 ± 4.15* | 17.18 ± 8.35 | 19.29 ± 7.07 | 12.66 ± 8.08 |
| | 10 | 26.62 ± 4.18 | 18.59 ± 6.93 | 19.85 ± 8.27 | 14.13 ± 6.45 |
| | 12 | 28.36 ± 2.79* | 18.72 ± 5.91 | 22.87 ± 5.51 | 15.38 ± 7.86 |
| Day 28 | 0* | 29.03 ± 3.64* | 19.07 ± 8.19 | 21.35 ± 7.71 | 15.64 ± 10.44 |
| | 0.5 | 19.32 ± 7.51 | 7.93 ± 8.42 | 16.73 ± 7.87 | 9.69 ± 10.04 |
| | 1 | 15.47 ± 10.14 | 6.81 ± 6.81 | 17.31 ± 7.50 | 11.28 ± 9.37 |
| | 2 | 18.80 ± 7.51 | 9.33 ± 7.40 | 20.51 ± 6.92 | 14.10 ± 9.19 |
| | 4 | 26.10 ± 4.87* | 15.74 ± 11.19 | 19.13 ± 5.66 | 13.17 ± 8.97 |
| | 6 | 26.12 ± 3.99* | 15.95 ± 10.39 | 17.37 ± 6.22 | 12.09 ± 8.81 |
| | 8 | 27.18 ± 3.16* | 15.12 ± 8.02 | 17.92 ± 7.05 | 13.45 ± 7.24 |
| | 10 | 26.17 ± 3.58 | 13.93 ± 7.38 | 20.32 ± 5.93 | 12.48 ± 7.14 |
| | 12 | 27.66 ± 3.34* | 16.94 ± 9.23 | 22.33 ± 5.96 | 14.58 ± 7.45 |

*measurement before insulin administration
*statistically significant difference with p ≤ 0.05. t-student test
n—number of studied animals Complex tests on animals proved that the preparations, including pharmaceutical compositions made of compounds with a general formula 1, are characterised by, after repeated administration, not only a prolonged action, but also a flat liberation profile simulating secretion of natural insulin, meaning, from the clinical point of view, a potential reduction of hypoglycaemias, particularly nocturnal hypoglycaemias. It allows one to expect that the properties of the analogues, being the subject of the invention, will enable the obtaining of drugs that will increase the effectiveness, safety and comfort of the therapy. Considering their flat liberation profile, they exhibit a similarity to the basic secretion of human insulin.

Additionally, the introduced modifications lead to the obtaining of stable pharmaceutical compositions containing new insulin analogues and/or their physiologically acceptable salts, while maintaining their biological activity; the compositions being characterised by a decrease in their solubility at the physiological pH of the injection point. This causes precipitation of a microdeposit of the insulin analogue in subcutaneous tissue, and then its gradual, slow liberation to the blood, thanks to which the therapeutic level is maintained for a longer time, defined as at least 24 hours after a single dose. The properties of these compounds and their compositions were confirmed by stability tests and activity tests on animals with experimental diabetes, during which a significantly prolonged hypoglycaemising action was ascertained.

FIGS. 6-8, FIG. 11 and FIGS. 17-20 show graphs of 12-hour glycaemia profiles after repeated administration of insulin SK3R, insulin AK3R, insulin glargine and insulin GEKR. In comparison to insulin glargine and the compounds described in patent application No. WO 2010/002283 A2, this action is significantly more stable, because, for instance, in the case of insulin glargine, it already weakens from the $6^{th}$-$8^{th}$ hour, and glycaemia returns almost to its initial values before the next dose is administered, and this fact causes hyperglycaemia and a decrease in the therapeutic effect.

In comparison to hypoglycaemic compounds being the subject of patent application No. WO 2010/002283 A2, the analogues included in this application are characterised by undeniable prolongation of absorption after single administration to animals with experimental diabetes and to healthy animals, leading to the maintaining of a decreased glucose level up to the $8^{th}$-$10^{th}$ hour after their administration. The glycaemia profiles are flat without major fluctuations from the $1^{st}$ up to at least the $8^{th}$ hour after administration of the preparations. No so-called "peaks" of activity have been observed, meaning that the submitted compounds are truly peakless insulins. FIG. 3, FIG. 9, FIG. 13 and FIG. 14 illustrate glycaemia profiles with animals, including primates, after single administration of the preparation of insulin SK3R and insulin AK3R in comparison to control solutions and other analogues.

The prolonged, stable hypoglycaemic action of compounds, according to the invention, is still better visible in tests on animals after repeated administration (4 weeks), where a stable and very favourable shape of the glycaemia profile was observed, devoid of the "sawteeth" effect described earlier. FIG. 4, FIG. 5, FIG. 10 show glycaemia profiles with rats after repeated administration of insulin SK3R and insulin AK3R preparations in comparison to insulin glargine and insulin GEKR.

From the preliminary studies carried out by advanced NMR techniques ($^1$H NMR and $^{13}$C NMR spectra obtained by NOESY, TOCSY, 1H/13C-GHSQC and 1H/13C-GHSQCTOCSY techniques have been used for structural research), it results that the steric structure of human insulin an its analogues, being the subject of the invention are similar within the static, well-defined regions. Differences occur only in the poorly defined regions. Additional amino acids (lysine and arginine) introduced to the human insulin molecule cause interactions between secondary structures and a change in the lability of undefined regions. This may have an influence on susceptibility to degradation, thus causing a change in the chemical stability of the protein. Particular differences are visible between the insulin SK3R structure (own unpublished data), being the subject of the invention, and the known structure of insulin GR (*International Journal of Biological Macromolecules*. 2011; 49: 548-554), being the subject of application No. WO 2010/002283 A2.

Figure 16:
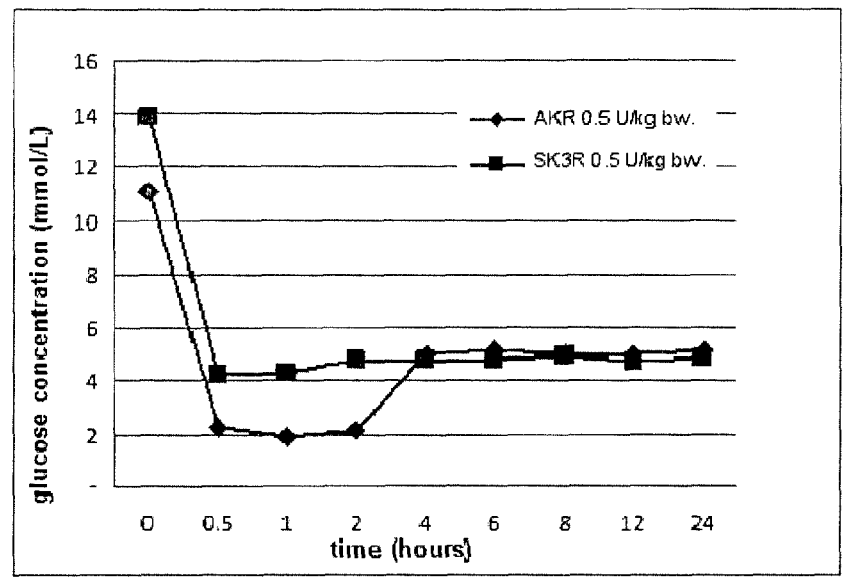
FIG. 16 shows the steric structures of human insulin monomers and its selected analogues, including insulin SK3R, according to the invention, determined based on NMR data (International Journal of Biological Macromolecules. 2011, 49: 548-554 and own unpublished data)
Figure 16:
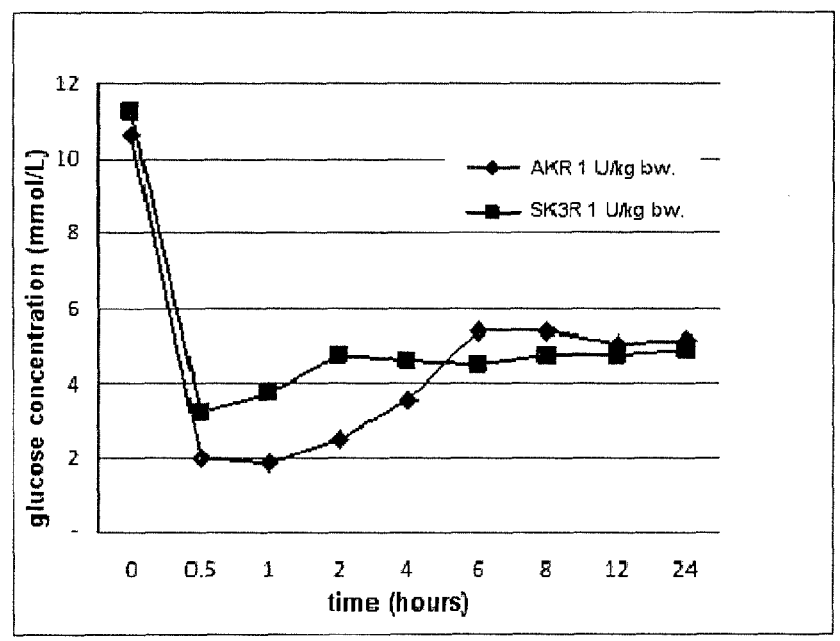
Figure 17:
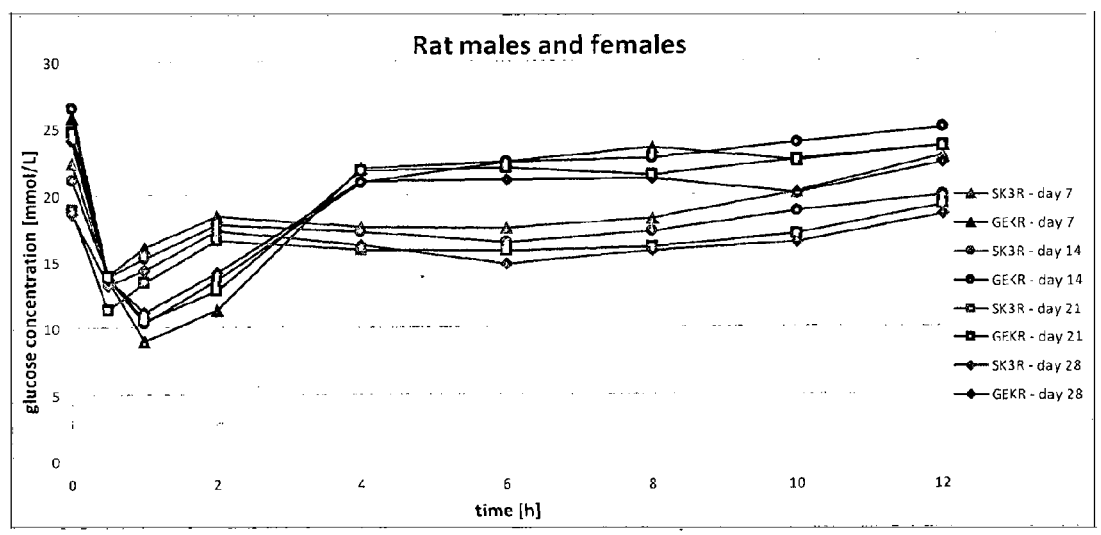
FIG. 17 shows a comprehensive graph of 12-hour average profiles of glucose concentration after 1, 2, 3 and 4 weeks of administration of insulin SK3R in a dose of 2×5 U/kg bw./day, in a model of moderately severe streptozocin diabetes, in comparison with insulin GEKR in a dose of 2×5 U/kg bw./day with gender distinguishing.
Figure 18:
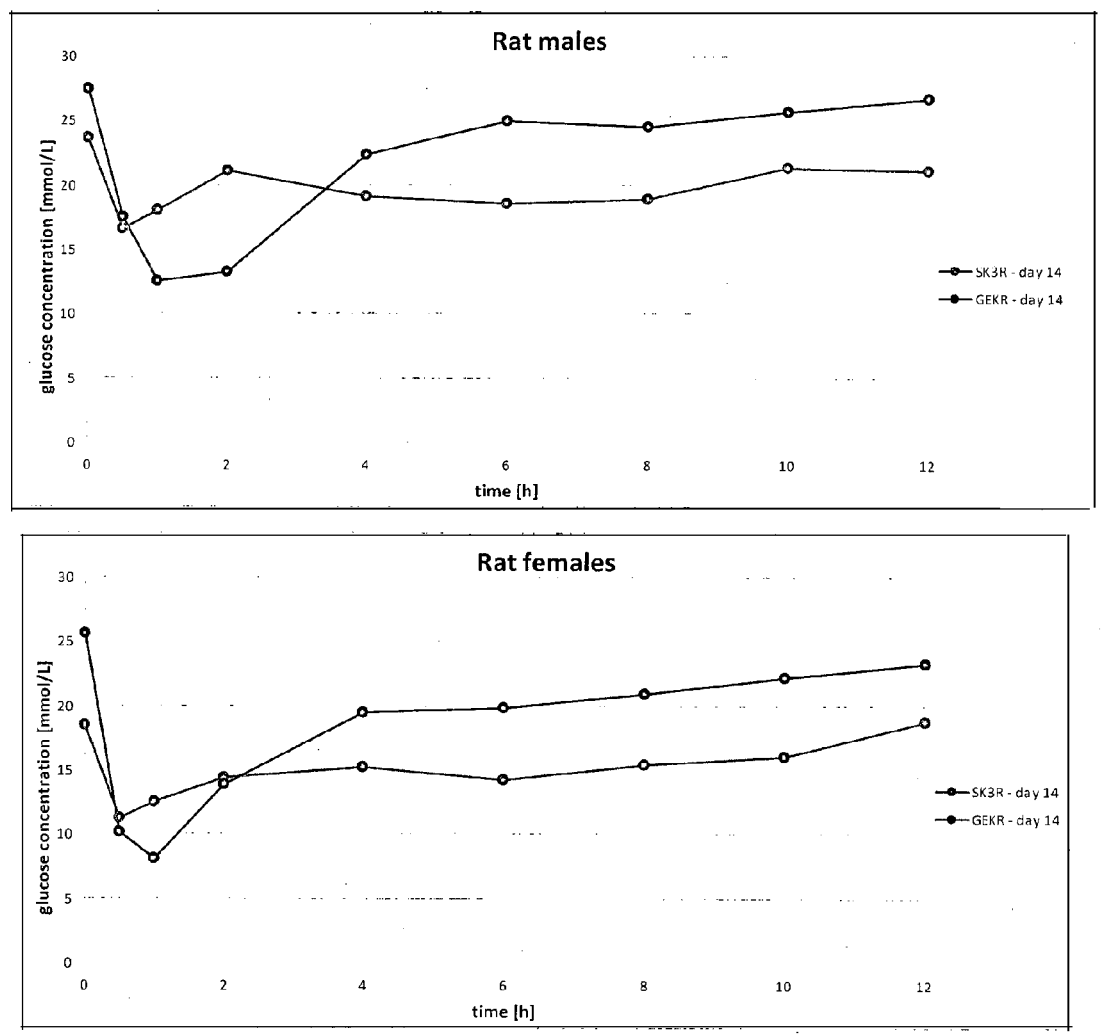
FIG. 18 shows graphs of 12-hour average profiles of glucose concentration after 2 weeks of administration of insulin SK3R in a dose of 2×5 U/kg bw./day, in a model of moderately severe streptozocin diabetes, in comparison with insulin GEKR. Graphs for males and females presented separately.
Figure 19:
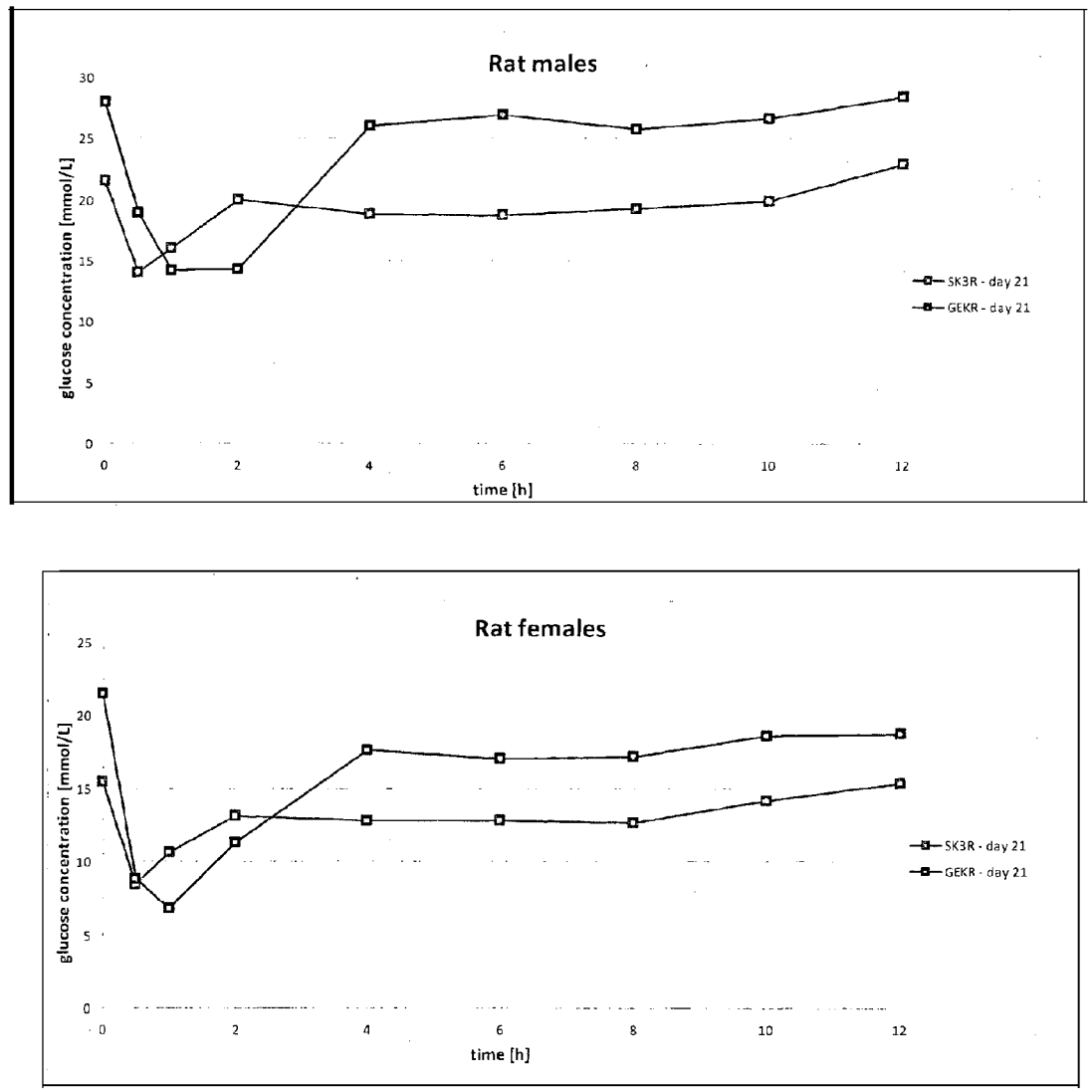
FIG. 19 shows graphs of 12-hour average profiles of glucose concentration after 3 weeks of administration of insulin SK3R in a dose of 2×5 U/kg bw./day, in a model of moderately severe streptozocin diabetes, in comparison with insulin GEKR. Graphs for males and females presented separately.
Figure 20:
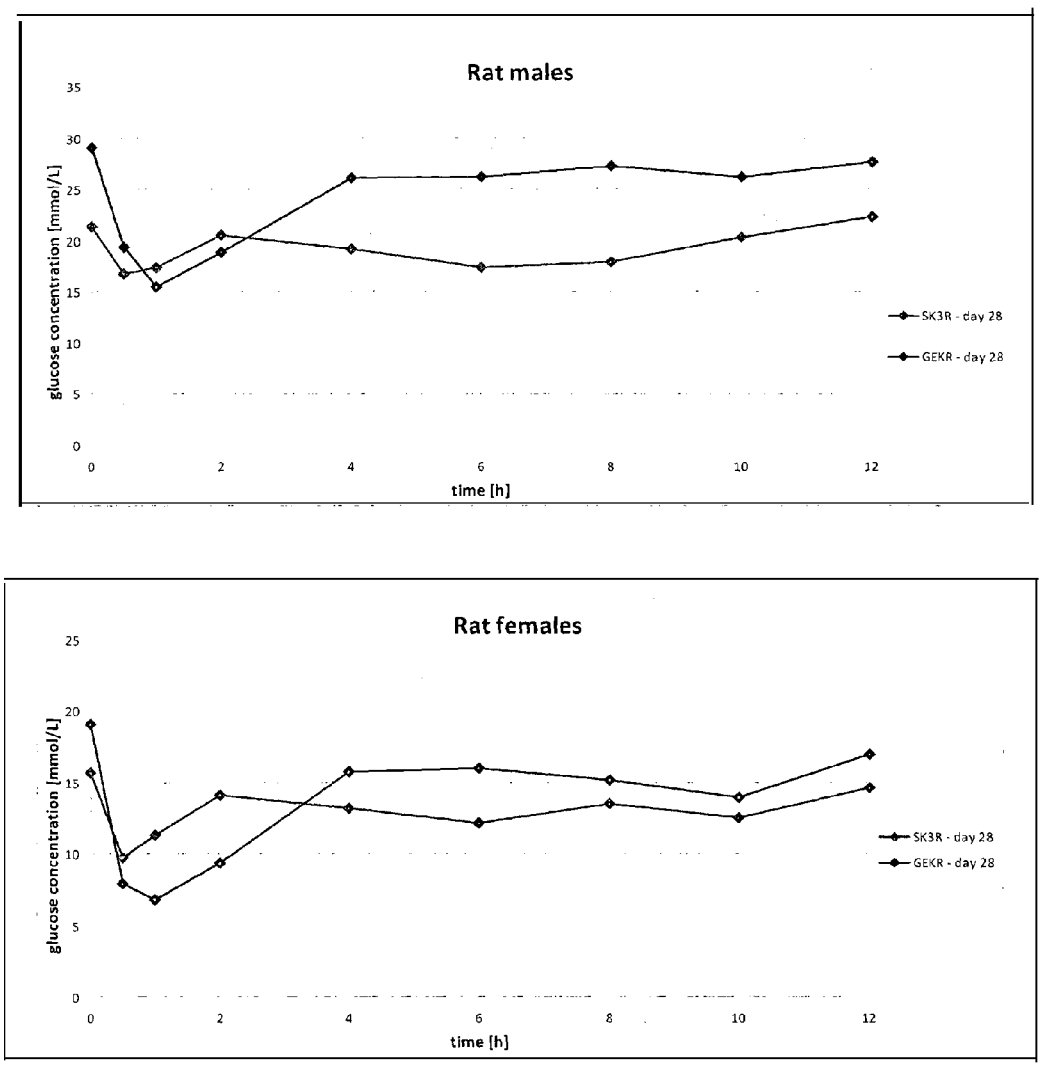
FIG. 20 shows graphs of 12-hour average profiles of glucose concentration after 4 weeks of administration of insulin SK3R in a dose of 2×5 U/kg bw./day, in a model of moderately severe streptozocin diabetes, in comparison with insulin GEKR. Graphs for males and females presented separately.

The steric structures of human insulin monomers and its selected analogues, including insulin SK3R, determined based on NMR data, are shown in FIG. 16.

The invention claimed is:

1. An insulin analogue or its pharmaceutically acceptable salt, comprising two polypeptides forming chain A and chain B, defined by general formula 1

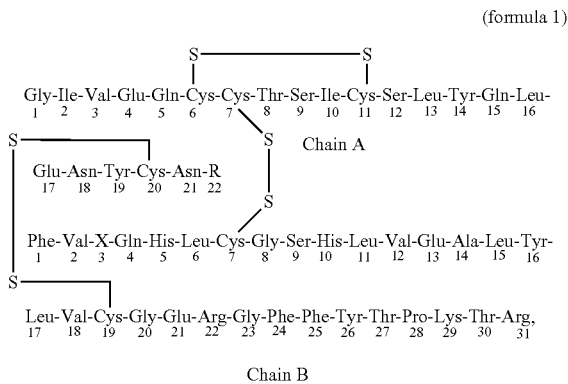

(formula 1)

Chain A

Chain B where X is a basic amino acid selected from the group consisting of lysine and arginine, and R is a neutral amino acid selected from the group consisting of glycine, alanine, serine and threonine,
wherein the amino acid sequence of chain A is set forth as SEQ ID No. 1, 2, 3 or 4, and the amino acid sequence of chain B is set forth as SEQ ID No. 5 or SEQ ID No. 6,
and the insulin analogue has an isoelectric point with values of from 6 to 8.

2. The insulin analogue of claim 1, which is recombinant.

3. The insulin analogue of claim 1, wherein when X is Lys, then R is Ser or Ala.

4. The insulin analogue of claim 1, wherein the amino acid sequences of chain A and chain B are sequences SEQ ID No. 1 with SEQ ID No. 5, SEQ ID No. 2 with SEQ ID No. 5, SEQ ID No. 3 with SEQ ID No. 5, SEQ ID No. 4 with SEQ ID No. 5, SEQ ID No. 1 with SEQ ID No. 6, SEQ ID No. 2 with SEQ ID No. 6, SEQ ID No. 3 with SEQ ID No. 6 or SEQ ID No. 4 with SEQ ID No. 6.

5. A pharmaceutical composition with prolonged therapeutic effect, comprising the insulin analogue or its pharmaceutically acceptable salt of claim 1, in a quantity of 1.3 mg/ml to 20 mg/ml.

6. The pharmaceutical composition of claim 5, wherein the insulin analogue or its pharmaceutically acceptable salt is contained in an amount of 1.4 mg/ml to 10 mg/ml.

7. The pharmaceutical composition of claim 5, which exhibits a prolonged action at a constant level without formation of a maximum of biological activity, the level being pharmacologically equivalent to the natural secretion of a basic insulin level in a healthy organism, at the same time exhibiting stability in acidic injection solutions with pH values from 3.5 to 5, which is proper for pharmaceutical forms of drugs.

8. The pharmaceutical composition of claim 5, additionally comprising from 0 to 60 μg/ml of zinc.

9. The pharmaceutical composition of claim 5, additionally comprising an isotonic substance, a preservative, an optional buffering substance, and optional substances counteracting aggregation, which are used in protein formulations.

10. The insulin analogue or its pharmaceutically acceptable salt of claim 1, formulated for the treatment of diabetes in mammals.

11. A method of treating diabetes in a subject, comprising administering to the subject the insulin analogue or its pharmaceutically acceptable salt, of claim 1.

12. The method of claim 11, wherein the effective amount of the drug per dose is contained in the range from 0.3 to 180 μg/kg of body weight of the subject, with the drug being administered once per day.

13. A method of treating a mammal suffering from diabetes, comprising administering to the mammal an effective amount of the pharmaceutical composition of claim 5, in the range of 0.3 to 180 μg/kg of body weight of the mammal.

14. The method of claim 13, wherein the mammal is human.

15. The pharmaceutical composition of claim 5, having a glycemic profile which remains unchanged across the dosage range over at least 12 hours, and which has a flat 24 hours course of glucose concentration in blood vs. time after equilibrium.

16. The pharmaceutical composition of claim 8, comprising from 10 to 60 μg/ml of zinc.

* * * * *

```
                       SEQUENCE LISTING

<160> NUMBER OF SEQ ID NOS: 26

<210> SEQ ID NO 1
<211> LENGTH: 22
<212> TYPE: PRT
<213> ORGANISM: Artificial Sequence
<220> FEATURE:
<223> OTHER INFORMATION: insulin chain A mutant

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn Gly
            20

<210> SEQ ID NO 2
<211> LENGTH: 22
<212> TYPE: PRT
<213> ORGANISM: Artificial Sequence
<220> FEATURE:
<223> OTHER INFORMATION: insulin chain A mutant

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn Ala
            20

<210> SEQ ID NO 3
<211> LENGTH: 22
<212> TYPE: PRT
<213> ORGANISM: Artificial Sequence
<220> FEATURE:
<223> OTHER INFORMATION: insulin chain A mutant

<400> SEQUENCE: 3

Gly Ile Val Glu Gln Cys Cys Thr Ser Ile Cys Ser Leu Tyr Gln Leu
1               5                   10                  15

Glu Asn Tyr Cys Asn Ser
            20

<210> SEQ ID NO 4
<211> LENGTH: 22
<212> TYPE: PRT
<213> ORGANISM: Artificial Sequence
<220> FEATURE:
<223> OTHER INFORMATION: insulin chain A mutant
```

```
<400> SEQUENCE: 4

Gly Ile Val Glu Gln Cys Cys Thr Ser Ile Cys Ser Leu Tyr Gln Leu
1               5                   10                  15

Glu Asn Tyr Cys Asn Thr
            20

<210> SEQ ID NO 5
<211> LENGTH: 31
<212> TYPE: PRT
<213> ORGANISM: Artificial Sequence
<220> FEATURE:
<223> OTHER INFORMATION: insulin chain B mutant

<400> SEQUENCE: 5

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: insulin chain B mutant

<400> SEQUENCE: 6

Phe Val Arg Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg
            20                  25                  30

<210> SEQ ID NO 7
<211> LENGTH: 24
<212> TYPE: DNA
<213> ORGANISM: Artificial Sequence
<220> FEATURE:
<223> OTHER INFORMATION: primer KSRL

<400> SEQUENCE: 7
ggtggtcgtt ttgtcaaaca gcac                                          24

<210> SEQ ID NO 8
<211> LENGTH: 24
<212> TYPE: DNA
<213> ORGANISM: Artificial Sequence
<220> FEATURE:
<223> OTHER INFORMATION: primer KSRP

<400> SEQUENCE: 8
accacacagg tgctgtttga caaa                                          24

<210> SEQ ID NO 9
<211> LENGTH: 27
<212> TYPE: DNA
<213> ORGANISM: Artificial Sequence
<220> FEATURE:
<223> OTHER INFORMATION: primer GLYP

<400> SEQUENCE: 9
tactgcaatg gttaagtcga ctctagc                                       27
```

```
<210> SEQ ID NO 10
<211> LENGTH: 26
<212> TYPE: DNA
<213> ORGANISM: Artificial Sequence
<220> FEATURE:
<223> OTHER INFORMATION: primer GLYL

<400> SEQUENCE: 10
gagtcgactt aaccattgca gtagtt                                          26

<210> SEQ ID NO 11
<211> LENGTH: 27
<212> TYPE: DNA
<213> ORGANISM: Artificial Sequence
<220> FEATURE:
<223> OTHER INFORMATION: primer ALAP

<400> SEQUENCE: 11
tactgcaatg cttaagtcga ctctagc                                         27

<210> SEQ ID NO 12
<211> LENGTH: 26
<212> TYPE: DNA
<213> ORGANISM: Artificial Sequence
<220> FEATURE:
<223> OTHER INFORMATION: primer ALAL

<400> SEQUENCE: 12
gagtcgactt aagcattgca gtagtt                                          26

<210> SEQ ID NO 13
<211> LENGTH: 27
<212> TYPE: DNA
<213> ORGANISM: Artificial Sequence
<220> FEATURE:
<223> OTHER INFORMATION: primer THRP

<400> SEQUENCE: 13
tactgcaata cctaagtcga ctctagc                                         27

<210> SEQ ID NO 14
<211> LENGTH: 26
<212> TYPE: DNA
<213> ORGANISM: Artificial Sequence
<220> FEATURE:
<223> OTHER INFORMATION: primer THRL

<400> SEQUENCE: 14
gagtcgactt aggtattgca gtagtt                                          26

<210> SEQ ID NO 15
<211> LENGTH: 27
<212> TYPE: DNA
<213> ORGANISM: Artificial Sequence
<220> FEATURE:
<223> OTHER INFORMATION: primer ARGP

<400> SEQUENCE: 15
tttgtccgtc agcacctgtg tggttct                                         27

<210> SEQ ID NO 16
<211> LENGTH: 27
<212> TYPE: DNA
<213> ORGANISM: Artificial Sequence
<220> FEATURE:
<223> OTHER INFORMATION: primer ARGL
```

<400> SEQUENCE: 16
caggtgctga cggacaaaac gaccacc 27

<210> SEQ ID NO 17
<211> LENGTH: 27
<212> TYPE: DNA
<213> ORGANISM: Artificial Sequence
<220> FEATURE:
<223> OTHER INFORMATION: primer SERP

<400> SEQUENCE: 17
tactgcaatt cttaagtcga ctctagc 27

<210> SEQ ID NO 18
<211> LENGTH: 27
<212> TYPE: DNA
<213> ORGANISM: Artificial Sequence
<220> FEATURE:
<223> OTHER INFORMATION: primer SERL

<400> SEQUENCE: 18
agagtcgact taagaattgc agtagtt 27

<210> SEQ ID NO 19
<211> LENGTH: 27
<212> TYPE: DNA
<213> ORGANISM: Artificial Sequence
<220> FEATURE:
<223> OTHER INFORMATION: primer thrg

<400> SEQUENCE: 19
tactgcaata cttaagtcga ctctagc 27

<210> SEQ ID NO 20
<211> LENGTH: 27
<212> TYPE: DNA
<213> ORGANISM: Artificial Sequence
<220> FEATURE:
<223> OTHER INFORMATION: primer THRD

<400> SEQUENCE: 20
agagtcgact taagtattgc agtagtt 27

<210> SEQ ID NO 21
<211> LENGTH: 24
<212> TYPE: DNA
<213> ORGANISM: Artificial Sequence
<220> FEATURE:
<223> OTHER INFORMATION: primer SARGL

<400> SEQUENCE: 21
actcctaaaa cacgtggcat cgtt 24

<210> SEQ ID NO 22
<211> LENGTH: 24
<212> TYPE: DNA
<213> ORGANISM: Artificial Sequence
<220> FEATURE:
<223> OTHER INFORMATION: primer SARGP

<400> SEQUENCE: 22
aacgatgcca cgtgttttag gagt 24

```
<210> SEQ ID NO 23
<211> LENGTH: 9550
<212> TYPE: DNA
<213> ORGANISM: Artificial Sequence
<220> FEATURE:
<223> OTHER INFORMATION: Nucleotide sequence of a
      p5/ZUINSSer(22A)Lys(3B)Arg(31B)Arg(32B) plasmid

<400> SEQUENCE: 23
tagagcgcac gaatgagggc cgacaggaag caaagctgaa aggaatcaaa atctcgcgtg      60
cttactcccg gctgtccttc gtttcgactt tccttagttt tttggccgca ggcgtaccgt     120
ggacaggaac gtcgtgctga cgcttcatca aaaccggcgt ccgcatggca cctgtccttg     180
cagcacgact gcgaagtagt gaagggcact ggtgcaacgg aaattgctca tcagctcagt     240
attgcccgct cttcccgtga ccacgttgcc tttaacgagt agtcgagtca taacgggcga     300
ccacggttta taaaattctt gaagacgaaa gggcctcgtg atacgcctat ggtgccaaat     360
attttaagaa cttctgcttt cccggagcac tatgcggata ttttataggt taatgtcatg     420
ataataatgg tttcttagac gtcaggtggc aaaatatcca attacagtac tattattacc     480
aaagaatctg cagtccaccg acttttcggg gaaatgtgcg cggaaccccct atttgtttat     540 ttttctaaat tgaaaagccc ctttacacgc gccttgggga taaacaaata aaagattta     600 acattcaaat atgtatccgc tcatgagaca ataaccctga taaatgcttc tgtaagttta     660
tacataggcg agtactctgt tattgggact atttacgaag aataatattg aaaaaggaag     720
agtatgagta ttcaacattt ccgtgtcgcc ttattataac ttttttcctt tcatactcat     780
aagttgtaaa ggcacagcgg cttattccct ttttgcggc attttgcctt cctgtttttg      840
ctcacccaga gaataaggga aaaaacgccg taaaacggaa ggacaaaaac gagtgggtct     900
aacgctggtg aaagtaaaag atgctgaaga tcagttgggt gcacgagtgg ttgcgaccac     960
tttcattttc tacgacttct agtcaaccca cgtgctcacc gttacatcga actggatctc    1020
aacagcggta agatccttga gagttttcgc caatgtagct tgacctagag ttgtcgccat    1080
tctaggaact ctcaaaagcg cccgaagaac gttttccaat gatgagcact tttaaagttc    1140
tgctatgtgg gggcttcttg caaaaggtta ctactcgtga aaatttcaag acgatacacc    1200
cgcggtatta tcccgtgttg acgccgggca agagcaactc ggtcgccgca gcgccataat    1260
agggcacaac tgcggcccgt tctcgttgag ccagcggcgt tacactattc tcagaatgac    1320
ttggttgagt actcaccagt cacagaaaag atgtgataag agtcttactg aaccaactca    1380
tgagtggtca gtgtcttttc catcttacgg atggcatgac agtaagagaa ttatgcagtg    1440
ctgccataac gtagaatgcc taccgtactg tcattctctt aatacgtcac gacggtattg    1500
catgagtgat aacactgcgg ccaacttact tctgacaacg atcggaggac gtactcacta    1560
ttgtgacgcc ggttgaatga agactgttgc tagcctcctg cgaaggagct aaccgctttt    1620
ttgcacaaca tggggatca tgtaactcgc gcttcctcga ttggcgaaaa acgtgttgt     1680 acccccctagt acattgagcg cttgatcgtt gggaaccgga gctgaatgaa gccataccaa    1740
acgacgagcg gaactagcaa ccccttggcct cgacttactt cggtatggtt tgctgctcgc    1800
tgacaccacg atgcctgcag caatggcaac aacgttgcgc aaactattaa actgtggtgc    1860
tacggacgtc gttaccgttg ttgcaacgcg tttgataatt ctggcgaact acttactcta    1920
gcttcccggc aacaattaat agactggatg gaccgcttga tgaatgagat cgaagggccg    1980
ttgttaatta tctgacctac gaggcggata agttgcagg accacttctg cgctcggccc    2040
ttccggctgg ctccgcctat ttcaacgtcc tggtgaagac gcgagccggg aaggccgacc    2100
```

```
ctggtttatt gctgataaat ctggagccgg tgagcgtggg tctcgcggta gaccaaataa    2160
cgactattta gacctcggcc actcgcaccc agagcgccat tcattgcagc actggggcca    2220
gatggtaagc cctcccgtat cgtagttatc agtaacgtcg tgaccccggt ctaccattcg    2280
ggagggcata gcatcaatag tacacgacgg ggagtcaggc aactatggat gaacgaaata    2340
gacagatcgc atgtgctgcc cctcagtccg ttgataccta cttgctttat ctgtctagcg    2400
tgagataggt gcctcactga ttaagcattg gtaactgtca gaccaagttt actctatcca    2460
cggagtgact aattcgtaac cattgacagt ctggttcaaa actcatatat actttagatt    2520
gatttaaaac ttcattttta atttaaaagg tgagtatata tgaaatctaa ctaaattttg    2580
aagtaaaaat taaattttcc atctaggtga agatcctttt tgataatctc atgaccaaaa    2640
tcccttaacg tagatccact tctaggaaaa actattagag tactggtttt agggaattgc    2700
tgagttttcg ttccactgag cgtcagaccc catcgccgtt ctcgatacgc actcaaaagc    2760
aaggtgactc gcagtctggg gtagcggcaa gagctatgcg tgaaccgtgc gcacgctcat    2820
cccggacagt tcagcaagct gctcctggga acttggcacg cgtgcgagta gggcctgtca    2880
agtcgttcga cgaggaccct ccaggcacgc gcaagacgca gcgacctgaa tttgttggta    2940
tcactcattt ggtccgtgcg cgttctgcgt cgctggactt aaacaaccat agtgagtaaa    3000
cctgtctccg aatggaagat ggtcagcaca cagtgttgac cgcgtaatcc ggacagaggc    3060
ttaccttcta ccagtcgtgt gtcacaactg gcgcattagg tgcgcgacca cgatcttaac    3120
ccgacagtaa cgtgacagcg gtctgacatg acgcgctggt gctagaattg ggctgtcatt    3180
gcactgtcgc cagactgtac ccgcattgag gtctttgaaa ccgtaacttc agaagcatgt    3240
acggtcagat ggcgtaactc cagaaacttt ggcattgaag tcttcgtaca tgccagtcta    3300
ttaacataag agttcattgt acgcaccgtt aaaacgcgct cagcgcgctt aattgtattc    3360
tcaagtaaca tgcgtggcaa ttttgcgcga gtcgcgcgaa ctggcgcaaa aaccgtaaaa    3420
atggatgttt tcccccgggt aaaccggaaa gaccgcgttt ttggcatttt tacctacaaa    3480
agggggccca tttggccttt aatgcgtcag gaacgctttc agcgcgttgc atgactatgc    3540
atgaaactga ttacgcagtc cttgcgaaag tcgcgcaacg tactgatacg tactttgact    3600
atggcgatcg gtttgggcgc gtctgatgcc cataaggcgt attttcggac taccgctagc    3660
caaacccgcg cagactacgg gtattccgca taaaagcctg gttttcagcc ctgataagaa    3720
gaaatcagac tgtagttaca gacgagtcgt caaaagtcgg gactattctt ctttagtctg    3780
acatcaatgt ctgctcagca gagcgattca ctacgggagt cgtcggcgag tcatccagta    3840
tttttcctcg ctcgctaagt gatgccctca gcagccgctc agtaggtcat aaaaaggagc    3900
cgactctctg gcgactcgcc ttctctgaac accagagcga cagtgtgttg gctgagagac    3960
cgctgagcgg aagagacttg tggtctcgct gtcacacaac agtcatcgat aaatcaccga    4020
cgactcgttg ccgagtcatc cagtagtcgc tcagtagcta tttagtggct gctgagcaac    4080
ggctcagtag gtcatcagcg cgacgagccg cttttgtata aatccgaata agaaaatata    4140
tttttcaaac gctgctcggc gaaaacatat ttaggcttat tcttttatat aaaaagtttg    4200
cataacaaca tgatttaaaa agcaaatcag aaaaaagtta gttttgcgtg gtattgttgt    4260
actaaatttt tcgtttagtc ttttttcaat caaaacgcac gggtgtgggc atcctgggaa    4320
tgagaacaga ctcgcgtttt tctggaggaa cccacacccg taggacccct actcttgtct    4380
gagcgcaaaa agacctcctt ctgcggggat ttttgattaa acaatagtca ccgcagagcg    4440
gaattttatg gacgccccta aaaactaatt tgttatcagt ggcgtctcgc cttaaaatac    4500
```

```
caacgctggc tgtgcggcac ggggattttt aatcccccgg cccgttattc gttgcgaccg   4560
acacgccgtg cccctaaaaa ttagggggcc gggcaataag atctccacgg gcgacgggga   4620
tacataaacc cgacagcaga ggacgggtga tagaggtgcc cgctgcccct atgtatttgg   4680
gctgtcgtct cctgcccact gcgcgaatcc cagagatgat gaaaaaagag gcagagaaac   4740
gcgcccaggt cgcgcttagg gtctctacta cttttttctc cgtctctttg cgcgggtcca   4800
acgttttatc ttattgcttt ggtgttgtcc agggtgtcgg ggctgtgccc tgcaaaatag   4860
aataacgaaa ccacaacagg tcccacagcc ccgacacggg tgaccaggtg gcatttgtct   4920
gattgcgcgt gcgcggtccg acaaatgcac actggtccac cgtaaacaga ctaacgcgca   4980
cgcgccaggc tgtttacgtg atcctgcccc gtcctgtacg tgttttttc  accagaacaa   5040
cttcacgaag taggacgggg caggacatgc acaaaaaaag tggtcttgtt gaagtgcttc   5100
tggcggatga acgctaccaa cgttgccggg aacgcttcgg cgatgatggc accgcctact   5160
tgcgatggtt gcaacggccc ttgcgaagcc gctactaccg ataacgggct gatacaggca   5220
gctcccggag acgacacag  cttgcctgtg tattgcccga ctatgtccgt cgagggcctc   5280
tgcctgtgtc gaacggacac agcggatgcc gggagccgac aagcccgtca gggcgcgtca   5340
gcgggtttta tcgcctacgg ccctcggctg ttcgggcagt cccgcgcagt cgcccaaaat   5400
gcgggtgtcg gggcgcagcc atgacccagt cacgtagcga tagcggagtg cgcccacagc   5460
cccgcgtcgg tactgggtca gtgcatcgct atcgcctcac tatactggct taatatgtta   5520
aatcggagtg gtaattcagg gaagtgcttc atatgaccga attatacaat ttagcctcac   5580
cattaagtcc cttcacgaag atgtggcaaa ggaaaaatgt ggctatcgtg cgtaagtgca   5640
acatgtaggt tacaccgttt ccttttaca ccgatagcac gcattcacgt tgtacatcca   5700
aaaggtgaaa tgacgcctcc tcgctcactc ggtcgctacg ctcctgccgt tttccacttt   5760
actgcggagg agcgagtgag ccagcgatgc gaggacggca gagactgcgg cgggcgttac   5820
cggctcacaa ataacgggat acgcaggcag ctctgacgcc gcccgcaatg gccgagtgtt   5880
tattgcccta tgcgtccgtc tgctcaaatc aggaaggacc ggaaaaagga tgcggcgtag   5940
ccgttttttcc acgagtttag tccttcctgg ccttttttcct acgccgcatc ggcaaaaagg   6000
ataggctccg cccccctgac aagcatcacg aaatctgacg ctcaaatcag tatccgaggc   6060
gggggggactg ttcgtagtgc tttagactgc gagtttagtc tggcggcgaa acccgacagg   6120
actataaaga tcccaggcgt ttcccccctgg accgccgctt tgggctgtcc tgatatttct   6180
agggtccgca aaggggggacc tagctcccctc gtgcgctctc ctgttcctgc ctttcggttt   6240
accggtgtca atcgagggag cacgcgagag gacaaggacg gaaagccaaa tggccacagt   6300
ttccgctgtt atggccgcgt ttgtctcatt ccacgcctga cactcagttc aaggcgacaa   6360
taccggcgca aacagagtaa ggtgcggact gtgagtcaag cgggtaggca gttcgctcca   6420
agctggactg tatgcacgaa ccccccgttc gcccatccgt caagcgaggt tcgacctgac   6480
atacgtgctt gggggggcaag agtccgacta ccacgcccgt tccggtaact atcaacttga   6540
gtccaacccg tcaggctgat ggtgcgggca aggccattga tagttgaact caggttgggc   6600
gaaagacacg acaaatcgcc agtggcggta gccattggta actgagatgt ctttctgtgc   6660
tgtttagcgg tcaccgccat cggtaaccat tgactctaca gcgagagatt tatctggagt   6720
tcttgaagtg ggggcctgag tgcggctaca cgctctctaa atagacctca agaacttcac   6780
ccccggactc acgccgatgt ctggaaggac agtttaggtg actcgtctcg cacaagacag   6840
ttaccaggtt gaccttcctg tcaaatccac tgagcagagc gtgttctgtc aatggtccaa   6900
```

```
aagcagttcc ccaactgacc taaccttcga tcaaaccacc tccccaggtg ttcgtcaagg   6960
ggttgactgg attggaagct agtttggtgg aggggtccac gttttttcgt tttcagagca   7020
agagattacg cgcagaaaaa aaggatctca caaaaaagca aaagtctcgt tctctaatgc   7080
gcgtcttttt ttcctagagt agaagatcct ttttacagga gcgattatcg tcttcatcca   7140
tgaaggcgtt tcttctagga aaaatgtcct cgctaatagc agaagtaggt acttccgcaa   7200
tgaagattaa accggcctat ttcatagatc gtaaaatcag ggttttggga acttctaatt   7260
tggccggata aagtatctag cattttagtc ccaaacccct tggccgatga accccataa    7320 aaacccataa atacatacac ctactaacaa accggctact tgggggtatt tttgggtatt   7380
tatgtatgtg gatgattgtt tcatcttttg ctgtaccagg gtatgaaaag tctcagggtt   7440
ccacccagag agtagaaaac gacatggtcc catacttttc agagtcccaa ggtggggtct   7500
atacgccatc aacaagtcct gtcacaccgc caaataacat gcaaaaaatt tatgcggtag   7560
ttgttcagga cagtgtggcg gtttattgta cgttttttaa gcggatgacc gtaatccggg   7620
gtgcagatca atgactgaga caagtataaa cgcctactgg cattaggccc cacgtctagt   7680
tactgactct gttcatattt cttcatgcaa aaagtaatta caatcagtcc caaagtcagc   7740
ggtgtcccgg gaagtacgtt tttcattaat gttagtcagg gtttcagtcg ccacagggcc   7800
ccctgataat catgcccgga ttatctgaat ttctcagcgg gggctgtgag gggactatta   7860
gtacgggcct aatagactta aagagtcgcc cccgacactc cgccacaacc tgtatccaag   7920
agcggtgcct acgagcagtc ctgccgtcat gcggtgttgg acataggttc tcgccacgga   7980
tgctcgtcag gacggcagta cattgtaagg cttacgccag caagttttgt ctcagtgata   8040
acaccttatg gtaacattcc gaatgcggtc gttcaaaaca gagtcactat tgtggaatac   8100
ctccccatac aaggaaaagt atcgggagaa aaaacaaacg cccggttgtc gaggggtatg   8160
ttccttttca tagccctctt ttttgtttgc gggccaacag atctcccggt cataaagagc   8220
agcaaaaccg cgtcgtagta aaaaagccag tagagggcca gtatttctcg tcgttttggc   8280
gcagcatcat ttttcggtc caggatcaag cttcagggtt gagatgtgta taagagacag   8340
actctagcca gtcctagttc gaagtcccaa ctctacacat attctctgtc tgagatcggt   8400
gtttccaagt agaaactaca gttctaaac tgcaacttttt tctactttttt caaaggttca   8460 tctttgatgt caaagatttg acgttgaaaa agatgaaaaa gcaacttaat ctattgacta   8520
gtcctttata aatgttaaaa catatatata cgttgaatta gataactgat caggaaatat   8580
ttacaatttt gtatatatat gaaataaata aaagaggag gttcatatgc aaattttttgt   8640 taaaacttta ctttatttat ttttctcctc caagtatacg tttaaaaaca attttgaaat   8700
actggtaaaa ccattacctt agaagttgaa tcttcagata ccattgataa tgaccatttt   8760
ggtaatggaa tcttcaactt agaagtctat ggtaactatt tgttaaatct aaaattcaag   8820
ataaagaagg tattcctcca gatcaacaag acaatttaga ttttaagttc tatttcttcc   8880
ataaggaggt ctagttgttc ctctaatatt tgcaggtaaa cagttagaag atggtgctac   8940
cctgtctgat gagattataa acgtccattt gtcaatcttc taccacgatg ggacagacta   9000
tataacattc agaaagaatc taccttacat ctggtcttag ctctcgctgg atattgtaag   9060
tctttcttag atggaatgta gaccagaatc gagagcgacc tggtcgtttt gtcaaacagc   9120
acctgtgtgg ttctcacctg gttgaagcac accagcaaaa cagcttgtcg tggacacacc   9180
aagagtggac caacttcgtg tgtacctggt atgtggcgaa cgtggtttct tctacactcc   9240
taaaacacgt acatggacca tacaccgctt gcaccaaaga agatgtgagg attttgtttc   9300
```

-continued

| | |
|---|---|
| cgcggcatcg ttgaacagtg ctgtacctct atctgttccc tgtaccaact gcgccgtagc | 9360 |
| aacttgtcac gacatggaga tagacaaggg acatggttga ggagaactac tgcaattctt | 9420 |
| aagtcgactc tagctacagc ctcctttcgg cctcttgatg acgttaccaa ttcagctgag | 9480 |
| atcgatgtcg gaggaaagcc aggctgtttt ttatctcgag gatcctccga caaaaaatag | 9540 |
| agctcctagg | 9550 |

<210> SEQ ID NO 24
<211> LENGTH: 9822
<212> TYPE: DNA
<213> ORGANISM: Artificial Sequence
<220> FEATURE:
<223> OTHER INFORMATION: Nucleotide sequence of a
      p6/ZUINSSer(22A)Lys(3B)Arg(31B)Arg(32B) plasmid

<400> SEQUENCE: 24

| | |
|---|---|
| attatcatga cattaaccta taaaaatagg cgtatcacga ggccctttcg taatagtact | 60 |
| gtaattggat atttttatcc gcatagtgct ccgggaaagc tcttcaagaa ttctcatgtt | 120 |
| tgacagctta tcatcgataa gctttaatgc agaagttctt aagagtacaa actgtcgaat | 180 |
| agtagctatt cgaaattacg ggtagtttat cacagttaaa ttgctaacgc agtcaggcac | 240 |
| cgtgtatgaa ccatcaaata gtgtcaattt aacgattgcg tcagtccgtg cacatactt | 300 |
| atctaacaat gcgctcatcg tcatcctcgg caccgtcacc ctggatgctg tagattgtta | 360 |
| cgcgagtagc agtaggagcc gtggcagtgg gacctacgac taggcatagg cttggttatg | 420 |
| ccggtactgc cgggcctctt gcgggatatc atccgtatcc gaaccaatac ggccatgacg | 480 |
| gcccggagaa cgccctatag gtccattccg acagcatcgc cagtcactat ggcgtgctgc | 540 |
| tagcgctata caggtaaggc tgtcgtagcg gtcagtgata ccgcacgacg atcgcgatat | 600 |
| tgcgttgatg caatttctat gcgcacccgt tctcggagca ctgtccgacc acgcaactac | 660 |
| gttaaagata cgcgtgggca agagcctcgt gacaggctgg gctttggccg ccgcccagtc | 720 |
| ctgctcgctt cgctacttgg agccactatc cgaaaccggc ggcgggtcag gacgagcgaa | 780 |
| gcgatgaacc tcggtgatag gactacgcga tcatggcgac cacaccgtc ctgtggatcc | 840 |
| tctacgccgg ctgatgcgct agtaccgctg gtgtgggcag gacacctagg agatgcggcc | 900 |
| acgcatcgtg gccggcatca ccggcgccac aggtgcggtt gctggcgcct tgcgtagcac | 960 |
| cggccgtagt ggccgcggtg tccacgccaa cgaccgcgga atatcgccga catcaccgat | 1020 |
| ggggaagatc gggctcgcca cttcgggctc tatagcggct gtagtggcta ccccttctag | 1080 |
| cccgagcggt gaagcccgag atgagcgctt gtttcggcgt gggtatggtg gcaggccccg | 1140 |
| tggccggggg tactcgcgaa caaagccgca cccataccac cgtccgggc accggccccc | 1200 |
| actgttgggc gccatctcct tgcatgcacc attccttgcg gcggcggtgc tgacaacccg | 1260 |
| cggtagagga acgtacgtgg taaggaacgc cgccgccacg tcaacggcct caacctacta | 1320 |
| ctgggctgct tcctaatgca ggagtcgcat agttgccgga gttggatgat gacccgacga | 1380 |
| aggattacgt cctcagcgta agggagagc gtcgaccgat gcccttgaga gccttcaacc | 1440 |
| cagtcagctc ttccctctcg cagctggcta cgggaactct cggaagttgg gtcagtcgag | 1500 |
| cttccggtgg gcgcggggca tgactatcgt cgccgcactt atgactgtct gaaggccacc | 1560 |
| cgcgccccgt actgatagca gcggcgtgaa tactgacaga tctttatcat gcaactcgta | 1620 |
| ggacaggtgc cggcagcgct ctgggtcatt agaaatagta cgttgagcat cctgtccacg | 1680 |
| gccgtcgcga gacccagtaa ttcggcgagg accgctttcg ctggagcgcg acgatgatcg | 1740 |

-continued

```
gcctgtcgct aagccgctcc tggcgaaagc gacctcgcgc tgctactagc cggacagcga    1800
tgcggtattc gggatcttgc acgccctcgc tcaagccttc gtcactggtc acgccataag    1860
ccctagaacg tgcgggagcg agttcggaag cagtgaccag ccgccaccaa acgtttcggc    1920
gagaagcagg ccattatcgc cggcatggcg ggcggtggtt tgcaaagccg ctcttcgtcc    1980
ggtaatagcg gccgtaccgc gccgacgcgc tgggctacgt cttgctggcg ttcgcgacgc    2040
gaggctggat cggctgcgcg acccgatgca gaacgaccgc aagcgctgcg ctccgaccta    2100
ggccttcccc attatgattc ttctcgcttc cggcggcatc gggatgcccg ccggaagggg    2160
taatactaag aagagcgaag gccgccgtag ccctacgggc cgttgcaggc catgctgtcc    2220
aggcaggtag atgacgacca tcagggacag gcaacgtccg gtacgacagg tccgtccatc    2280
tactgctggt agtccctgtc cttcaaggat cgctcgcggc tcttaccagc ctaacttcga    2340
tcattggacc gaagttccta gcgagcgccg agaatggtcg gattgaagct agtaacctgg    2400
gctgatcgtc acggcgattt atgccgcctc ggcgagcaca tggaacgggt cgactagcag    2460
tgccgctaaa tacggcggag ccgctcgtgt accttgccca tggcatggat gtaggcgcc    2520 gccctatacc ttgtctgcct ccccgcgttg accgtaccta acatccgcgg cgggatatgg    2580
aacagacgga ggggcgcaac cgtcgcggtg catggagccg ggccacctcg acctgaatgg    2640
aaccgcggag gcagcgccac gtacctcggc ccggtggagc tggacttacc ttggcgcctc    2700
ataggtgcct cactgattaa gcattggtaa ctgtcagacc aagtttactc tatccacgga    2760
gtgactaatt cgtaaccatt gacagtctgg ttcaaatgag atatatactt tagattgatt    2820
taaaacttca ttttaatttt aaaaggatct tatatatgaa atctaactaa attttgaagt    2880
aaaaattaaa ttttcctaga aggtgaagat ccttttttgat aatctcatga ccaaaatccc    2940
ttaacgtgag tccacttcta ggaaaaacta ttagagtact ggttttaggg aattgcactc    3000
ttttcgttcc actgagcgtc agaccccatc gccgttctcg atacgctgaa aaagcaagg    3060 tgactcgcag tctgggggtag cggcaagagc tatgcgactt ccgtgcgcac gctcatcccg    3120
gacagttcag caagctgctc ctgggaccag ggcacgcgtg cgagtagggc ctgtcaagtc    3180
gttcgacgag gacctggtc gcacgcgcaa gacgcagcga cctgaatttg ttggtatcac    3240
tcatttcctg cgtgcgcgtt ctgcgtcgct ggacttaaac aaccatagtg agtaaaggac    3300
tctccgaatg gaagatggtc agcacacagt gttgaccgcg taatcctgcg agaggcttac    3360
cttctaccag tcgtgtgtca caactggcgc attaggacgc cgaccacgat cttaacccga    3420
cagtaacgtg acagcggtct gacatgccgc gctggtgcta gaattgggct gtcattgcac    3480
tgtcgccaga ctgtacggcg attgaggtct ttgaaaccgt aacttcagaa gcatgtacgg    3540
tcagatttaa taactccaga aactttggca ttgaagtctt cgtacatgcc agtctaaatt    3600
cataagagtt cattgtacgc accgttaaaa cgcgctcagc gcgcttctgg gtattctcaa    3660
gtaacatgcg tggcaatttt gcgcgagtcg cgcgaagacc cgcaaaaacc gtaaaaatgg    3720
atgttttccc ccgggtaaac cggaaaaatg gcgttttttgg cattttttacc tacaaaaggg    3780 ggcccatttg gccttttttac cgtcaggaac gctttcagcg cgttgcatga ctatgcatga    3840
aactgaatgg gcagtccttg cgaaagtcgc gcaacgtact gatacgtact ttgacttacc    3900
cgatcggttt gggcgcgtct gatgcccata aggcgtattt tcggacgttt gctagccaaa    3960
cccgcgcaga ctacgggtat tccgcataaa agcctgcaaa tcagccctga taagaagaaa    4020
tcagactgta gttacagacg agtcgtgagc agtcgggact attcttcttt agtctgacat    4080
caatgtctgc tcagcactcg gattcactac gggagtcgtc ggcgagtcat ccagtatttt    4140
```

```
tcctcgcgac ctaagtgatg ccctcagcag ccgctcagta ggtcataaaa aggagcgctg    4200
tctctggcga ctcgccttct ctgaacacca gagcgacagt gtgttgagtc agagaccgct    4260
gagcggaaga gacttgtggt ctcgctgtca cacaactcag atcgataaat caccgacgac    4320
tcgttgccga gtcatccagt agtcgccgac tagctattta gtggctgctg agcaacggct    4380
cagtaggtca tcagcggctg gagccgcttt tgtataaatc gaataagaa aatatatttt     4440 tcaaaccata ctcggcgaaa acatatttag gcttattctt ttatataaaa agtttggtat    4500
acaacatgat ttaaaaagca aatcagaaaa aagttagttt tgcgtggggt tgttgtacta    4560 aattttcgt ttagtctttt ttcaatcaaa acgcacccca gtgggcatcc tgggaatgag     4620
aacagactcg cgttttctg gaggaactgc cacccgtagg acccttactc ttgtctgagc     4680
gcaaaaagac ctccttgacg ggggattttt gattaaacaa tagtcaccgc agagcggaat    4740
tttatgcaac ccctaaaaa ctaatttgtt atcagtggcg tctcgcctta aaatacgttg     4800
gctggctgtg cggcacgggg atttttaatc ccccggcccg ttattcatct cgaccgacac    4860
gccgtgcccc taaaaattag ggggccgggc aataagtaga ccacgggcga cggggataca    4920
taaacccgac agcagaggac gggtgagcgc ggtgcccgct gcccctatgt atttgggctg    4980
tcgtctcctg cccactcgcg gaatcccaga gatgatgaaa aaagaggcag agaaacgcgc    5040
ccaggtacgt cttagggtct ctactacttt tttctccgtc tctttgcgcg gtccatgca     5100 tttatcttat tgctttggtg ttgtccaggg tgtcggggct gtgccctgac aaatagaata    5160
acgaaaccac aacaggtccc acagccccga cacgggactg caggtggcat tgtctgatt    5220 gcgcgtgcgc ggtccgacaa atgcacatcc gtccaccgta aacagactaa cgcgcacgcg    5280
ccaggctgtt tacgtgtagg tgccccgtcc tgtacgtgtt tttttcacca gaacaacttc    5340
acgaagtggc acggggcagg acatgcacaa aaaaagtggt cttgttgaag tgcttcaccg    5400
ggatgaacgc taccaacgtt gccgggaacg cttcggcgat gatggcataa cctacttgcg    5460
atggttgcaa cggcccttgc gaagccgcta ctaccgtatt cgggctgata caggcagctc    5520
ccggagacgg acacagcttg cctgtgagcg gcccgactat gtccgtcgag ggcctctgcc    5580
tgtgtcgaac ggacactcgc gatgccggga gccgacaagc ccgtcagggc gcgtcagcgg    5640
gttttagcgg ctacggccct cggctgttcg ggcagtcccg cgcagtcgcc caaaatcgcc    5700
gtgtcggggc gcagccatga cccagtcacg tagcgatagc ggagtgtata cacagccccg    5760
cgtcggtact gggtcagtgc atcgctatcg cctcacatat ctggcttaat atgttaaatc    5820
ggagtggtaa ttcagggaag tgcttcatgt gaccgaatta tacaatttag cctcaccatt    5880
aagtcccttc acgaagtaca ggcaaaggaa aaatgtggct atcgtgcgta agtgcaacat    5940
gtaggtaaag ccgtttcctt tttacaccga tagcacgcat tcacgttgta catccatttc    6000
gtgaaatgac gcctcctcgc tcactcggtc gctacgctcc tgccgtgaga cactttactg    6060
cggaggagcg agtgagccag cgatgcgagg acgcactct ctgcggcggg cgttaccggc     6120
tcacaaataa cgggatacgc aggcagtgct gacgccgccc gcaatggccg agtgtttatt    6180
gccctatgcg tccgtcacga caaatcagga aggaccggaa aaaggatgcg gcgtagccgt    6240
ttttccatag gtttagtcct tcctggcctt tttcctacgc cgcatcggca aaaaggtatc    6300
gctccgcccc cctgacaagc atcacgaaat ctgacgctca aatcagtggc cgaggcgggg    6360
ggactgttcg tagtgcttta gactgcgagt ttagtcaccg ggcgaaaccc gacaggacta    6420
taaagatccc aggcgtttcc ccctggtagc ccgcttggg ctgtcctgat atttctaggg     6480
tccgcaaagg gggaccatcg tccctcgtgc gctctcctgt tcctgccttt cggtttaccg    6540
```

```
gtgtcattcc agggagcacg cgagaggaca aggacggaaa gccaaatggc cacagtaagg    6600
gctgttatgg ccgcgtttgt ctcattccac gcctgacact cagttccggg cgacaatacc    6660
ggcgcaaaca gagtaaggtg cggactgtga gtcaaggccc taggcagttc gctccaagct    6720
ggactgtatg cacgaacccc ccgttcagtc atccgtcaag cgaggttcga cctgacatac    6780
gtgcttgggg ggcaagtcag cgactaccac gcccgttccg gtaactatca acttgagtcc    6840
aacccggaaa gctgatggtg cgggcaaggc cattgatagt tgaactcagg ttgggccttt    6900
gacacgacaa atcgccagtg gcggtagcca ttggtaactg agatgtgcga ctgtgctgtt    6960
tagcggtcac cgccatcggt aaccattgac tctacacgct gagatttatc tggagttctt    7020
gaagtggggg cctgagtgcg gctacactgg ctctaaatag acctcaagaa cttcaccccc    7080
ggactcacgc cgatgtgacc aaggacagtt taggtgactc gtctcgcaca agacagttac    7140
caggttaagc ttcctgtcaa atccactgag cagagcgtgt tctgtcaatg gtccaattcg    7200
agttccccaa ctgacctaac cttcgatcaa accacctccc caggtggttt tcaagggggtt    7260 gactggattg gaagctagtt tggtggaggg gtccaccaaa tttcgttttc agagcaagag    7320
attacgcgca gaaaaaaagg atctcaagaa aaagcaaaag tctcgttctc taatgcgcgt    7380 cttttttttcc tagagttctt gatccttttt acaggagcga ttatcgtctt catccatgaa    7440
ggcgtttgaa ctaggaaaaa tgtcctcgct aatagcagaa gtaggtactt ccgcaaactt    7500
gattaaaccg gcctatttca tagatcgtaa atcagggtt ttgggatggc ctaatttggc    7560
cggataaagt atctagcatt ttagtcccaa aaccctaccg cgatgaaacc ccataaaaac    7620
ccataaatac atacacctac taacaatcat gctactttgg ggtattttg ggtatttatg    7680 tatgtggatg attgttagta cttttgctgt accagggtat gaaagtctc agggttccac    7740 cccagaaatac gaaaacgaca tggtcccata cttttcagag tcccaaggtg gggtcttatg    7800
gccatcaaca agtcctgtca caccgccaaa taacatgcaa aaaattgcgg cggtagttgt    7860
tcaggacagt gtggcggttt attgtacgtt ttttaacgcc atgaccgtaa tccggggtgc    7920
agatcaatga ctgagacaag tataaacttc tactggcatt aggccccacg tctagttact    7980
gactctgttc atatttgaag atgcaaaaag taattacaat cagtcccaaa gtcagcggtg    8040
tcccggccct tacgttttc attaatgtta gtcagggttt cagtcgccac agggccggga    8100
gataatcatg cccggattat ctgaatttct cagcgggggc tgtgagcgcc ctattagtac    8160
gggcctaata gacttaaaga gtcgcccccg acactcgcgg acaacctgta tccaagagcg    8220
gtgcctacga gcagtcctgc cgtcatcatt tgttggacat aggttctcgc cacggatgct    8280
cgtcaggacg gcagtagtaa gtaaggctta cgccagcaag ttttgtctca gtgataacac    8340
cttatgctcc cattccgaat gcggtcgttc aaaacagagt cactattgtg gaatacgagg    8400
ccatacaagg aaaagtatcg ggagaaaaaa caaacgcccg gttgtcatct ggtatgttcc    8460
ttttcatagc cctctttttt gtttgcgggc aacagtaga cccggtcata agagcagca    8520 aaaccgcgtc gtagtaaaaa agccagcagg gggccagtat ttctcgtcgt tttggcgcag    8580
catcattttt tcggtcgtcc atcaagcttc agggttgaga tgtgtataag agacagactc    8640
tagccagttt tagttcgaag tcccaactct acacatattc tctgtctgag atcggtcaaa    8700
ccaagtagaa actacagttt ctaaactgca acttttcta cttttgcaa ggttcatctt    8760 tgatgtcaaa gatttgacgt tgaaaaagat gaaaaacgtt cttaatctat tgactagtcc    8820
tttataaatg ttaaaacata tatatagaaa gaattagata actgatcagg aaatatttac    8880 aatttttgtat atatatcttt taaataaaaa gaggaggttc atatgcaaat ttttgttaaa    8940
```

```
actttaactg atttattttt ctcctccaag tatacgttta aaaacaattt tgaaattgac    9000
gtaaaaccat taccttagaa gttgaatctt cagataccat tgataatgtt cattttggta    9060
atggaatctt caacttagaa gtctatggta actattacaa aaatctaaaa ttcaagataa    9120
agaaggtatt cctccagatc aacaagctct tttagatttt aagttctatt tcttccataa    9180
ggaggtctag ttgttcgaga atatttgca ggtaaacagt tagaagatgg tgctaccctg     9240
tctgattata ttataaacgt ccatttgtca atcttctacc acgatgggac agactaatat    9300
acattcagaa agaatctacc ttacatctgg tcttagctct cgctggtggt tgtaagtctt    9360
tcttagatgg aatgtagacc agaatcgaga gcgaccacca cgttttgtca acagcacct     9420 gtgtggttct cacctggttg aagcactgta gcaaaacagt tggtcgtgga cacaccaaga    9480
gtggaccaac ttcgtgacat cctggtatgt ggcgaacgtg gtttcttcta cactcctaaa    9540
acacgtcgcg ggaccataca ccgcttgcac caaagaagat gtgaggattt tgtgcagcgc    9600
gcatcgttga acagtgctgt acctctatct gttccctgta ccaactggag cgtagcaact    9660
tgtcacgaca tggagataga caagggacat ggttgacctc aactactgca attcttaagt    9720
cgactctagc tacagcctcc tttcggaggc ttgatgacgt taccaattca gctgagatcg    9780
atgtcggagg aaagcctccg tgttttttat cacaaaaaat ag                       9822
```

<210> SEQ ID NO 25  
<211> LENGTH: 131  
<212> TYPE: PRT  
<213> ORGANISM: Artificial Sequence  
<220> FEATURE:  
<223> OTHER INFORMATION: Amino acid sequence of a  
p5/ZUINSSer(22A)Lys(3B)Arg(31B)Arg(32B) plasmid - sequence  
obtained by translation of the seq. 23 (nucleotides 4275 to 4670)

<400> SEQUENCE: 25

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Ala Leu Ile Phe Ala Gly Lys
        35                  40                  45

Gln Leu Glu Asp Gly Ala Thr Leu Ser Asp Tyr Asn Ile Gln Lys Glu
    50                  55                  60

Ser Thr Leu His Leu Val Leu Ala Leu Ala Gly Gly Arg Phe Val Lys
65                  70                  75                  80

Gln His Leu Cys Gly Ser His Leu Val Glu Ala Leu Tyr Leu Val Cys
                85                  90                  95

Gly Glu Arg Gly Phe Phe Tyr Thr Pro Lys Thr Arg Arg Gly Ile Val
            100                 105                 110

Glu Gln Cys Cys Thr Ser Ile Cys Ser Leu Tyr Gln Leu Glu Asn Tyr
        115                 120                 125

Cys Asn Ser
    130
```

<210> SEQ ID NO 26  
<211> LENGTH: 131  
<212> TYPE: PRT  
<213> ORGANISM: Artificial Sequence  
<220> FEATURE:  
<223> OTHER INFORMATION: amino acid sequence of a  
p6/ZUINSSer(22A)Lys(3B)Arg(31B)Arg(32B) plasmid - sequence  
obtained by translation of the seq. 24 (nucleotides 4421 to 4816)

```
<400> SEQUENCE: 26

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Ala Leu Ile Phe Ala Gly Lys
        35                  40                  45

Gln Leu Glu Asp Gly Ala Thr Leu Ser Asp Tyr Asn Ile Gln Lys Glu
    50                  55                  60

Ser Thr Leu His Leu Val Leu Ala Leu Ala Gly Gly Arg Phe Val Lys
65                  70                  75                  80

Gln His Leu Cys Gly Ser His Leu Val Glu Ala Leu Tyr Leu Val Cys
                85                  90                  95

Gly Glu Arg Gly Phe Phe Tyr Thr Pro Lys Thr Arg Arg Gly Ile Val
            100                 105                 110

Glu Gln Cys Cys Thr Ser Ile Cys Ser Leu Tyr Gln Leu Glu Asn Tyr
        115                 120                 125

Cys Asn Ser
        130
```